(12) United States Patent
Fonte et al.

(10) Patent No.: US 11,867,979 B2
(45) Date of Patent: *Jan. 9, 2024

(54) METHOD AND SYSTEM TO CREATE CUSTOM, USER-SPECIFIC EYEWEAR

(71) Applicant: Bespoke, Inc., San Francisco, CA (US)

(72) Inventors: Timothy A Fonte, San Francisco, CA (US); Eric J. Varady, San Francisco, CA (US)

(73) Assignee: Bespoke, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/868,007

(22) Filed: Jul. 19, 2022

(65) Prior Publication Data

US 2022/0350174 A1 Nov. 3, 2022

Related U.S. Application Data

(63) Continuation of application No. 16/244,375, filed on Jan. 10, 2019, now Pat. No. 11,428,958, which is a
(Continued)

(51) Int. Cl.
*G02C 13/00* (2006.01)
*G02C 7/02* (2006.01)
(Continued)

(52) U.S. Cl.
CPC .......... *G02C 13/005* (2013.01); *A61B 3/0041* (2013.01); *A61B 3/111* (2013.01);
(Continued)

(58) Field of Classification Search
CPC ...... G02C 13/005; G02C 7/024; G02C 7/027; G02C 13/001; G02C 13/003;
(Continued)

(56) References Cited

U.S. PATENT DOCUMENTS 4,539,585 A 9/1985 Spackova et al.
4,730,260 A 3/1988 Mori et al.
(Continued)

FOREIGN PATENT DOCUMENTS

CN 1264474 A 8/2000
CN 107498846 A 12/2017
(Continued)

OTHER PUBLICATIONS

BeehiveDM. "Beehive Wants You to Design Your Own 3D Printed Eyewear!" YouTube. YouTube, Nov. 2, 2011. Web. Feb. 2, 2016. https://www.youtube.com/watch?v=OCykS9MD3wg.
(Continued)

*Primary Examiner* — Eunhee Kim
(74) *Attorney, Agent, or Firm* — Bookoff McAndrews, PLLC

(57) ABSTRACT

Systems and methods for creating fully custom products from scratch without exclusive use of off-the-shelf or pre-specified components. A system for creating custom products includes a computer communicatively coupled with an image capture device and configured to construct an anatomic model of the user based on captured image data and/or measurement data. The computer provides a configurable product model and enables preview and automatic or user-guided customization of the product model. A display is communicatively coupled with the computer and displays the custom product model superimposed on the anatomic model or image data of the user. The computer is further configured to provide the customized product model to a manufacturer for manufacturing eyewear for the user in accordance with the customized product model.

18 Claims, 34 Drawing Sheets

Related U.S. Application Data continuation of application No. 15/355,962, filed on Nov. 18, 2016, now Pat. No. 10,222,635, which is a continuation of application No. 14/678,219, filed on Apr. 3, 2015, now Pat. No. 9,529,213, which is a continuation of application No. 14/466,619, filed on Aug. 22, 2014, now Pat. No. 9,304,332.

(60) Provisional application No. 62/002,738, filed on May 23, 2014, provisional application No. 61/869,051, filed on Aug. 22, 2013.

(51) Int. Cl.

| | | |
|---|---|---|
| G06F 16/22 | (2019.01) | |
| G16B 5/00 | (2019.01) | |
| G16H 50/50 | (2018.01) | |
| B29D 12/02 | (2006.01) | |
| G06F 30/00 | (2020.01) | |
| H04N 23/611 | (2023.01) | |
| G06Q 30/0601 | (2023.01) | |
| G06T 19/20 | (2011.01) | |
| H04L 65/403 | (2022.01) | |
| A61B 3/00 | (2006.01) | |
| A61B 3/11 | (2006.01) | |
| G06V 40/16 | (2022.01) | |
| B33Y 10/00 | (2015.01) | |
| B33Y 50/00 | (2015.01) | |
| B33Y 80/00 | (2015.01) | |

(52) U.S. Cl.
CPC ............ *B29D 12/02* (2013.01); *G02C 7/024* (2013.01); *G02C 7/027* (2013.01); *G02C 13/001* (2013.01); *G02C 13/003* (2013.01); *G06F 16/22* (2019.01); *G06F 30/00* (2020.01); *G06Q 30/0621* (2013.01); *G06T 19/20* (2013.01); *G16B 5/00* (2019.02); *G16H 50/50* (2018.01); *H04L 65/403* (2013.01); *H04N 23/611* (2023.01); *B33Y 10/00* (2014.12); *B33Y 50/00* (2014.12); *B33Y 80/00* (2014.12); *G06T 2219/2012* (2013.01); *G06V 40/166* (2022.01); *G06V 40/169* (2022.01)

(58) Field of Classification Search
CPC ....... A61B 3/0041; A61B 3/111; B29D 12/02; G06F 16/22; G06F 30/00; G06Q 30/0621; G06T 19/20; G06T 2219/2012; G16B 5/00; G16H 50/50; H04L 65/403; H04N 23/611; B33Y 10/00; B33Y 50/00; B33Y 80/00; G06V 40/166; G06V 40/169
See application file for complete search history.

(56) References Cited

U.S. PATENT DOCUMENTS

| | | | |
|---|---|---|---|
| 4,845,641 A | 7/1989 | Ninomiya et al. | |
| 4,852,184 A | 7/1989 | Tamura et al. | |
| 5,280,570 A | 1/1994 | Jordan | |
| 5,576,778 A | 11/1996 | Fujie et al. | |
| 5,592,248 A | 1/1997 | Norton et al. | |
| 5,983,201 A | 11/1999 | Fay | |
| 6,095,650 A | 8/2000 | Gao | |
| 6,142,628 A | 11/2000 | Saigo | |
| 6,144,388 A | 11/2000 | Bornstein | |
| 6,231,188 B1 | 5/2001 | Gao et al. | |
| 6,241,355 B1 | 6/2001 | Barsky | |
| 6,533,418 B1 | 3/2003 | Izumitani et al. | |
| 6,535,223 B1 | 3/2003 | Foley | |
| 6,563,499 B1 | 5/2003 | Waupotitsch et al. | |
| 6,634,754 B2 | 10/2003 | Fukuma et al. | |
| 6,664,956 B1 | 12/2003 | Erdem | |
| 6,692,127 B2 | 2/2004 | Abitbol et al. | |
| 6,736,506 B2 | 5/2004 | Izumitani et al. | |
| 6,791,584 B1 | 9/2004 | Xie | |
| 6,792,401 B1 | 9/2004 | Nigro et al. | |
| 6,944,327 B1 | 9/2005 | Soatto | |
| 6,965,385 B2 | 11/2005 | Welk et al. | |
| 6,994,327 B2 | 2/2006 | Steffes | |
| 7,016,824 B2 | 3/2006 | Waupotitsch et al. | |
| 7,062,454 B1 | 6/2006 | Giannini et al. | |
| 7,103,211 B1 | 9/2006 | Medioni et al. | |
| 7,154,529 B2 | 12/2006 | Hoke et al. | |
| 7,167,771 B2 | 1/2007 | Ito | |
| 7,222,091 B2 | 5/2007 | Yoshida | |
| 7,287,853 B2 | 10/2007 | Toshima et al. | |
| 7,471,301 B2 | 12/2008 | Lefevre | |
| 7,607,776 B1 | 10/2009 | Lewis et al. | |
| 7,665,843 B2 | 2/2010 | Xie | |
| 7,845,797 B2 | 12/2010 | Warden et al. | |
| 8,118,427 B2 | 2/2012 | Bonnin et al. | |
| 8,380,586 B2 | 2/2013 | Paolini | |
| 8,708,494 B1 | 4/2014 | Surkov et al. | |
| 9,164,299 B2 | 10/2015 | Fisher et al. | |
| 9,341,867 B1 | 5/2016 | Kim | |
| 9,429,773 B2 | 8/2016 | Ben-Shahar | |
| 9,513,494 B2 | 12/2016 | Cussac | |
| 9,810,927 B1 | 11/2017 | Fenton et al. | |
| 2002/0093515 A1 | 7/2002 | Fay et al. | |
| 2003/0065255 A1 | 4/2003 | Giacchetti et al. | |
| 2003/0090625 A1* | 5/2003 | Izumitani ............. | G02C 13/003 351/204 |
| 2003/0123026 A1 | 7/2003 | Abitbol et al. | |
| 2004/0004633 A1 | 1/2004 | Perry et al. | |
| 2004/0189935 A1 | 9/2004 | Warden et al. | |
| 2005/0084140 A1 | 4/2005 | Kakadiaris et al. | |
| 2005/0162419 A1* | 7/2005 | Kim ....................... | G06T 15/00 382/199 |
| 2005/0190264 A1 | 9/2005 | Neal | |
| 2005/0200809 A1 | 9/2005 | Dreher et al. | |
| 2006/0023923 A1 | 2/2006 | Geng et al. | |
| 2007/0244722 A1 | 10/2007 | Wortz et al. | |
| 2008/0178088 A1 | 7/2008 | Goldstein et al. | |
| 2008/0198328 A1 | 8/2008 | Seriani et al. | |
| 2009/0051871 A1 | 2/2009 | Warden et al. | |
| 2009/0319337 A1 | 12/2009 | Xie | |
| 2010/0283844 A1 | 11/2010 | Sayag | |
| 2010/0293192 A1 | 11/2010 | Suy et al. | |
| 2010/0293251 A1 | 11/2010 | Suy et al. | |
| 2011/0022545 A1 | 1/2011 | Durney | |
| 2011/0071804 A1 | 3/2011 | Xie | |
| 2011/0234581 A1 | 9/2011 | Eikelis et al. | |
| 2011/0267578 A1 | 11/2011 | Wilson | |
| 2012/0054074 A1 | 3/2012 | Wolcott et al. | |
| 2012/0313955 A1 | 12/2012 | Choukroun | |
| 2013/0006814 A1 | 1/2013 | Inoue et al. | |
| 2013/0076884 A1 | 3/2013 | Choukroun | |
| 2013/0088490 A1 | 4/2013 | Rasmussen et al. | |
| 2013/0141468 A1 | 6/2013 | Coon | |
| 2013/0187916 A1 | 7/2013 | Toy et al. | |
| 2013/0314401 A1 | 11/2013 | Engle et al. | |
| 2013/0314410 A1 | 11/2013 | Gravois et al. | |
| 2013/0314411 A1 | 11/2013 | Turetzkey | |
| 2013/0314412 A1 | 11/2013 | Gravois et al. | |
| 2013/0314413 A1 | 11/2013 | Coon et al. | |
| 2013/0315487 A1 | 11/2013 | Turetzky | |
| 2013/0321412 A1 | 12/2013 | Coon et al. | |
| 2013/0342575 A1 | 12/2013 | Coon | |
| 2014/0240470 A1* | 8/2014 | Dias Da Silva ..... | G02C 13/005 348/49 |
| 2014/0253875 A1 | 9/2014 | Gallou et al. | |
| 2015/0049304 A1 | 2/2015 | Cussac | |
| 2015/0049306 A1 | 2/2015 | Haddadi et al. | |
| 2015/0055085 A1 | 2/2015 | Fonte et al. | |
| 2015/0055086 A1 | 2/2015 | Fonte et al. | |
| 2015/0061166 A1 | 3/2015 | Vrie et al. | |
| 2015/0127132 A1 | 5/2015 | Nyong'o et al. | |
| 2015/0127363 A1 | 5/2015 | Nyong'o et al. | |
| 2015/0235416 A1 | 8/2015 | Coon et al. | |
| 2015/0277155 A1 | 10/2015 | Raviv | |

(56) References Cited

U.S. PATENT DOCUMENTS

| | | |
|---|---|---|
| 2016/0262617 A1 | 9/2016 | Gerrans |
| 2017/0038767 A1 | 2/2017 | Cluckers et al. |
| 2017/0165933 A1 | 6/2017 | Valmassoi |
| 2018/0001581 A1 | 1/2018 | Patel et al. |
| 2018/0017815 A1 | 1/2018 | Chumbley et al. |

FOREIGN PATENT DOCUMENTS

| | | |
|---|---|---|
| CN | 107589562 A | 1/2018 |
| DE | 4224922 A1 | 2/1994 |
| DE | 10216824 | 3/2006 |
| DE | 102009004380 A1 | 7/2010 |
| EP | 1231569 A1 | 8/2002 |
| EP | 2336964 A1 | 11/2010 |
| EP | 2290607 A2 | 3/2011 |
| EP | 2746838 A1 | 6/2014 |
| EP | 2887131 A1 | 6/2015 |
| ES | 2111478 A1 | 3/1998 |
| FR | 2885231 A1 | 11/2006 |
| FR | 3024911 A1 | 2/2016 |
| FR | 3038077 A1 | 12/2016 |
| JP | H05172545 A | 7/1993 |
| JP | 2002279295 A | 9/2002 |
| JP | 2005035827 A | 2/2005 |
| JP | 2006113425 A | 4/2006 |
| JP | 2007206211 A | 8/2007 |
| JP | 2011192189 A | 9/2011 |
| KR | 20020041868 A | 6/2002 |
| KR | 20040097349 A | 11/2004 |
| WO | 9852092 A1 | 11/1998 |
| WO | 9959106 A1 | 11/1999 |
| WO | 0060513 A1 | 10/2000 |
| WO | 0179918 A1 | 10/2001 |
| WO | 2005038511 A1 | 4/2005 |
| WO | 2013045531 A1 | 4/2013 |
| WO | 2015101737 A1 | 7/2015 |
| WO | 2016195488 A1 | 12/2016 |
| WO | 2017089660 A1 | 6/2017 |
| WO | 2017174525 A1 | 10/2017 |
| WO | 2017181257 A1 | 10/2017 |

OTHER PUBLICATIONS

Luxexcel., Worlds first fully 30 printed glasses by Luxexcl, Jun. 2013., Retrieved from the Internet: URL: http://blog.luxexcel.com/news/3d-printed-glasses/, pp. 4.

Steinar Killi., Custom Design, More Than Custom to Fit, Proceedings of the 3rd International Conference on Advanced Research In Virtual And Rapid Prototyping, Leiria, Portugal, Sep. 24-29, 2007, Taylor & Francis, London [U.A.], Oct. 16, 2007, pp. 777-783.

Zao et al. "Domain independent shell for DfM and its application to sheet metal forming and injection molding". Elsevier, Computer-Aided Design 37 (2005) p. 881-898.

* cited by examiner

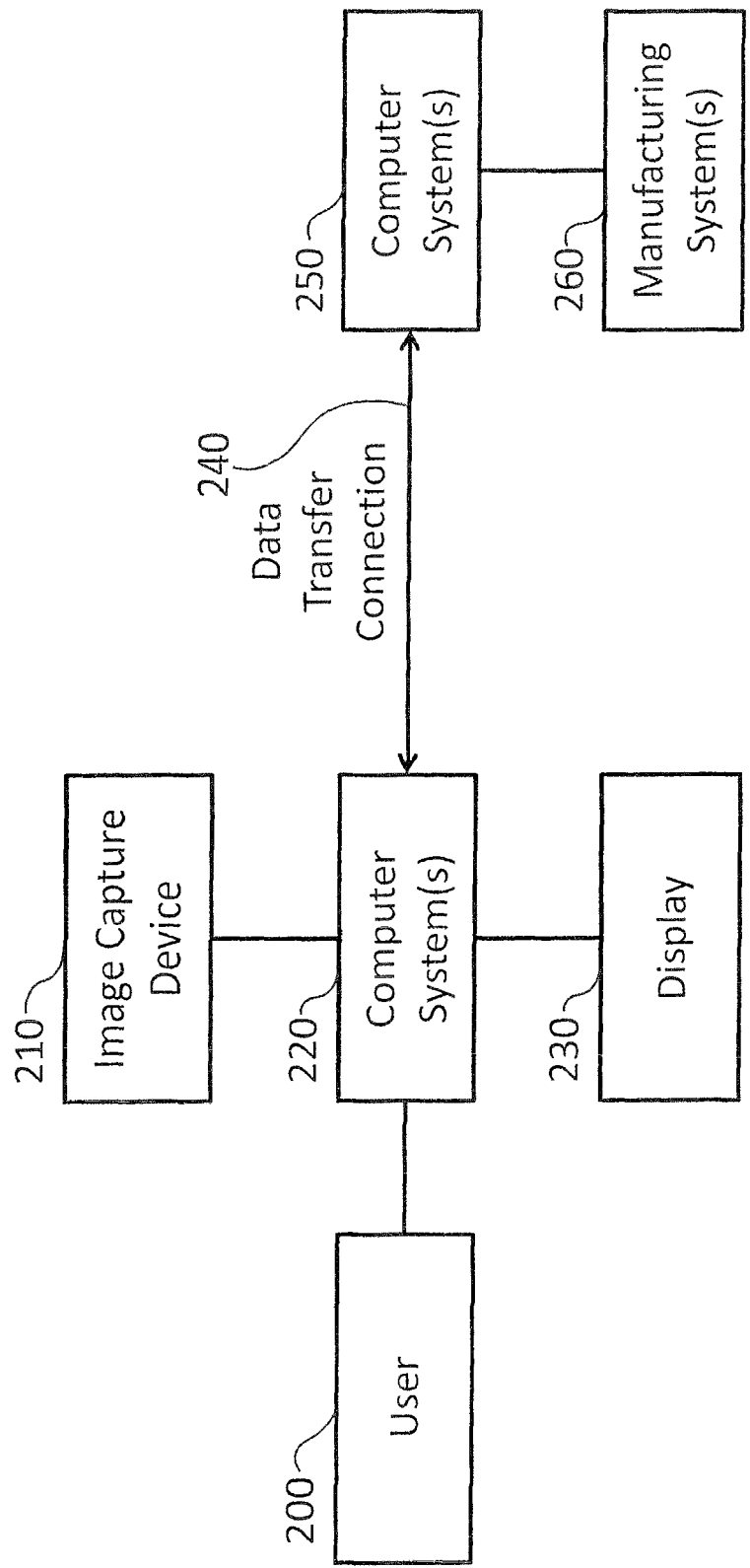

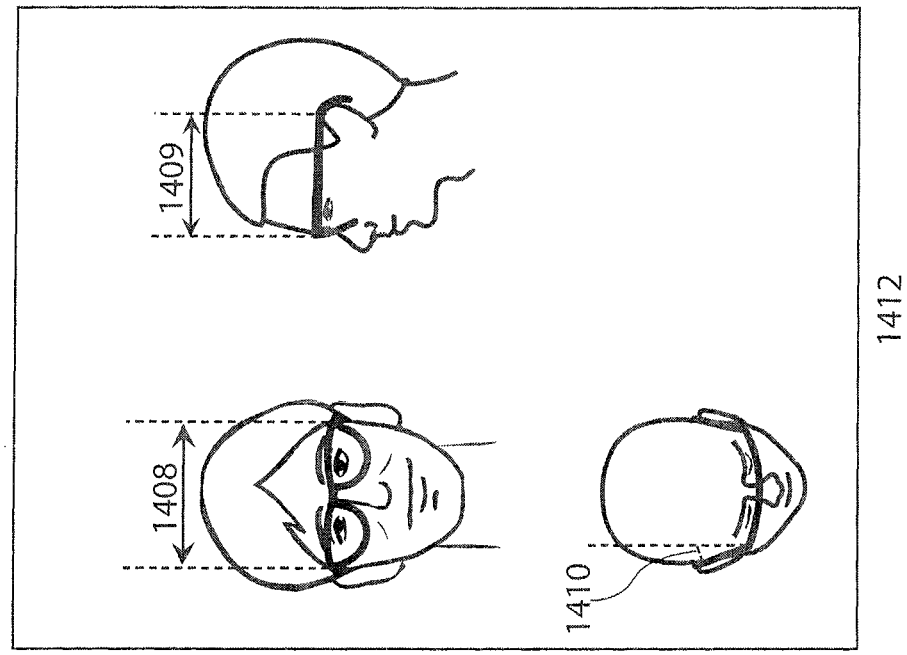
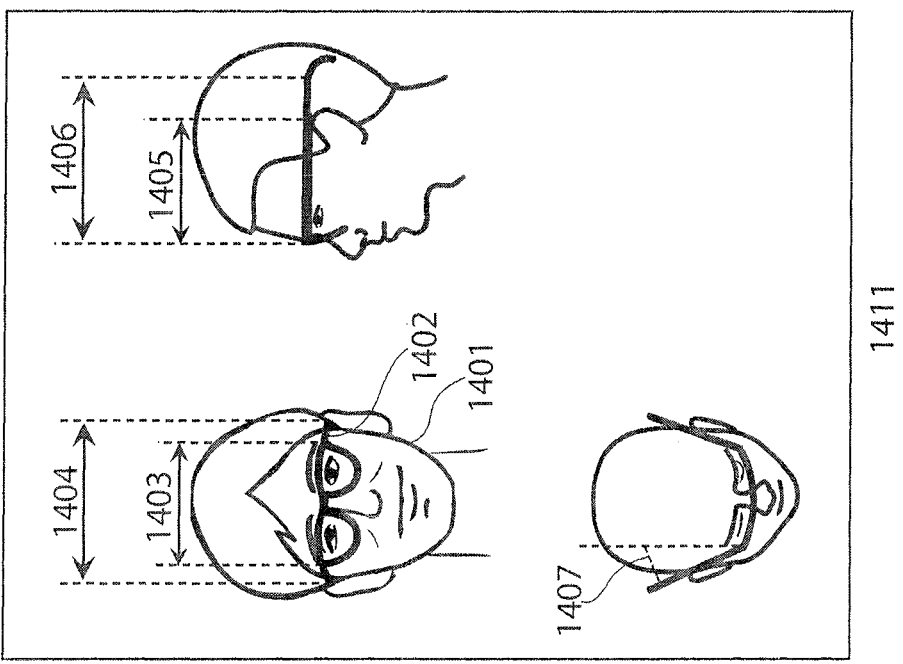
Fig. 14

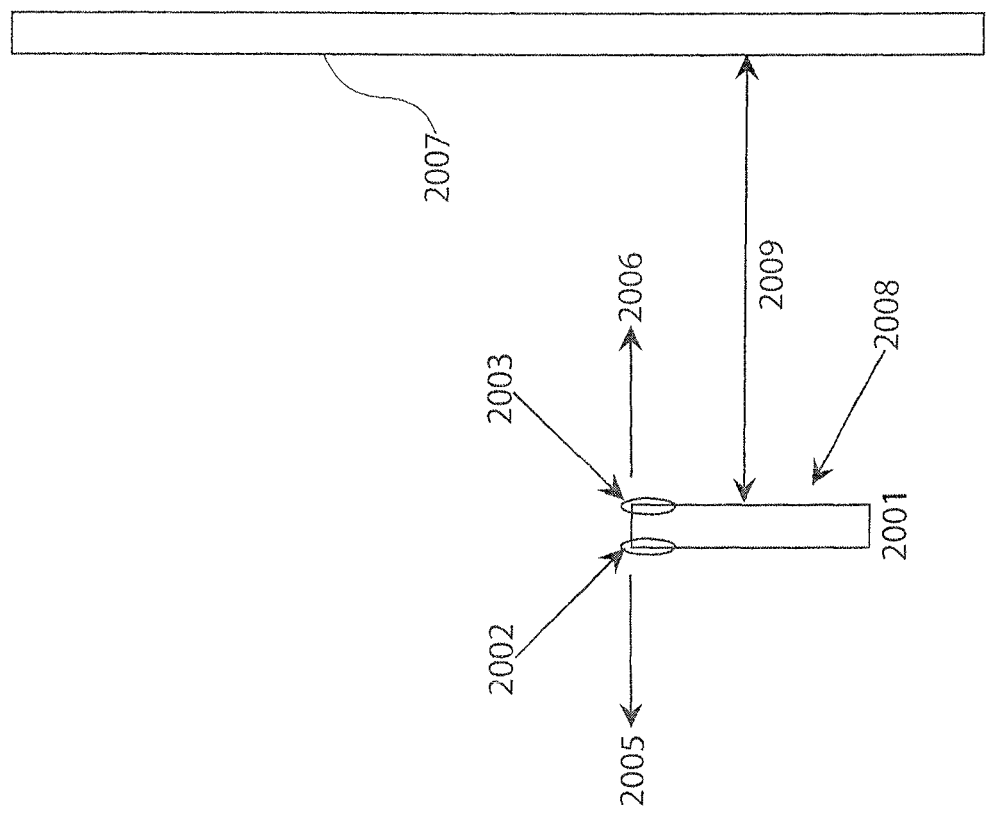
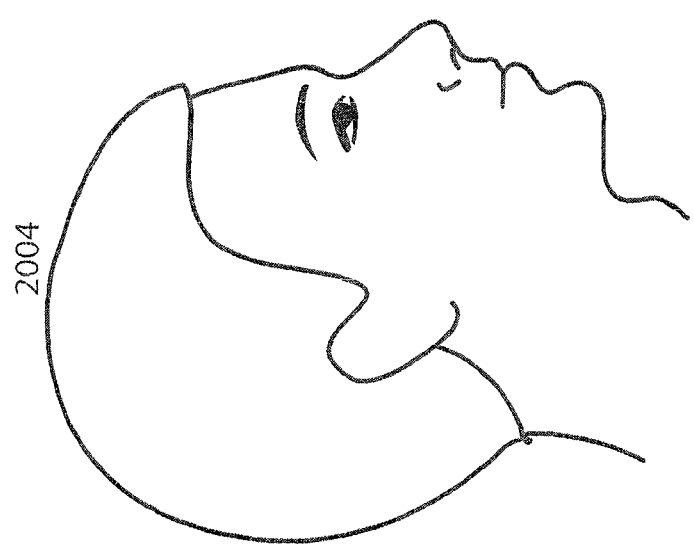
Fig. 20

METHOD AND SYSTEM TO CREATE CUSTOM, USER-SPECIFIC EYEWEAR

CROSS REFERENCE TO RELATED APPLICATIONS

This application is a continuation of and claims the benefit of priority to U.S. application Ser. No. 16/244,375, filed Jan. 10, 2019, (now U.S. Pat. No. 11,428,958), which is a continuation of and claims the benefit of priority to U.S. application Ser. No. 15/355,962, filed Nov. 18, 2016, (now U.S. Pat. No. 10,222,635), which is a continuation of and claims the benefit of priority to U.S. application Ser. No. 14/678,219, filed Apr. 3, 2015, (now U.S. Pat. No. 9,529,213), which is a continuation of and claims the benefit of priority to U.S. application Ser. No. 14/466,619, filed Aug. 22, 2014, (now U.S. Pat. No. 9,304,332), which claims priority to U.S. Provisional Applications No. 61/869,051, filed Aug. 22, 2013, and 62/002,738, filed May 23, 2014, the entire contents of which are hereby incorporated herein by reference.

FIELD OF THE INVENTION

The invention pertains to the on-demand creating, manufacturing, and delivering one-up custom products from scratch. More particularly, the subject invention creates, manufactures, and delivers custom personal products on-demand that are best suited to the needs and preferences of an individual user by building the product from a specification that is generated from automatic and/or user-guided user-specific preference profiles and by building a unique one-up custom product based on the profiles.

BACKGROUND OF THE INVENTION

Although there are many personal products that one might want to have customized or made as a one-of-a kind product tailored to a particular user, a key one of these personal products is eyewear. While the invention will be described in connection with creating producing and delivering custom eyewear, it will be appreciated that the subject invention involves the creation, production and delivering of a wide variety of products that relate to the anatomical or physical characteristics of the user as well as the users preferences for particular product. That having been said, it will be appreciated that describing the invention in terms of the creation, production and delivery of eyewear carries a large number of similarities to the creation, production and delivering of a wide variety of products customized to the features and desires of the user. What follows therefore describes invention in terms of eyewear, it being understood that the invention is not so limited.

Purchasing eyewear, while a necessity for many people, presents many challenges for consumers. For traditional in-store purchases, consumers are faced with limited in-store selection, which often requires visiting multiple stores. Yet users must explore an unmanageable array of options to find a compromise between fit, style, color, shape, price, etc. Eyewear is most commonly mass-produced, with a particular style available in one or two generic colors and sizes. Users faces are unique enough that a face can be used as a primary form of identification, yet they must choose between products made for a generic faces that are not their own. It is very difficult for users to find the one perfect pair of glasses for their unique taste, facial anatomy, and needs. They also often have difficulty visualizing what they try on because they need an optical prescription in the first place.

Recent entrants have explored the online marketplace for eyewear in an attempt to address some of these issues. However, none of the commercially available eyewear selection systems attempt to provide a completely unique one-up, from-scratch product that is customized to the user's anatomical features, as well as the user's likes and dislikes. There is therefore a need to provide a user with a completely customizable one up product that does not rely on only off-the-shelf previously designed mass-produced or stock components. The underlying form, size, shape, or other properties of the key components must be customized to provide a truly unique and custom product for the user. Once having been able to obtain the user's image data, it is then desirable to analyze and make critical measurements of the user's face, determine user preference, and on-demand manufacture a custom piece of eyewear.

It is of course desirable for the process to be as automatic as possible and be one that returns to the user the most perfect one-of-a-kind piece of eyewear that he or she has ever seen. If this can be done in a relatively swift fashion, the user is provided with a quick unique piece of eyewear is that manufactured on demand.

More particularly, the online market is rapidly growing, though there still persist numerous problems for consumers. Consumers have poor ability to try-on glasses while shopping online. Online sites have more selection than in stores, but often the consumer is faced with endless pages of glasses from which to choose. The quality of the glasses is often unknown, and consumers are even more concerned about their new glasses fitting correctly and being comfortable since they cannot physically hold or see them until they purchase.

A clear need exists for a shopping experience that enables a unique made-to-order product with high quality materials and design, at a price that users believe is fair and affordable for a made from scratch unique one up item, and an easier and more custom experience to creating and purchasing the perfect product for the individual, in this case a pair of glasses.

The concept of virtually trying on articles of clothing, including eyewear, has been discussed in the prior art for a number of years. All of the below listed patents relate to preview systems, but none relate to providing a from scratch product, relying instead on prefabricated components for a particular item.

For instance, Spackova in U.S. Pat. No. 4,539,585 describes a computer system to view articles of clothing on a person in an image. Mori, U.S. Pat. No. 4,730,260, and Ninomiya, et. al. U.S. Pat. No. 4,845,641, describe computer systems to virtually overlay eyewear on a person in an image. Jordan, U.S. Pat. No. 5,280,570, describes a system requiring a user to visit a store to virtually try on glasses with a realistic rendering of how their eyes will appear behind the glasses. Norton, U.S. Pat. No. 5,592,248, describes various methods of overlaying virtual images of eyewear on an image of a person's face to preview the appearance. Faye, U.S. Pat. No. 5,983,201, describes a system for users to virtually try on a variety of eyeglasses on their personal computer by connecting to an online store, selecting a subset of eyewear based on user preferences and sizes, and allowing user to purchase the frames. Gao, U.S. Pat. No. 6,095,650, describes another system for capturing an image and displaying eyewear superimposed on the user's image, including scaling of the image and detection of pupils to center the frames. Saigo, U.S. Pat. No. 6,142,628, describes another try-on system that also includes lens selection and display of lens shape in addition to frames. Waupotitsh, U.S. Pat. No. 7,016,824, describes an eyewear preview system that used a 3D face model provided by the user to overlay eyewear models on. Abitbol, U.S. Pat. No. 6,692,127, describes an eyewear try-on system that requires a wide-view camera to obtain a 3D model. Foley, U.S. Pat. No. 6,535,223, describes a system to determine pupillary distance based on an image of a person's face including an object of a known scale, as well as superimposing preview eyewear and allowing orders to be placed.

All of the previously described prior art explore various ways of previewing eyewear superimposed over an image of a person, but they are not on-demand systems that create, assemble and deliver a unique one-of-a-kind product from scratch. Nor do they permit previewing new custom eyewear that has not previously been mass-produced. Nor do they use the user-specific information to make eyewear better for the user. In short, they do not customize, adapt, modify, implement, or create new products such as eyewear using an on-demand system providing one-of-a-kind products from scratch. Moreover, all of the above techniques rely on previewing eyewear superimposed on the image of a person.

On the other hand, Fujie, U.S. Pat. No. 5,576,778, describes a system to design eyewear based on facial dimensions of a person. It is noted that Fujie is limited to controlling various anchor points on a Bezier curve that is extracted from facial image data to achieve a design. However, the specification of these anchor points or the control thereof by an individual is technical and difficult, made more so because these points are controlled using the user's words to control shape. Moreover, Fujie is limited to specifically sending polar coordinates based on Bezier curves to machine tools. This is much too complicated for a user, and the user's words alone may not be suitable as the only control.

Soatto, U.S. Pat. No. 6,944,327, describes a system to customize eyewear based on preview images of the user's face. However, Soatto does not take into account automatically-generated user preferences. Soatto does not describe an on-demand end-to-end process and does not describe a full system that can actually manufacture eyewear. Moreover, the Soatto method is limited to specific cameras, only a frontal face image and using a method to generate a two dimensional template of the face for sizing. Limiting the preview to only a front image prevents sizing information that is critical around the temples for ensuring a good preview and comfort for the user. Moreover, most computer systems do not have multi-lens cameras conveniently available. Note, adjustment is done only through control points while maintaining a constant perimeter rim size, which is of limited application—different users will surely require different sizes. It will be appreciated that methods describing a 3D model of the face require two or more cameras not normally available to most users.

Izumitani, U.S. Pat. No. 6,533,418, describes a system to make eyewear to order based on image previews superimposed over the user's face. However this patent only discusses changing lens shape, frame types, frame parts, and colors. It does not explain changing frame shape, but only replacing parts or changing a frame style from rimless to rimmed, which is very limiting when one wants to more fully customize eyewear. Moreover this patent does not describe automatic algorithms that size a frame to a user's face or aid in the selection of the best frames. Instead it uses a manual system like a custom order catalogue with many interchangeable parts to choose from, which could be overwhelming or too complicated for an eyewear consumer. Additionally, the preview system described only shows front and side portraits of the user with eyewear, with no interactive views, 3D views, or video, and it does not measure the dimensions of a face automatically. Further, a user is required to assist or enter information to obtain proper measurements. Finally, while the patent describes the manufacturing of eyewear, it does not clearly describe how made-to-order eyewear could actually be produced.

Warden, U.S. Pat. No. 7,845,797, describes a method for manufacturing custom eyewear that uses a front and side image in a system with multiple cameras and lighting sources. The method requires the capture of images with and without eyewear worn on the user's face before it determines the best lens position. This method is quite limited, as it requires that the user already physically possesses the eyewear he desires, and it assumes the user simply wishes to refine the lens placement in a subsequent pair of frames. In short, this is not an on-demand end-to-end system that starts from scratch to then create, design, assemble and deliver the custom product.

To satisfy the needs of a typical consumer, an easy-to-use method and system that can provide a confident and enjoyable shopping experience are necessary. The system must be capable of working with the computer hardware and image capturing equipment available to typical consumer, which limits the minimum hardware to a single-lens digital camera, stand alone or embedded in a computer system, without depth or distance-measuring capability. The embodiments of this invention describe both systems to use single camera hardware and also systems that benefit from multi-camera or depth camera technology, in the event these technologies become more pervasive in a form used by consumers or in the event that a computer system is installed in a retail or office location.

The prior art describes technologies that are designed mostly for the aesthetic preview of the eyewear on a user. A need for a more quantitative analysis exists to enable a better experience, custom fit, custom style, automated adjustment and recommendations, and the overall ability to make an eyewear design fit with each user's unique anatomy and taste.

Often pupillary distance is the only measurement taken to ensure the proper fit of eyewear, and that measurement alone is not sufficient to ensure a proper physical fitting of custom eyewear. More information is especially needed for advanced optics, such as progressive or digitally-compensated or freeform lenses. But regardless of the type and quantity of facial measurements needed to craft custom eyewear, the user should not be required to manually measure them. Most target users are not technologically savvy beyond following easy prompts in a web browser. A consumer needs an experience that is easier than picking and choosing parts and pieces or custom drawing every detail, especially when using only 2-D images, as the prior art has described. The method and system must enable easy customization, including automation of sizing and styles if the user desires automated recommendations. An average user should be able to obtain any eyewear design they desire and an excellent fit by having a design custom-fitted to his face, seeing a preview in a "what you see is what you get" display, and being able to make changes and see the effect on his face and fit.

Finally, the method and system must result in a manufacturable product, such that it can be produced and sold at a reasonable cost to the user with an acceptable delivery time. It will be appreciated that a great preview system is not useful if the product being previewed is not ultimately manufacturable at a cost and in a time frame that is satisfactory to the user ordering the product.

Thus there is a compelling need for a method and system to allow greater and more personalized customization of lenses and frames, more accurate modeling and preview, more automated or assisted eyewear selection and customization, more detailed measurements, and methods to produce customized eyewear efficiently and economically to fulfill users' orders.

SUMMARY OF THE INVENTION

The subject invention has a number of important parts. The first part is the understanding that what is desired is a from-scratch, one-up customized product that is not manufactured exclusively from off-the-shelf, previously designed, mass-produced, or stock components. As mentioned above, there are many systems which involve picking a number of components that are premade or pre-manufactured and putting them together in a customized object. However, if there are a lot of mass-produced items, the user does not have the feeling that he or she is presented with a truly unique one-off product centered on the particular profile of the user. Nor will a product made from mass-produced parts be customized to the desired degree needed to fit the user's unique anatomy and preferences. One must create at least some part of the custom product completely from scratch to fit the user, for example making some form of the product into a unique, non-mass-produced shape or size. The ability to automatically design and alter the fundamental shape and form of a custom product, with or without user guidance, is an important advantage over systems that simply let users browse and assembly mass-produced components.

The second part is how one ascertains the anatomic features of the individual, what one measures when measuring the anatomical features, and how one utilizes these anatomic measure features in the creation of a one-up from scratch object.

The third part is to be able to ascertain a user's profile, his habitual buying habits, his likes and dislikes, derived over a period of time and to be able to use all of these likes and dislikes and profiles to provide for the user a suggested unique product.

Fourthly, taking all of the above information into account with a product having been modeled after the user's anatomic features and preferences, it is important to be able to manufacture a unique product on-the-fly and deliver the product to a user in an acceptable timeline. The output being a unique product the user may have thought about wanting or which he or she may have never thought about, but is provided with due to the predictive nature of the process flow that results in the on-demand product manufacture.

Thus, at a high level, the subject system is an end-to-end system that enables a user to obtain a completely custom product from scratch without the limitation of exclusively using off-the-shelf, previously designed, mass-produced, or stock components. The product is made-to-order and best suited to the user's anatomy and personal preferences. The system may integrate steps from acquiring data about the user through delivering the final product. This goes well beyond the prior art by offering innovations that permit design and fabrication from the start without using exclusively stock, predesigned, or prefabricated parts. Rather the product is designed ab initio and automatically utilizing some or all of the following: the user's likes and dislikes, his unique anatomical attributes and unique requirements so that the finished product in terms of design, shape, fit, size, color, weight, finish, function, and artistic impression will be as close as possible to the user's wishes. Additionally, since the system may be considered an expert system, it is like providing a user with a specialist in order to provide a product with the most appropriate style and fit. The subject system, suggesting choices at every turn reflects the so-called artificial intelligence of the expert.

Not only is the system itself unique, but various techniques are described in order to develop anatomic models, directly derive certain anatomic features, various imaging techniques, ranging and size characterization techniques, scaling techniques, product presentation techniques, user interaction techniques, and custom manufacturing techniques; these techniques add to the already unique features of the subject system.

One of the features of the subject invention is the ability to obtain the features of an individual and more particularly his or her face. It is been found that self portraits, for instance done through the utilization of smart phones or electronic cameras can be useful in providing the image information necessary for the deriving the required anatomic models. Even though the so-called "selfie" or self-portrait from a camera phone is not three-dimensional, various features of the image formed from the smart phone can be utilized in generating 3-D modeling of a person's face. Thus, a convenient method of inputting a person's anatomical features, is to use the ubiquitous cell phone for the image capture, it being a finding of the subject invention that there is sufficient information in the self-portrait from a single camera to permit anatomical modeling.

While the subject invention will be described in connection with eyewear, it is within the scope of the subject invention to design, manufacture and deliver from scratch personalized products of any nature, for instance including jewelry, clothing, helmets, headphones, and other personal items. The scope also focuses on one-up, custom products made from scratch, but the methods described could also be applied to highly unique custom products that are not necessarily 100% one-up or made from scratch. Many products would benefit from having a high variety of designs to provide custom products (e.g. hundreds, thousands, millions of designs), which are too difficult to configure, stock, or manufacture using traditional methods and would be highly suitable to the methods described herein. A high degree of configurability that requires a product to be custom made-to-order is within the scope of the invention.

The comprehensiveness of the subject on-demand end-to-end system relies on the following:

Obtaining and Analyzing Image Data and Anatomic Information

In the subject invention, new methods that enable improved or alternative ways to achieve capturing images and determining anatomic information and models of the user. These include more detailed anatomic data, aesthetic analysis, and other metrics, which are used to inform both eyewear frames as well as advanced optical designs. Heretofore there has been no attempt to use anatomic information, aesthetic information, and other metrics extracted from image data to inform such detailed designs.

Obtaining Other User Information

Other user information and preferences, not obtained automatically from image data, may be used to provide further information to customize products. This information is used in novel prediction and learning algorithms that enable a product design to be altered to suit a particular user.

Configurable Product Models

The subject invention describes configurable product models that enable customization that is far more personalized than interchanging stock components to make a custom assembly. The configurable models allow entire shapes, contours, 3D surfaces, measurements, colors, finishes, and more to be completely customized for an individual user.

Product Customization

Algorithms are used that customize the shape and style of eyewear automatically for the user based on their anatomy derived from the image data that is analyzed as well as personal preferences. Also prognostication algorithms are used to predict user taste and design to assist in the custom product design and fabrication. This helps present the user with the highest probability designs upfront.

Previewing One-Up Custom Products to the User

The subject methods offer high-fidelity renderings of one-up custom products. These are not standard previews of previously existing products. The preview of one-up custom products, such as eyewear, occur prior to the product ever being produced or existing since it is made specifically and uniquely for the user. These previews involve more advanced techniques than previews of existing products because the product has not existed and prior photos, documentation or testing of the product representation does not exist yet. Everything must be generated or configured on-the-fly to enable a high quality preview of a one-up custom product that has not been built yet. The subject system is not merely rendering existing products (e.g. eyewear or parts of eyewear), but provides completely new custom designs from scratch.

User Interaction with Product Preview

Various improved methods allow the user to interact with custom product previews, alter custom designs in real-time, get feedback from others, and allow other friends/designers/opticians to also design custom products for them.

Manufacturing Custom Product

Unlike the prior art that describes very basic methods of customization, such as interchanging parts or limited customizing some components of eyewear, the subject system produces completely custom products, such as premium eyewear, from scratch. The one-up custom eyewear includes frames and lenses, built to order in a specific shape, size, and color for one user. The subject system is using advanced techniques that allow eyewear to be delivered with the same high-quality materials and finish of regular premium eyewear, but with completely custom designs.

Shopping System

Finally, the subject invention includes a shopping system that enables the user to progress through the steps necessary to obtain custom products, input their data and preferences, and select and purchase the product.

Definitions

The following definitions are for explanatory purposes to help define the breadth of words used herein. These definitions do not limit the scope of the invention, and those skilled in the art will recognize that additional definitions may be applied to each category. By way of definition as used herein, image data includes 2D image(s), digital images, video, series of images, stereoscopic images, 3D images, images acquired with standard light-sensitive cameras, images acquired with cameras that have multiple lenses, images acquired with depth cameras, images acquired with laser, infrared, or other sensor modalities. Computer systems include tablets, phones, desktops, laptops, kiosks, servers, wearable computers, network computers, distributed or parallel computers, or virtual computers. Imaging devices include single lens cameras, multiple lens cameras, depth cameras, laser cameras, infrared cameras, or digital cameras. Input devices include touchscreens, gesture sensors, keyboards, mouses, depth cameras, audio speech recognition, and wearable devices. Displays include panels, LCDs, projectors, 3D displays, heads-up displays, flexible displays, television, holographic displays, wearable displays, or other display technologies. Previewed images in the form of images, video, or interactive renderings includes images of the user superimposed with product model images, images of the user superimposed with rendering of product model, images of the anatomic and product models of the user. Anatomic models, details, and dimensions include length of features (eg length of finger), distance between features (eg distance between ears), angles, surface area of features, volume or features, 2D contours of features (eg outline of wrist), 3D models of features (eg surface of nose or ear), 3D coordinates, 3D mesh or surface representations, shape estimates or models, curvature measurements, or estimates of skin or hair color definition. A model or 3D model includes a point-cloud, parametric model, a texture-mapped model, surface or volume mesh, or other collection of points, lines, and geometric elements representing an object. Manufacturing instructions include step-by-step manufacturing instructions, assembly instructions, ordering specifications, CAM files, g-code, automated software instructions, co-ordinates for controlling machinery, templates, images, drawings, material specifications, inspection dimensions or requirements. A manufacturing system includes a computer system configured to deliver manufacturing instructions to users and/or machines, a networked computer system that includes machines configured to follow manufacturing instructions, a series of computer systems and machines that instructions are sequentially passed through. Eyewear includes eyeglass frames, sunglass frames, frames and lenses together, prescription eyewear, non-prescription (piano) eyewear, sports eyewear, or electronic or wearable technology eyewear.

Custom Products

The following is an embodiment for product that is custom fit and designed based on user anatomy derived from image data, previewed, altered by user preferences, and then manufactured to order for the first time after customization:

In accordance with an embodiment, methods are disclosed for creating custom products. One method includes acquiring, using at least one computer system, image data of a user; determining, using at least one computer system, anatomic details and/or dimensions of the user; configuring (eg, custom shape, size, dimensions, colors, finish, etc), using at least one computer system and anatomic data of the user, a new product model for the user; applying, using at least one computer system, a configurable product model to the image data or anatomic model of the user; previewing, using at least one computer system, images of the user with the configurable product model; optionally adjusting and updating the preview, using at least one computer system and/or user input, the configurable product model properties (eg, custom shape, size, dimensions, colors, finish, etc); preparing, using at least a computer system that executes instructions for manufacturing the custom product based on the previewed model; and manufacturing, using at least one computer system and manufacturing system, the new custom product.

In accordance with an embodiment, systems are disclosed for creating a custom product. One system includes an image acquisition device configured to obtain image data of a user; an input device configured to receive instructions from a user; a display configured to display image data to a user; a manufacturing system configured to produce a custom product; a digital storage device to store instructions for creating and previewing custom product; a processor configured to execute the instructions to perform the method including: acquiring, using at least one computer system, image data of a user; determining, using at least one computer system, anatomic details and/or dimensions of the user; configuring (eg, custom shape, size, dimensions, colors, finish, etc), using at least one computer system and anatomic data of the user, a new product model for the user; applying, using at least one computer system, a configurable product model to the image data or anatomic model of the user; previewing, using at least one computer system, images of the user with the configurable product model; optionally adjusting and updating the preview, using at least one computer system and/or user input, the configurable product model properties (eg, custom shape, size, dimensions, colors, finish, etc); preparing, using at least computer system, instructions for manufacturing the custom product based on the previewed model; and manufacturing, using at least one computer system and manufacturing system, the new custom product.

Systems are disclosed for creating a custom product. One system includes an image acquisition device configured to obtain image data of a user; an input device configured to receive instructions from a user; a display configured to display image data to a user; a manufacturing system configured to produce a custom product; a digital storage device to store instructions for creating and previewing a custom product; and, a processor configured to execute the instructions to perform the method.

The system includes acquiring the image data of a user; determining anatomic details and/or dimensions of the user; configuring the product to take into account these details by providing a corresponding new product model; applying a configurable product model to the image data or anatomic model of the user; previewing images of the user with the configurable product model; optionally adjusting and updating the preview; preparing, instructions for manufacturing the custom product based on the previewed model; and manufacturing the new custom product. The above can be accomplished using a properly programmed computer or can be in the form of a non-transitory computer readable medium.

More particularly, a system and method are disclosed for creating custom eyewear including at least one computer system configured to receive image data of a user. The computer system is further configured to receive other data from the user, including but not limited to demographics, prescription, preferences, etc. The system and method may include determination of quantitative anatomic information regarding the user from the user-provided data. The system and method may include customization of the properties of an eyewear model, including size, shape, color, finish, and style, to satisfy the anatomic and style needs of the user. The system also includes physically manufacturing the customized eyewear such that it matches the previewed representation.

In accordance with an embodiment, a system and method are disclosed for creating and visualizing custom eyewear including at least one computer system configured with a display. The computer system is further configured with at least one image capture device to capture image data and/or measurement data of a user. The computer system is further configured to receive other data from the user, including demographics, prescription, and preferences. The system and method may include determination of quantitative anatomic information regarding the user from the user-provided data. The system and method may include visualization of an eyewear model superimposed on the user's image data in the proper position on the user's face. The system and method may also include customization of the properties of the eyewear model and providing an updated preview of the customized eyewear superimposed on the user's image data. The system and method includes physically manufacturing the customized eyewear such that it matches the previewed representation.

In accordance with another embodiment, a system and method are disclosed for automatically customizing eyewear. The computer system is further configured to analyze the user's image data, quantitative anatomic information, and other provided data to determine optimal properties for the eyewear model such that it best matches the user's anatomy and style preferences.

In accordance with another embodiment, a system and method are disclosed for interacting with a custom eyewear model. The computer system is further configured with an interface application. The system and method may include obtaining input or commands from a user through the computer system. The system and method may further include controlling the visualization, including angle, zoom, and rotation of the eyewear preview. The system and method may further include controlling the position and orientation of the eyewear model of the user's image data. The system and method may further include enabling the user to directly customize the properties of the eyewear model and provide an updated preview.

In accordance with another embodiment, a system and method are disclosed for automatically defining optical lens designs. The system and method include analyzing the user's quantitative anatomic information, prescription information, and custom eyewear model to calculate parameters needed to inform optical design, including interpupillary distance, vertex distance, face wrap, eyewear and frame outline. The system and method are further configured to provide the parameters to a manufacturing system for the design and manufacture of custom lenses.

In accordance with another embodiment, a system and method are disclosed for a web interface for purchasing custom eyewear. The computer system is further configured with a data transfer means The system and method include providing an interface for a user to select eyewear designs, interact with, preview and customize eyewear designs, order eyewear, and transfer all information needed to build and ship custom eyewear to the user.

In accordance with another embodiment, a system and method are disclosed for controlling manufacturing of custom eyewear. The computer system is further configured to transfer data and information to at least one manufacturing system. The system and method include transferring custom eyewear models or parameters, user information, and an order to the manufacturing system. The system and method further include converting the eyewear model or parameters into manufacturing data used to control manufacturing equipment. The system and method also include providing instructions for machinery, robotics, and human operators to build, inspect, and ship custom eyewear.

In accordance with another embodiment, a system and method are disclosed for a parametric eyewear model. The system and method include a representation of eyewear that contains dimensional information regarding the shape and size of the eyewear design. The system and method further include parameters that define certain key features of the eyewear model, including but not limited to length, width, height, thickness, and radii. The system and method further include the eyewear model updating when at least one parameter is changed, automatically altering the eyewear to satisfy the constraints of all parameters.

In accordance with another embodiment, a system and method are disclosed for learning from a user's interactions and preferences involving a learning machine or predictor or prognostication machine. The system and method include tracking the actions a user takes selecting, customizing, and previewing eyewear. The system and method further include machine learning analysis of the tracked actions in addition to the user provided image data, quantitative anatomic information, and other provided information to determine user preferences for custom eyewear properties. The system and method further include making recommendations to the user based on the learning analysis.

In accordance with another embodiment, a system and method are disclosed for learning from a body of data. The system and method include building a database of image data, quantitative anatomic information, preferences, and other information relating custom eyewear to user information. The system and method include training machine learning classifiers to predict the preference of a user based on their data. The system and method further include applying the analysis to a new user to best provide a custom eyewear design that will suite the user's anatomy and preferences.

In accordance with another embodiment, a system and method are disclosed for guiding the user through a customization process. The system and method include providing a sequence of instructions or questions to guide the user through the steps needed to customize eyewear for their preferences and anatomy.

In accordance with another embodiment, a system and method are disclosed for prediction of a poor fit. The system and method include analyzing the fit between the user's quantitative anatomic information and a custom eyewear design. The system and method include using simulation, physical modeling, and analysis to predict when a sub-optical fit between the eyewear and user is designed. The system and method further include informing the user of the sub-optimal design or automatically correcting it.

In accordance with another embodiment, a system and method are disclosed for previewing vision through a customized eyewear model. The system and method include rendering a preview of the vision through a custom eyewear model, including the shape, size, and optical properties of a lens. The system and method include rendering a live or static scene that simulates the user's vision, including but not limited to distortion, area of focus, color, and other optical effects.

In accordance with another embodiment, a system and method are disclosed for copying another pair of eyewear. The system and method include receiving image data of a person, including the user, wearing eyewear. The system and method further include detecting the eyewear and analyzing the shape, color, and size. The system and method further include optimizing a custom eyewear design to match the analysis of the shape, size, and color. The system and method further include previewing the custom eyewear on the user's image data and allowing further customization.

In accordance with another embodiment, a system and method are disclosed for sharing custom eyewear previews and the ability to customize eyewear. The system and method include sending permission from at least one computer system to at least one other computer system to preview and customize eyewear on a user's image data. The system and method further include allowing a third party to interact with, customize, and update eyewear models on the user's image data. The system and method further include the third party to provide feedback and updated designs to the user.

In accordance with another embodiment, a system and method are disclosed for matching eyewear color to another object. The system and method include obtaining image data or information (including but not limited to manufacturer, part number, etc) about an object with a desired color. The system and method further include calibrating the color of the image data with a reference image. The system and method further include extracting the color properties of the desired object and applying the color to the custom eyewear model.

BRIEF DESCRIPTION OF THE DRAWINGS

These and other features of the subject invention will be better understood in connection with the Detailed Description in conjunction with the Drawings of which:

FIG. 2 is a block diagram an image capture portion of the subject system showing the interplay between an image capture device, user inputs, and other information coupled to a computer system which drives the manufacturing process;

FIG. 14 is a diagrammatic illustration of an example of automated eyewear model adjustment to optimize parameters;

FIG. 20 is a diagrammatic illustration of the scaling of an anatomical model to a user's face using a double mirror reflection system;

DETAILED DESCRIPTION

Figure 1A:
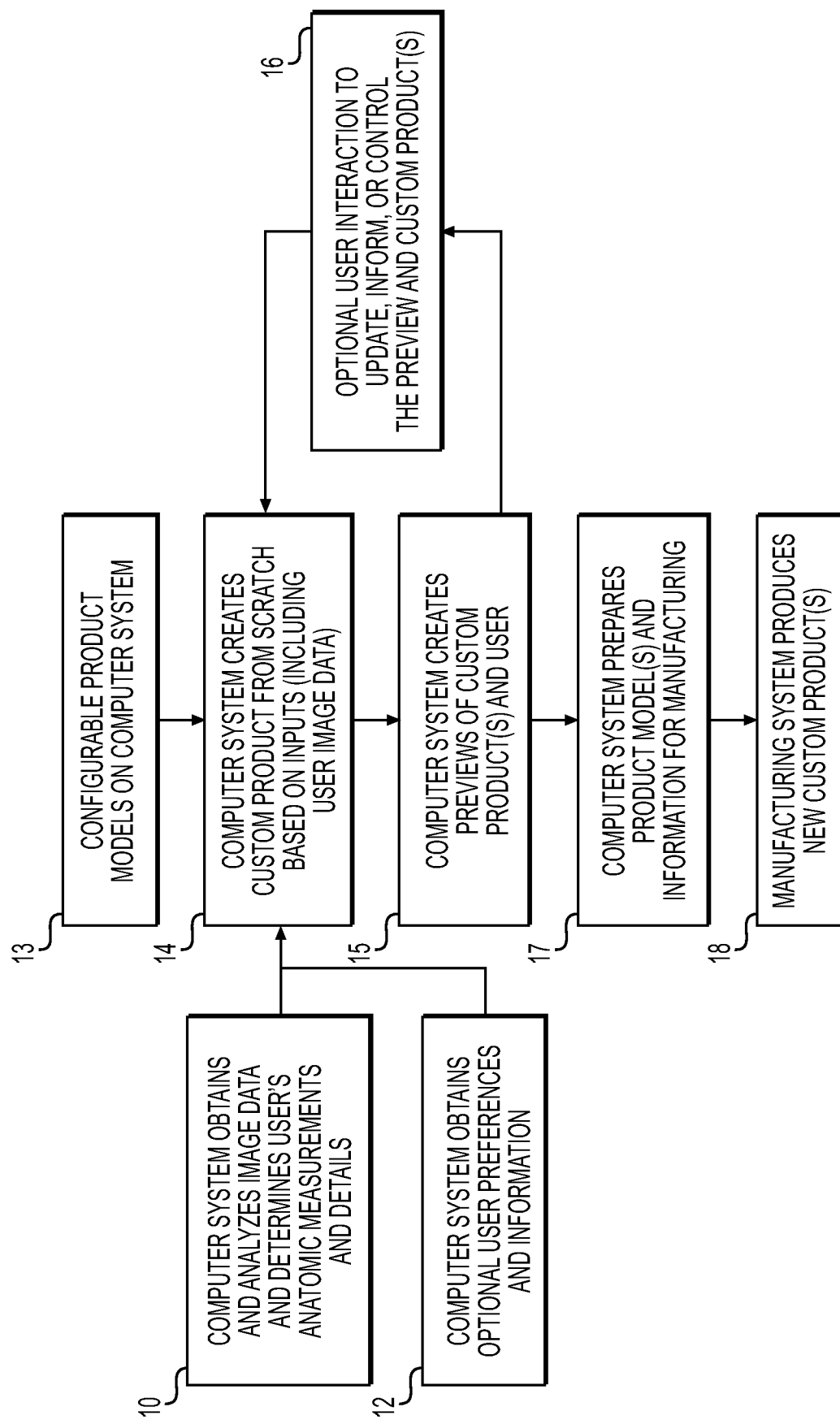
FIG. 1A is a block diagram of a system to create a from-scratch one-up customized product without the exclusive use of off-the-shelf components.

Referring to FIG. 1A, a system is provided in which a computer system 14 creates a custom product from scratch based on inputs to the computer system, including input based on the user image. From scratch refers to the fact that what is provided is a one-up customized product that is manufactured without the exclusive use of off-the-shelf, previously designed, previously produced, or stock components. This does not mean that incidental components such as fasteners, hinges, and the like cannot be available as parts of a custom product. However, the major components of the product are designed ab initio, thus to give the product a new type of uniqueness, unlike that available by products which are assembled from pre-manufactured components.

It is important to understand where the computer system that generates these custom products obtains information. The computer system obtains imaging data of the user, determines anatomic data, measurements from image data, and further optional user preferences and information such as the users likes or dislikes, ascertained from analysis of the users computer history. The computer system also accepts inputs from the user, where the user may specify certain preferences or directly control some aspects of the product customization.

The system does not operated in a vacuum; in other words, the computer system does not generate custom products from nothing. In order for the computer to start its creative process, configurable product models are installed on the computer system that at least specify in some broad outline, structures and specifications that are necessary for the customizable product.

With this having been said, and as illustrated at 10, computer system 14 obtains and analyzes image data and determines a user's anatomic measurements and details. As has been noted hereinbefore, image capture can be accomplished in a variety of different ways, most notably by utilization of a self-portrait generated from a handheld electronic device such as a smart phone or electronic camera. This is a convenient image capture method for the average user who may utilize the ubiquitous cell phone as the point of departure for defining his or her own anatomical features.

The computer system as illustrated at 12, obtains optional user preferences and information which may be gleaned from a wide variety of sources. The computer system at 14 is provided with at least one configurable product model 13 to guide the computer system. Having analyzed all of its inputs, computer system 14 automatically outputs a new custom product model. The output of the computer system 14 is therefore provided to preview system 15 in which the computer system creates previews of custom products and the user. Then, as illustrated at 17, the computer system prepares product models and information for manufacturing the selected one-up, fully-custom product.

Note that it 16. optional user interaction is provided to update, inform, or control the preview, and custom products. After the computer system has created previews of custom product, the user may specify optional user interaction to update, inform, or control the preview, and custom products. When these addition control instructions are input to the computer system 14, the system is able to carry out the optional new directions for the custom product, either directly incorporating user changes or using input to inform new custom product models.

More particularly, the system operates as follows. The computer system obtains the image data at 10 by a variety of means, such as a camera or imaging device connected to the computer system, with image data transferred to the computer system by the user, or image data transferred from another computer system. The anatomic measurements and details may result in dimensions, models, shape analysis, etc, and will be described in further detail.

As illustrated at 12, computer system 14 obtains other optional user information and preferences. This information, such as demographic information, medical or prescription information, answers to questions, style choices, keywords, etc may be used as further inputs to the computer system's automatic analysis and customization of a product for the user.

As illustrated at 13, the computer system contains configurable product models added by the manufacturer or designer. These configurable product models are representations of the custom product, and they may be modified to alter properties including shape, size, color, finish, etc. The configurable models may have thousands, millions, or infinite variation, yet they are also created with the ability to constrain or restrict configurability to a domain that the manufacturer chooses (e.g. only a certain range of material thicknesses may be used or certain dimensions must not change when others are configured). The configurable models may contain sub-components, such as fasteners, that are mass-produced or pre-designed, but the major custom components when assembled with the sub-components results in a highly customized, one-up, from scratch product.

As illustrated at 14, the computer system uses the inputs consisting of the configurable product model, user image data, user anatomic data, and optional user preferences to generate a new custom product model. The computer system may use a variety of techniques, including equations, analytics, shape models, machine learning, clustering, lookup tables, etc to produce a final custom product model. The computer system may also produce a range of custom models for the user to choose from. These custom models are considered one-up, non-stock, and completely custom for the individual user.

As illustrated at 15, the computer system creates a preview of the custom product model. The preview may consist of images of the custom product, renderings of the custom product model on the user's anatomic model, renderings of the custom product model on the user's image data, physical rapid prototypes of the custom product model, etc. The previews may be shown to the user on a display of the computer system.

As illustrated at 16, the computer system accepts user input to update, inform, or control the custom product model. The user, or others given permission by the user, may change the preview, select configurable options of the custom product model such as color or size, answer questions to refine the product model, or the user may directly alter the configurable model to their preferences (i.e. changing the shape or style).

As illustrated at 17, the computer system prepares the custom product approved by the user for manufacturing. Preparation may involve converting the custom product model and user preferences to a set of specifications, instructions, data-structures, computer-numerical-control instructions, 2D or 3D model files that can be interpreted by manufacturing systems, etc. Preparation may also include custom computer-controlled instructions for guiding machinery or people through each step of the manufacturing process.

As illustrated at 18, the computer system provides instructions to a manufacturing system, which produces the one-up custom product. Various specific methods will be described for producing a one-up custom product.

The previously mentioned computer and manufacturing system are described generally in FIG. 2 as a block diagram of computer system 220 used by a user 200. In an exemplary embodiment, at least one computer system 220, including but not limited to a tablet, phone, desktop, laptop, kiosk, or wearable computer, is configured with a display 230 for presenting image data to a user. The display 230 includes LCD screens, flexible screens, projection, 3D displays, heads-up displays, or other display technologies. The computer system 220 has an input device for controlling the computer system, included but not limited to a touchscreen, keyboard, mouse, track pad, or gesture sensor. The computer system 220 is further configured with an image capture device 210, including but not limited to a single-lens camera, video camera, multi-lens camera, IR camera, laser scanner, interferometer, etc. The image capture device is henceforth referred to as "camera". The computer system 220 is further configured to connect to a network or other systems for communicating and transferring data 240. The computer system 220 is configured to connect to other computer system(s) 250, including but not limited to servers, remote computers, etc. The other computer system(s) 250 is connected to or in control of the manufacturing system 260. The computer system 220 is further configured to provide an interface to the user 200 for viewing, customizing, shopping, and ordering custom products.

In addition to the custom product system for creating custom products based on user image data, anatomy, and preferences, the subject invention describes shopping systems that allow a user to gain access to the custom product system: a means to shop, order, browse, interact, provide payment, etc. One embodiment for a custom eyewear shopping system, which is built around the custom product system, is described:

Custom Eyewear Shopping System

Figure 1B:
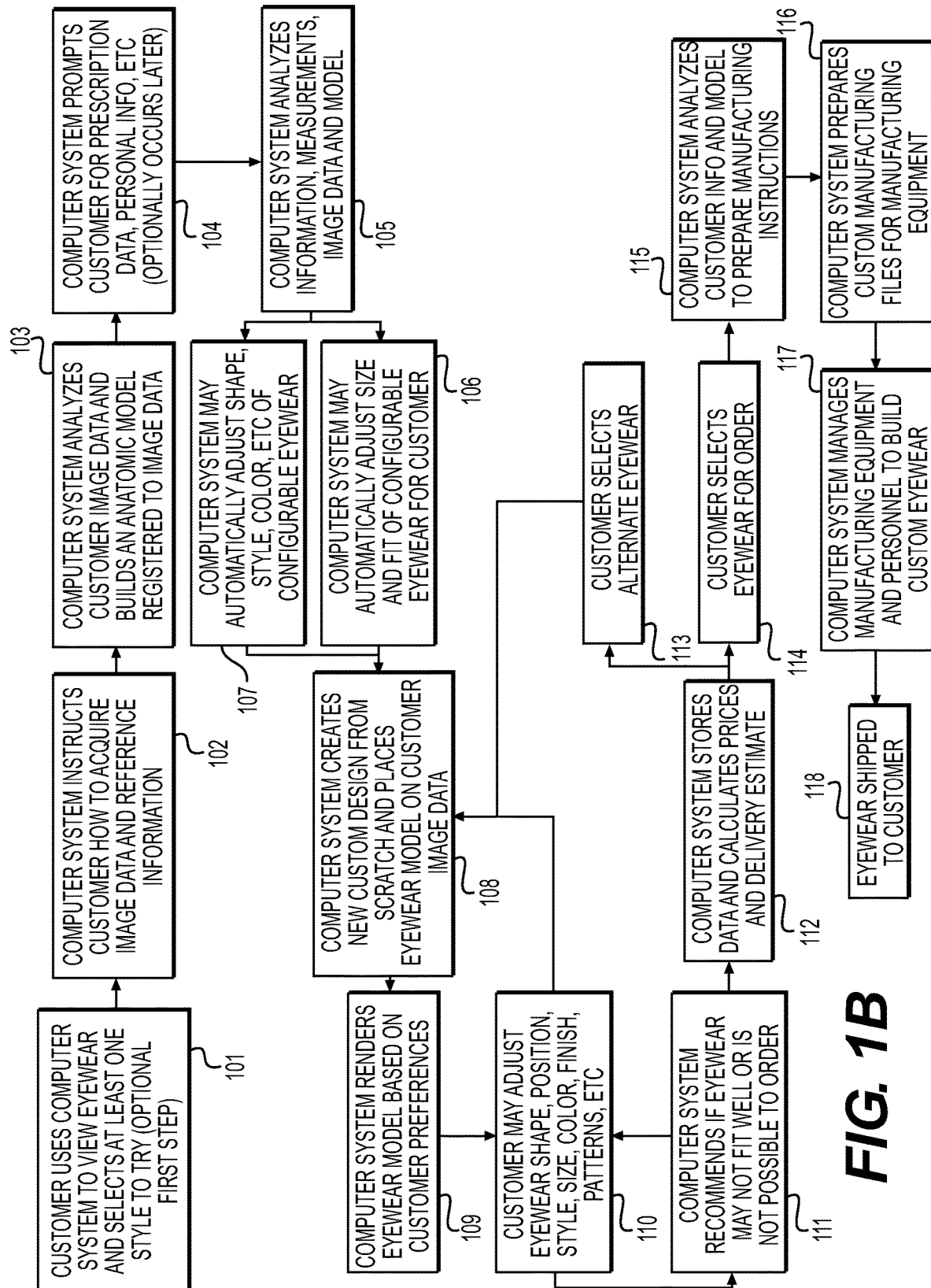
FIG. 1B is a block diagram of a custom eyewear shopping system.

Referring to FIG. 1B, a system for ordering custom one-up eyewear that is created from scratch is detailed. As illustrated at 101 a user uses a computer system to view eyewear and selects at least one style to try. This first step is optional, and the user may view a plurality of eyewear on the computer display and choose to preview any of a plurality of eyewear. The user may select styles to try and preview at the beginning of their shopping experience, prior to purchasing, or at any time they choose. As illustrated at 102 the computer system instructs the user how to acquire image data and reference information. The computer system camera captures image data consisting of one or more images, videos, or live previews of the user, and the computer system display shows the image data through its display. As seen at 103 the computer system analyzes computer image data and builds an anatomic model registered to image data. Thereafter, as illustrated at 104 the computer system prompts a user for prescription data, personal data and other information, which may be optionally entered at a later step. This is followed as illustrated at 105 by the computer system analyzing the input information: measurements, anatomic model, user preferences, and image data. As illustrated at 106, the computer system automatically adjusts size and fit of eyewear for the user. Additionally, as illustrated at 107, the computer system may automatically recommends shape, style, and color choices to a user. As illustrated at step 108, the computer system creates at least one new custom eyewear model with at least one component designed from scratch and automatically places the eyewear model on user image data. The computer system renders a preview the custom eyewear model, which may include lenses, as illustrated at 109. The rendering may include combinations of the user image data and user anatomic model with the custom eyewear model, as previously described.

As illustrated at 110, the user may interact with the computer system to adjust at least one of the eyewear size, shape, position, style, color, finish and patterns, etc. The result is illustrated at 111 in which the computer system recommends if the eyewear may not fit well or is not possible to order based on the user interaction.

Thereafter as illustrated 112 the computer system stores the data and calculates price and delivery estimates and any other relevant information the customer needs to decide whether to place an order or not. As illustrated 113 the user may select alternate eyewear or the user selects the custom eyewear to order as illustrated 114.

If the user selects alternate eyewear as illustrated at 113 the computer system automatically generates a new custom eyewear model as illustrated at 108 and the process begins again.

Once the user selects the eyewear for an order, as illustrated at 114 the computer system analyzes user information and models and prepares manufacturing instructions, and as illustrated at 115 the computer system prepares custom manufacturing files for the manufacturing equipment. Thereafter the computer system manages the manufacturing equipment and personnel to build the custom eyewear as illustrated 116. Finally the eyewear is shipped to the user as illustrated at 117. This completes the custom eyewear product, which was created and manufactured from scratch for the user.

The following sections will describe further detail of the key steps involved in creating a one-up custom product for a user:

Obtaining and Analyzing Image Data and Anatomic Information

The following section describes the detailed system and method for obtaining and analyzing image data and anatomic information, which is illustrated in FIG. 1A at step 10 and 1B at 102, 103, and 105.

Figure 3:
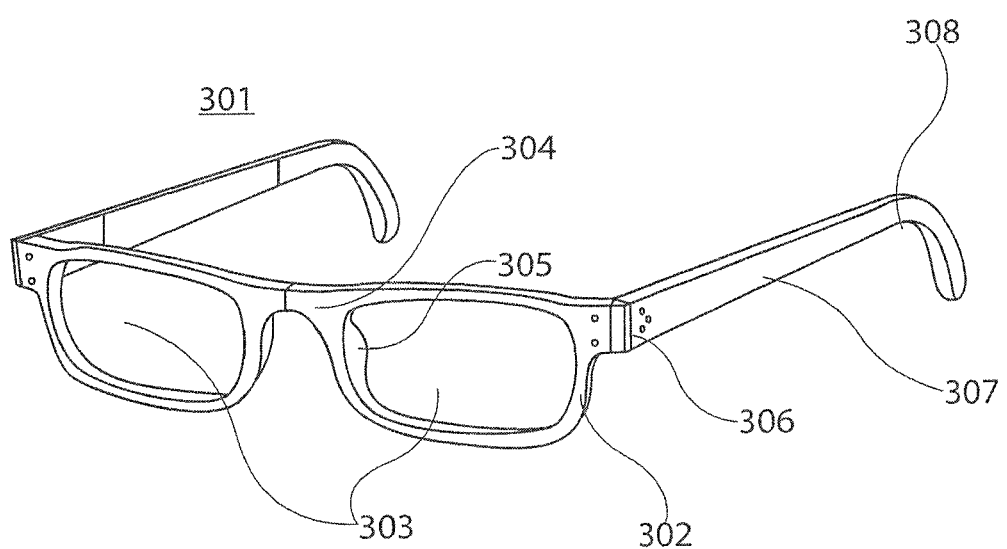
FIG. 3 is a diagrammatic illustration of eyewear and eyewear parts which can be customized through the use of the subject system.

Before describing the detailed method for obtaining and analyzing image data and anatomic information, face anatomy and eyewear terminology are described for reference. FIG. 3 shows eyewear 301, with various parts of the eyewear labeled. The front frame 302 holds the lenses 303 in place. The bridge 304 is in the center of the front frame 302, and the nose pads 305 extend off the front frame 302 to hold the eyewear 301 on the nose of the wearer. The hinges 306 connect the front frame 302 to the temples 307, which rest on the tops of the wearer's ears at feature 308. FIG. 3 represents only one eyewear design, and it should be recognized that these basic parts may apply to other eyewear designs, or that some eyewear designs may have different parts.

Figure 4:
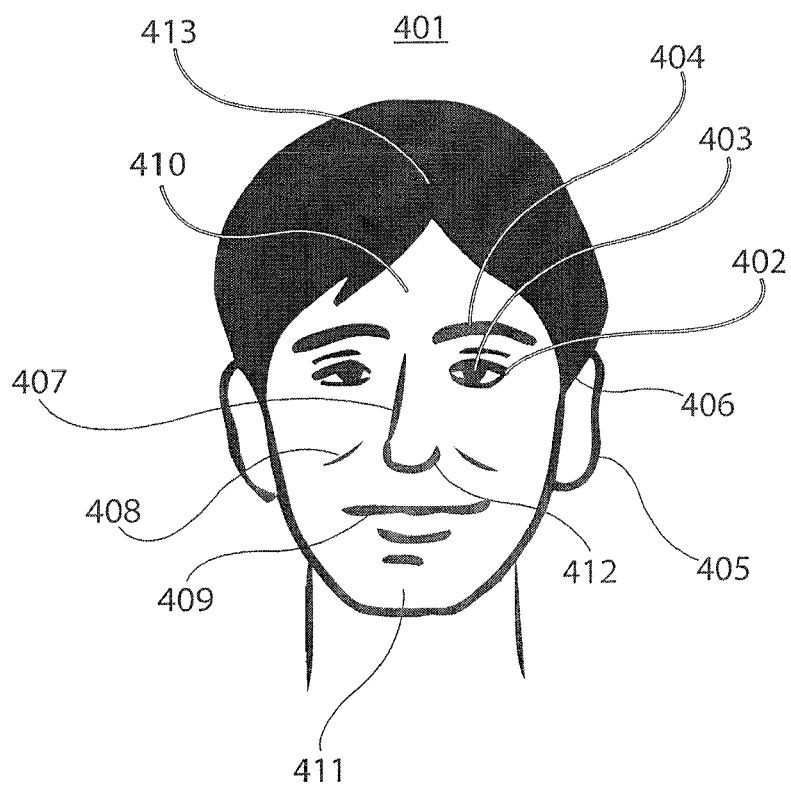
FIG. 4 is a diagrammatic illustration of a user's face and anatomic features.

FIG. 4 shows a user's face 401, eye 402, pupil 403 at the center of eye 402, and eyebrow 404. The ear 405 also has a location denoted as the top of ear 406, where the temple of the eyewear would rest. The nose 407 is essential for support of eyewear. Cheekbones 408, mouth 409, forehead 410, chin/jaw 411, nostril 412, and hair 413 are other features of importance in detecting and analyzing quantitative anatomic models.

Acquisition of Image Data

Figure 5:
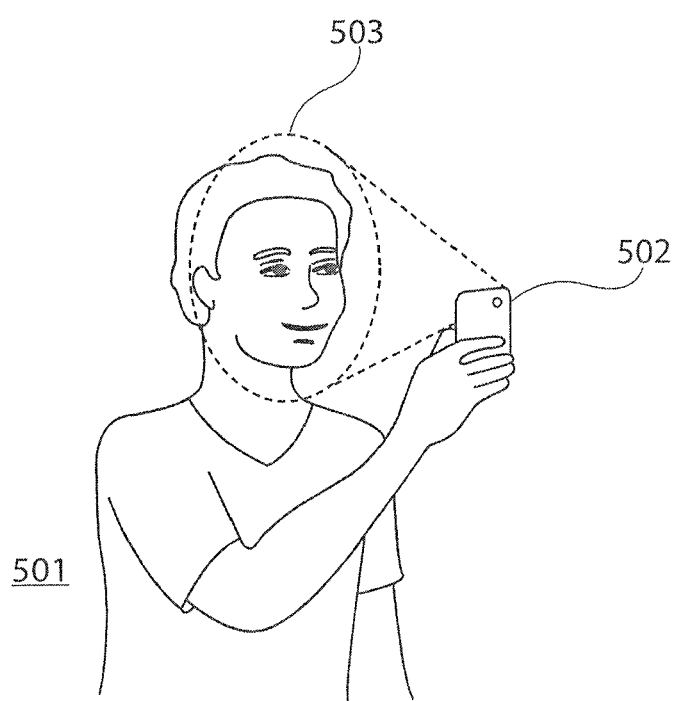
FIG. 5 is a diagrammatic illustration of a computer system to capture image data.

FIG. 5 shows a user 501 using a computer device 502 to acquire image data of their face 503. Instructions are provided to the user to place their face in certain positions while the computer system captures and analyzes image data of the user's face. The computer system may utilize a smart phone or handheld electronic camera for the capture of the image of the person's face. As mentioned hereinbefore, there is sufficient information from a single camera view of an individual to permit 3D modeling, and more particularly the generation of an anatomic model.

The computer system may require that certain objects are present in the image to provide reference of scale. It is important to ensure the dimensions of the eyewear are appropriately sized relative to the user's face, and providing dimensions to the image data or the resulting anatomic model and measurements is needed to ensure accurate sizing. Reference objects may include but are not limited to: coins, rulers, sheets of paper, credit cards, computer disks, electrical or computer connectors, stamps, a calibration target on a computer device, or the computer device itself. The objects, when positioned near the user's face, provide a reference dimension for the system to set dimensions to the image data. If other image technology is available, such as a depth camera, or if shape model techniques with intrinsic dimensions are used then reference objects may not be needed since the scale of the image data could be determined by the imaging equipment or shape model.

In an exemplary embodiment, once the user has followed instructions and is positioned in front of the computer system's imaging device, acquisition and analysis of their data begin. A first reference image is captured with a reference object held by the user in the same field as their face. The image data captured by the computer is analyzed by the computer system to detect the reference object and measure its size, for example in pixels. The image data is further analyzed by the computer system to detect one or more of a plurality of features, including but not limited to pupils, eyes, nose, mouth, ears, face, eyebrows, hair, etc. In an exemplary embodiment, the user's pupils are detected, and landmarks placed on the center of each pupil. In another embodiment, the user may optionally be queried to confirm or edit the location of each pupil marker to ensure accuracy. With the data previously analyzed from the reference object the distance in pixels between pupils or other features is scaled from pixels to a unit of distance such as millimeters or inches. In another embodiment, the user may have previously acquired data on a dimension(s) of their face, such as pupillary distance obtained from an optometrist or an optical test, and the user may enter this data into the computer system in lieu of using a reference object for scale. Alternatively, the reference image is acquired later in the process or at the same time as other image data acquisition.

The purpose of scaling the data with a reference object is to ensure that measurements can be derived from the final quantitative anatomic model of the user. There are several key measurements to best determine how to virtually place and fit eyewear on an image of a user's face.

Figure 6:
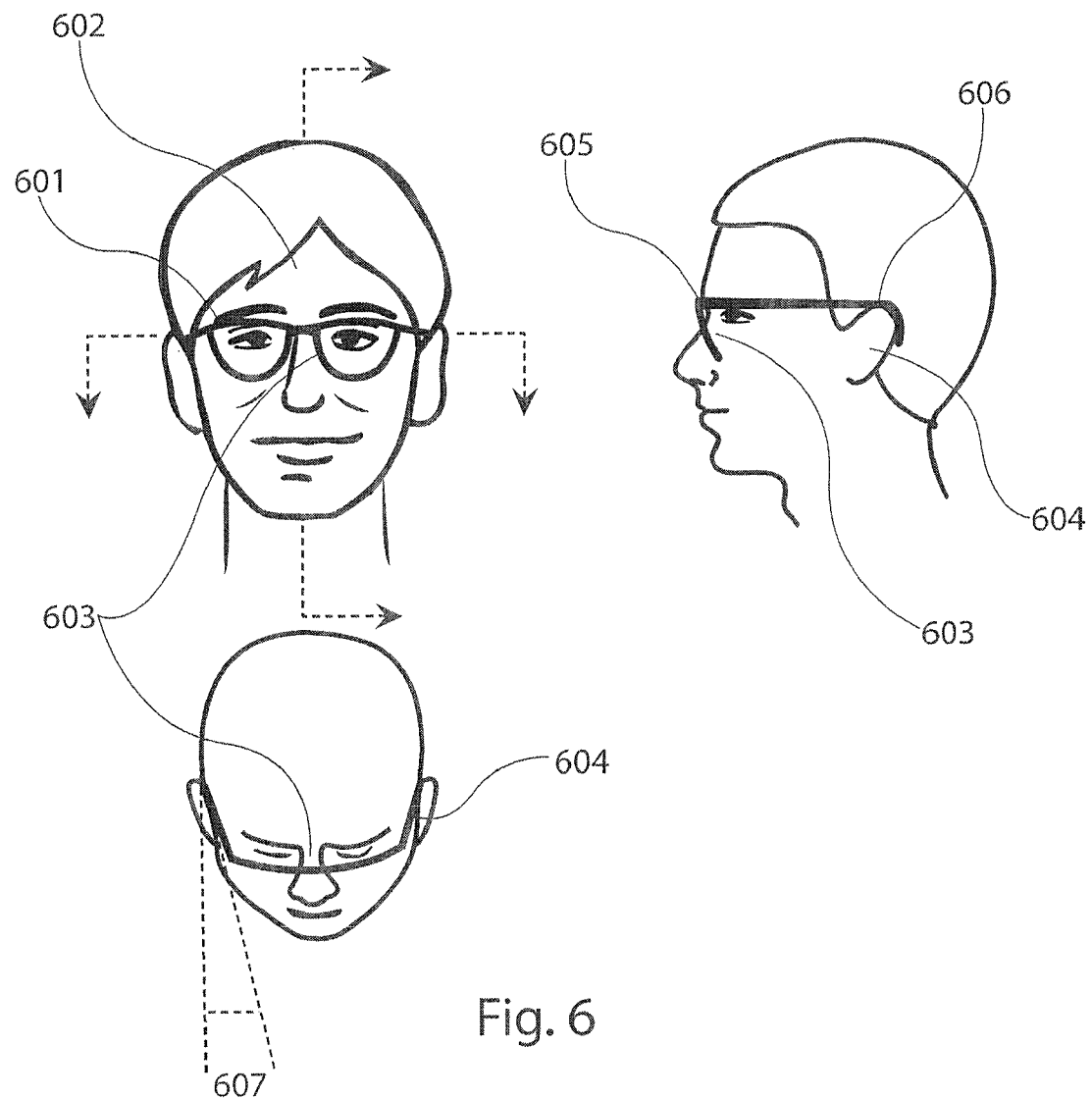
FIG. 6 is a diagrammatic illustration of dimensions between a face and eyewear for analyzing a face, thereby to permit further facial and eyewear parameters.

FIG. 6 shows an illustration of the relationship between eyewear 601 and a user's face 602. The locations where the eyewear and face contact are of high importance since they control the fit of the eyewear. The contact locations between the eyewear 601 and the user's nose 603 are shown. Also shown are the contact locations between the eyewear 601 and the user's ears 604, as well as the height and length between the top of the eyewear 605 and top of the ear 606.

Figure 7:
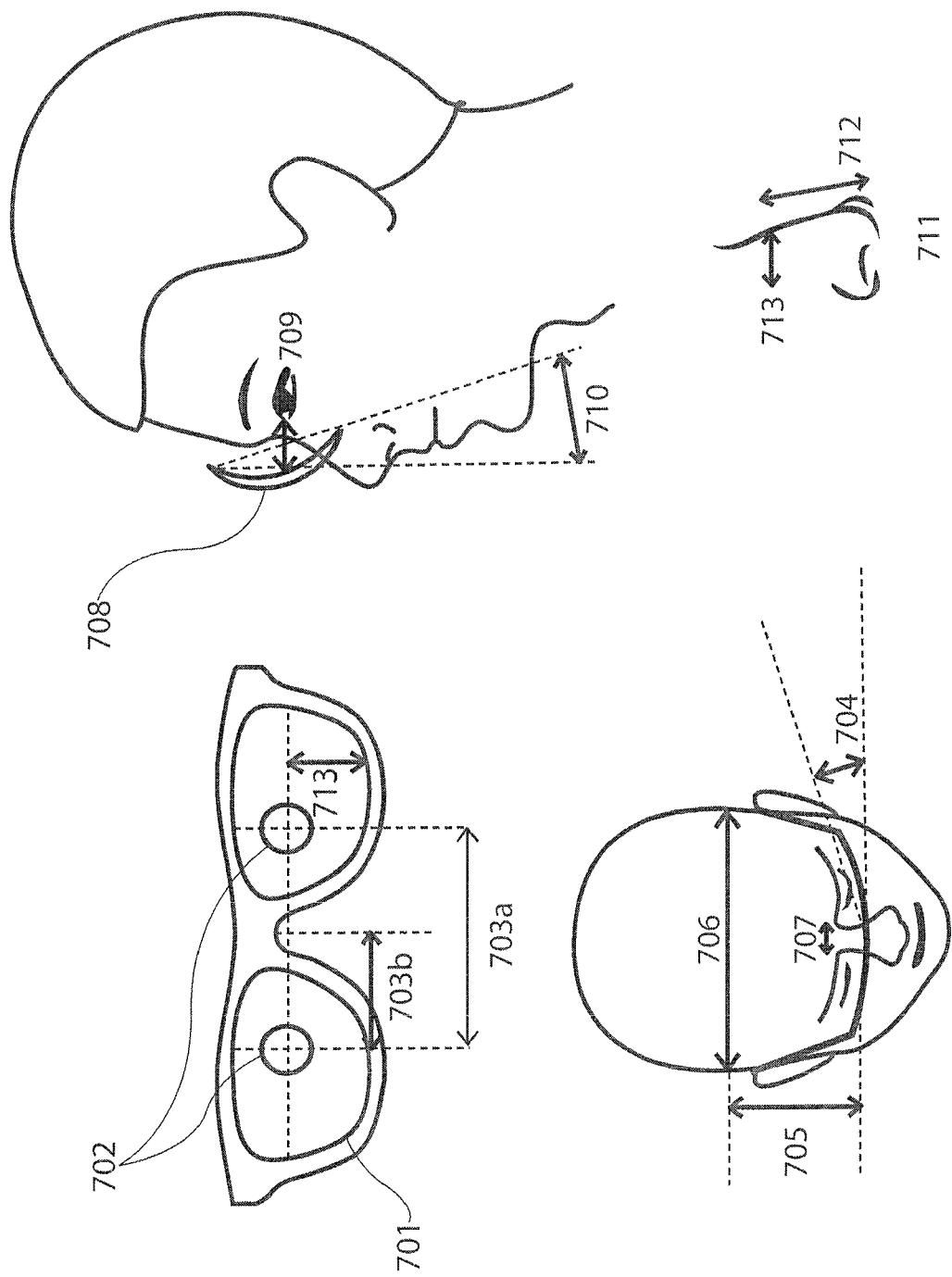
FIG. 7 is a diagrammatic illustration of additional dimensions of faces and eyewear.

As to FIG. 7, various detailed eyewear measurements are illustrated. FIG. 7 shows eyewear 701 with binocular interpupillary distance (Pd) 703a between pupils 702 and monocular interpupillary distance 703b between the center of the nose and pupil 702. Furthermore, if the highest quality optics are desired, or if specialized optics such as progressive lenses are desired, then additional measurements relating the eyes and optics are useful, such as vertex distance 709 (distance from the eyes to the lens), pantoscopic tilt angle 710 (angle of the lens to the front of the face), face or frame wrap 704 (curvature of frame around face), lens height 713 (vertical location of pupils in the lens), or optical center. Prior art, as previously described, has been limited in not generating and using a wealth of information available from a full quantitative anatomic model of a user's face in order to fully customize eyewear frames and optics, as well as enable the best eyewear shopping interface and experience.

By way of example, FIG. 7 also shows the distance between nosepads of the eyewear 707. In this regard, FIG. 7 shows a model of a nose 711, which is used to derive quantitative measurements, including by not limited to its length 712 and width 713 at various locations. Since each user's nose varies in dimensions, there is a great advantage in being able to precisely measure its size and shape and then custom fit eyewear to perfectly fit that anatomy. Optimum comfort of an eyewear's nose pads positioned on a user's nose is achieved if the two contact surfaces are aligned properly and mate such that there are no high pressure-points and if the eyewear is naturally supported in the proper position by the nose. Each user may have a unique preference as to where on his nose he prefers to wear his eyewear for maximum comfort, aesthetic, or utility. Also, nose structure/shapes vary considerably between ethnicities. For example, users of Asian descent have noses with a smaller and flatter bridge than the noses of Caucasians, and they often prefer glasses that are designed specific to their population. However, a distinct advantage exists in not designing for a population, but rather designing for an individual user and their unique anatomic structure. Understanding the quantitative anatomy of the nose allows a custom eyewear to sit precisely on the nose where desired with maximum comfort, aesthetic, and utility achieved out-of-the box without need for subsequent adjustment, which is often performed by an optical professional. However, proper adjustments post-hoc of eyewear features such as nose pads, particularly on plastic frames, is impossible for many eyewear designs.

FIG. 7 also shows additional measurements of the length of the temples 705 and distance between the temples 706 needed to achieve a fit with the user's face. Further, the brow, cheekbones, length of nose, and width of the head may provide limitations of where eyewear could fit on a user's face. Other dimensions of the face, such as the shape of head, curvatures, the length, shape, and angle of the nose, and more is used to help suggest the best eyewear style and shape for a particular user. The locations of the pupils relative to eyewear are important to ensure good optical quality.

In an exemplary embodiment, the computer system instructs the user to position and move their head while the camera captures a series of images, or video. The rotation is side-to-side, up and down, or a combination. The computer system instructs the user to move their head to precise locations or just request that they approximate a movement shown on to them on the display. In another embodiment, the user has a handheld computer system and moves the camera around their head rather than rotating their head. In another embodiment, the user already has images or videos to upload to the system, or the user captures images or videos with another imaging device and uploads them to the computer system, in lieu of capturing these with the computer system.

The captured video may consist of a series of images of the user's face at various angles making up a set of image data. The computer system may perform analysis on the images immediately as they are captured to provide feedback to the user if there is a problem or if insufficient image quality, poses, or quantity of data is acquired.

In an exemplary embodiment, the computer system analyzes the image data to ensure the user's face remains approximately within the center of the frame within certain bounds. The computer system may run a face detection algorithm on the image data to detect the boundary of the face within each image. If the computer system detects the face outside the bounds, interference or occlusion detected in front of the user's face, or excessive blur or other unacceptable acquisition artifacts, then the user is provided with a warning and instructions on how to re-acquire a new set of image data. Additionally, the computer system crops or excludes portions of the image data before performing more intensive computations on the remaining dataset in order to reduce computation and/or transmission time. For example, the computer system may crop any part of the image that is outside of the bounds of the detected face. In addition to detecting the face, the computer system may estimate the pose of the face (degree of rotation). The pose is estimated by using various face detector or classifier algorithms that are trained to determine poses. With a pose estimate for each image, the computer system determines if an adequate range of poses have been captured. If not, the computer system may instruct the user to reacquire. The computer system may also filter unnecessary images. For example, there may be duplicate poses or a small number of unacceptable images that fall below a threshold for quality. Rather than reject the entire set of images, the computer system may reject a certain number of unacceptable images and only process the images that pass the quality threshold, which is based on the previously described metrics.

The computer system automatically, or with user input, identifies the precise image capture device and subsequently uses that understanding of its optics to correct for optical distortions or utilize knowledge of the lens' depth-of-field to better analyze the dataset. Depending on the image capture device, the computer system also corrects for distortions or imperfections, such as lens barrel distortion observed on wide-angle lenses. These corrections enable the image data acquired to best represent the user.

Quantitative Anatomic Model

Referring back to FIG. 1A at 10 and FIG. 1B at 103, the method describes the construction of a quantitative anatomic model of at least a portion of the user's face and head. Once a complete set of image data is acquired, the computer system analyzes the image data to construct a quantitative anatomic model of the user's face. Various techniques are used to construct the model, and in an exemplary embodiment a quantitative anatomic model is represented as a surface mesh made of elements, including but not limited to polygons, curvilinear elements, etc.

Figure 8:
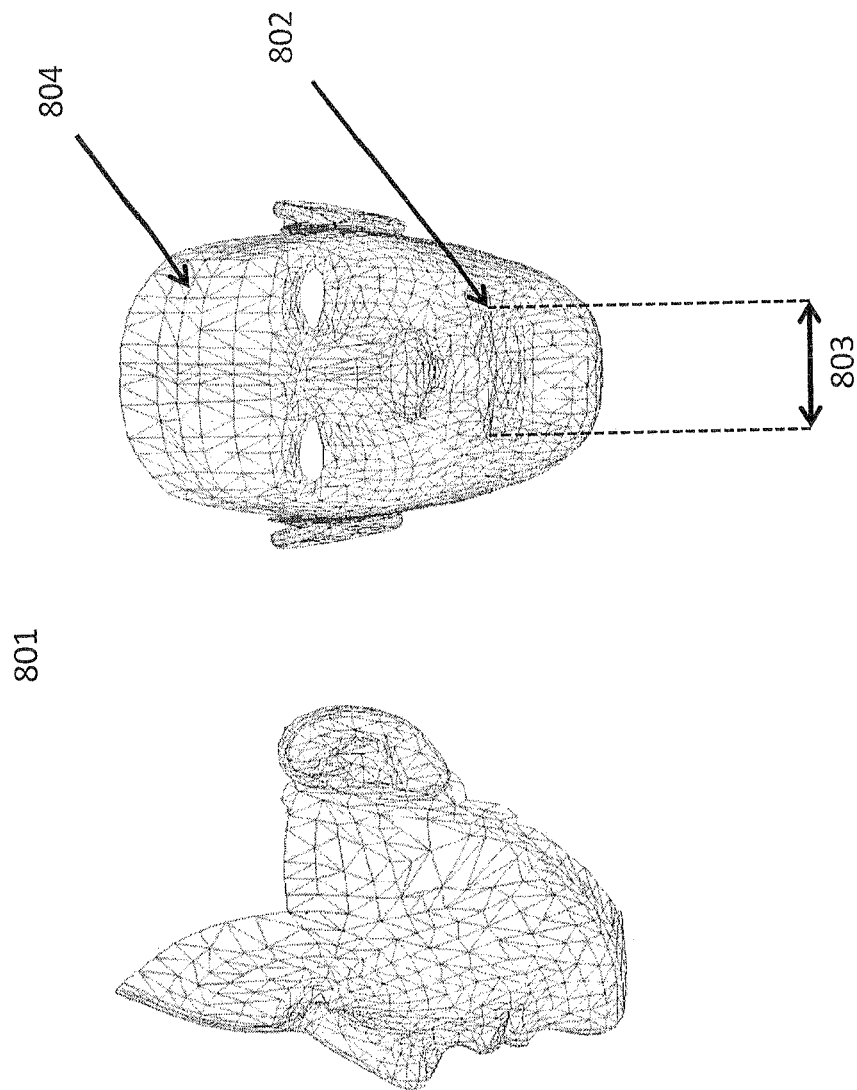
FIG. 8 is a diagrammatic representation of a parameterized quantitative anatomic model.

FIG. 8 shows an example of a mesh 804. The resolution of the mesh is altered based on curvature, location, and features on the face, etc. For example, the detailed locations around the eyes and nose are higher resolution than areas where less detail exists, such as the top of the head. In an exemplary embodiment, the face mesh only models the front and side face area, though in other embodiments it models the entire head or any portion thereof that is necessary including smaller regions of the face, such as the eyes and nose only. Alternative representations include point clouds, distance maps, image volumes, or vectors.

In an exemplary embodiment, a generalized quantitative anatomic model is distorted to fit the user's face. The model is parameterized and represented as a mesh, with various mesh points affected by adjusting parameters. FIG. 8 shows an example of a model 801, with mesh elements 804. In this example, a parameter influences the length 803 of the mouth feature 802. If the parameter influencing length 803 were adjusted, then the appropriate elements of the mouth would adjust coordinates in order to match the parameter specified. Other models, such as a shape model, may have generalized parameters like principal components that do not correspond to particular features but allow the generalized anatomic model to be adapted to a plurality of different face sizes and shapes.

The computer system analyzes the image data to iteratively perform a sequence of feature detection, pose estimation, alignment, and model parameter adjustment. A face detection and pose estimation algorithm is used to determine a general position and direction the face is pointing toward, which aids in model position and alignment. Machine learning methods are used to train a classifier for detecting a face as well as determining the pose of the head in an image that is post-processed to define various features, including but not limited to Haar-Like or Local Binary. Training datasets consists of images of faces in various poses that are annotated with the location of the face and direction of pose, and also includes specific facial features. The output consists of a location of the face in an image and a vector of the direction of head orientation, or pose.

Once the face and pose are established for the first image frame, an iterative process begins where more detailed facial features relevant to eyewear placement and general face geometry are defined, including but not limited to eye location, nose location and shape, ear location, top of ear location, mouth corner location, chin location, face edges, etc. Again, machine learning is used to analyze the image to detect facial features and edges. When these features are located, the generalized quantitative anatomic model parameters is aligned and adjusted to find the optimal fit with the features, minimizing the error between the detected feature location and the mesh. Additional optimization of the generalized quantitative anatomic model may be performed to enhance the local refinement of the model using the texture information in the image.

In an exemplary embodiment, the generalized quantitative anatomic model has parameters that influence features including but not limited to eye location, eye size, face width, cheekbone structure, ear location, ear size, brow size, brow position, nose location, nose width and length and curvature, feminine/masculine shapes, age, etc. An estimation of the error between the detected features and model is used to quantify convergence of the optimization. Small changes between adjacent images in the dataset are also used to refine pose estimation and alignment of the model with the image data. The process iterates to subsequent image frames.

In an exemplary embodiment, features detected from adjacent image frames are used to initialize subsequent or previous frames to enhance feature detection. The process continues through as many images as needed and possibly cycle through images multiple times to converge on the optimal parameters to minimize error between the distorted generalized model and the image data. Regularization and smoothing may be employed to minimize noise and variance of features points, pose, and the anatomic model fitting between frames. The final quantitative anatomic model will be scaled based on the reference data such as input from the user or scaling to a reference object as previously described. Alternatively, if the anatomic model was derived as a shape model in real-world dimensions, the association between the shape and size of the face may be used to directly provide the scale of the model.

Since the model was refined through a series of images, the orientation and geometric relationship between the model and image data is known. A bundle adjustment of the features points and face model across the images may be performed, which provides precise camera locations that register the anatomic model to the image data. This information can be used to orient and register the model to the image data for subsequent rendering.

Those skilled in the art will recognize there are many ways to construct and represent quantitative information from a set of image data. In another embodiment, no prior generalized anatomy model is required to generate a quantitative anatomic model. A method such as structure from motion (SFM) photogrammetry is used to directly build a quantitative anatomic model. In this technique, a series of images is required around the user's face. The features detected in each image, and the relative distances between the features from image-to-image are used to construct a 3D representation. A method that combines a generalized shape model with subsequent local SFM refinement may be utilized to enhance local detail of features, such as the nose shape.

In another embodiment, the quantitative anatomic model consists only of a point cloud of key features that are detected. For example, the center of the eyes, corners of the eyes, tip of the nose, top of the ears, and other important landmarks is detected and tracked through multiple images. These simple points, oriented in space in a dataset, provide all the information needed to obtain quantitative information needed for subsequent analyses. They may be obtained using the methods previously mentioned, or with other methods like active appearance models or active shape models.

Technologies such as depth cameras or laser sensors may be used to acquire the image data, and there exists prior art describing how these technologies can directly produce 3D models, essentially like a 3D scanner, by their ability to detect distance. Additionally, the use of out of focus areas or the parallax between adjacent images is used to estimate depth.

Alternatively, the quantitative anatomic model and dimensions can be derived from a pre-existing model of the user's face that they possess. Models may be acquired from 3D scanning systems or imaging devices. If a user already has an anatomic model their face, they may digitally transfer it to the computer system by non-transitory computer readable media, a network connection, or other means.

Figure 17:
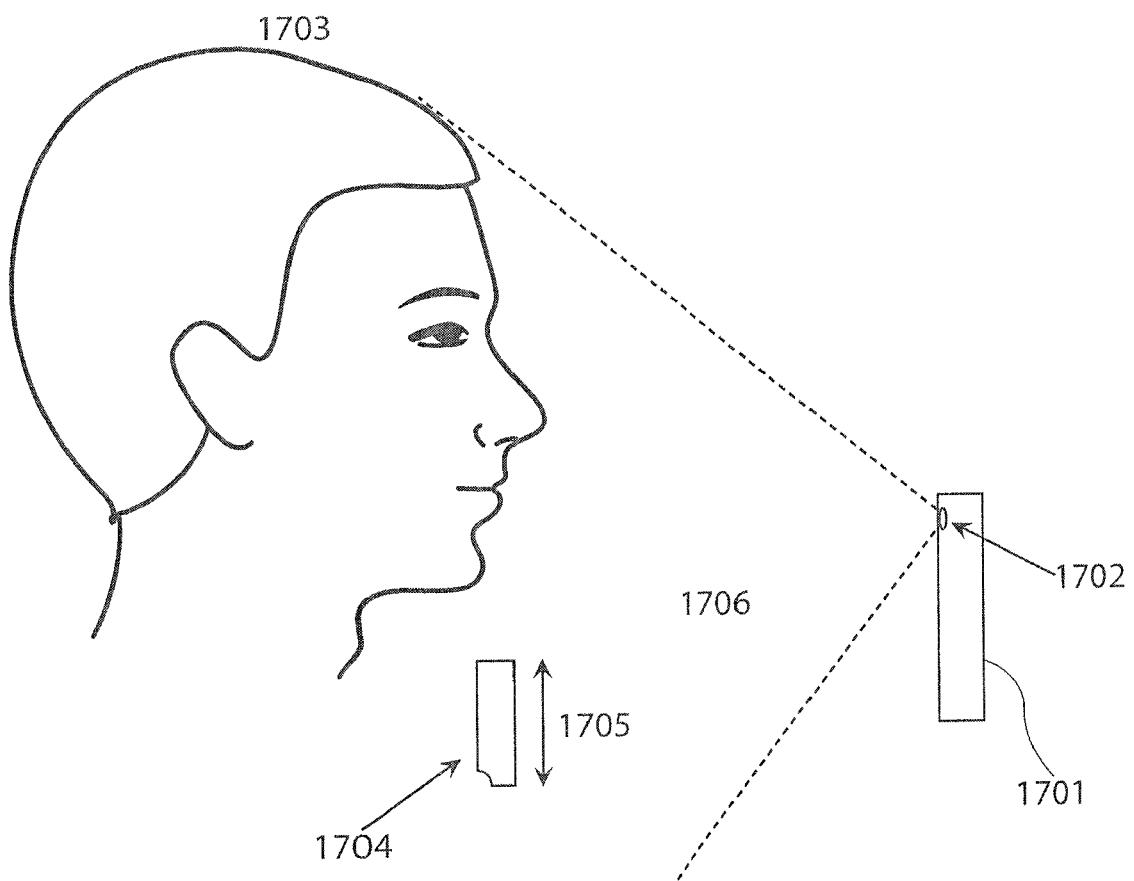
FIG. 17 is a diagrammatic illustration of a computer with an imaging device to acquire the image of the user utilizing a reference.
Figure 18:
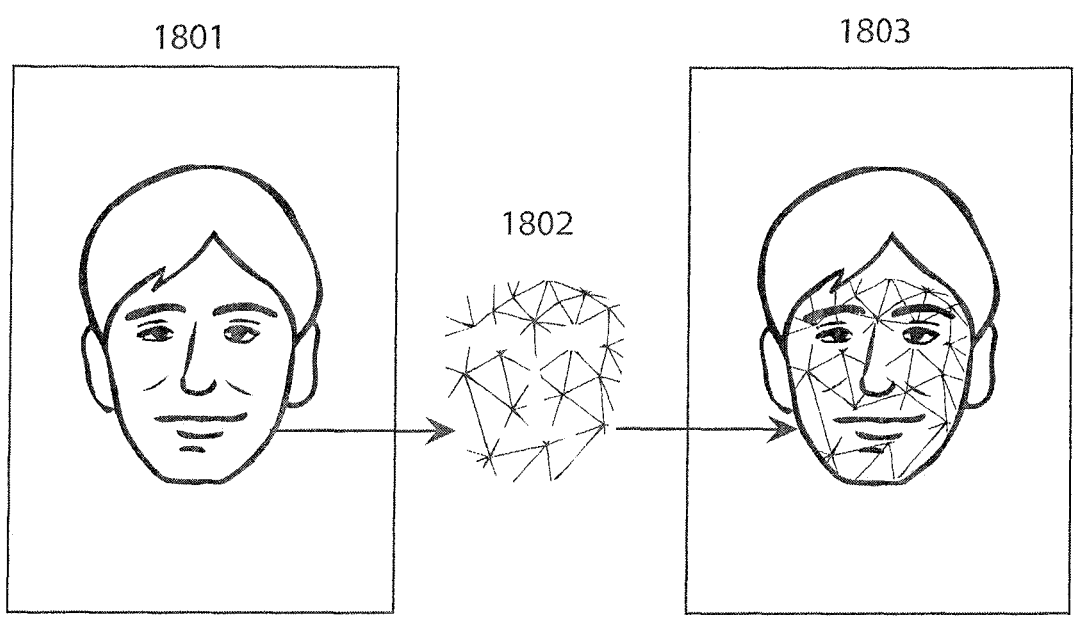
FIG. 18 is a diagrammatic illustration of a computer system to co-register an anatomic model with an original user image.

During acquisition of user image data for customizing products, such as eyewear, the scale and dimensions of the user are important to ensure that the size of the resulting product is appropriate and that the user receives a product that matches the previewed version. The following embodiments describe various systems and methods for acquiring, scaling, and reconstructing anatomic models from image data:

Embodiment to Scale an Anatomic Model of a User's Face with a Reference Target Present in Multiple Images Referring now to FIG. 17, as to this embodiment, a) A computer system 1701 is configured with a camera or imaging device 1702 used to acquire image data of a user 1703; b) A reference target 1704 of known dimensions (eg coin, credit card, phone, tablet, screen, paper, ruler, etc,) is positioned such that it is visible in at least some images of the user; c) The reference target has at least one predetermined dimension 1705 (eg, diameter of a coin); d) The computer system reconstructs an anatomic model of the user's face based on the image data; e) The computer system detects the reference target in at least some images, including detection of the at least one predetermined dimension; f) The computer system co-registers the anatomic model with the original user images such that the model coordinates and camera position align the face model with the pose, position, and scale of the images of the user's face 1703; g) The computer system uses the ratio of the detected target dimension(s) and the known dimensions of the reference target in each image to set a scaling factor to the dimensions of the anatomic model and h) The computer system may additionally average or weight the measured dimensions of multiple predetermined dimensions of the reference target(s) in each frame in order to reduce error from any single dimensional measurement.

Embodiment to Scale an Anatomic Model of a User's Face with a Reference Target Present in Only One Image In this embodiment, a) A computer system configured with a camera or imaging device is used to acquire image data of a user; b) A computer system configured with a camera or imaging device is used to acquire a separate image of a user with a reference target of known dimensions present in the image; c) The reference target has at least one predetermined dimension (eg, diameter of a coin); d) The computer system reconstructs an anatomic model of the user's face based on the image data; e) The computer system co-registers the anatomic model with the user's image containing a reference target such that the model coordinates and camera position align the face model with the pose, position, and scale of the image of the user's face; and f) The computer system uses the ratio of the detected target dimension and the known dimensions of the reference target in the image to set a scaling factor to the dimensions of the face model.

Embodiment to Scale Image Data that an Anatomic Model of a User's Face is Constructed From In this embodiment, a) A computer system configured with a camera or imaging device is used to acquire image data of a user; b) A reference target of known dimensions (eg coin, credit card, phone, tablet, screen, paper, ruler, etc,) is positioned such that it is visible in at least some images of the user; c) The reference target has at least one predetermined dimension (eg, diameter of a coin); d) The computer system detects the reference target in at least one image, including detection of the at least one predetermined dimension; e) The computer system uses the ratio of the detected dimension and the predetermined size of the object to set a scaling factor to image data (e.g. to apply dimensions to the size of pixels); and, f) The computer system reconstructs a anatomic model of the user's face based on the image data, with the model assuming the underlying dimensions of the images

Embodiment to Scale an Anatomic Model of a User's Face with a Reference Target Included in the Model An advantage of this embodiment is that the orientation and position of the reference target with respect to the user's face is not as important since it will be reconstructed with a model.

Figure 19:
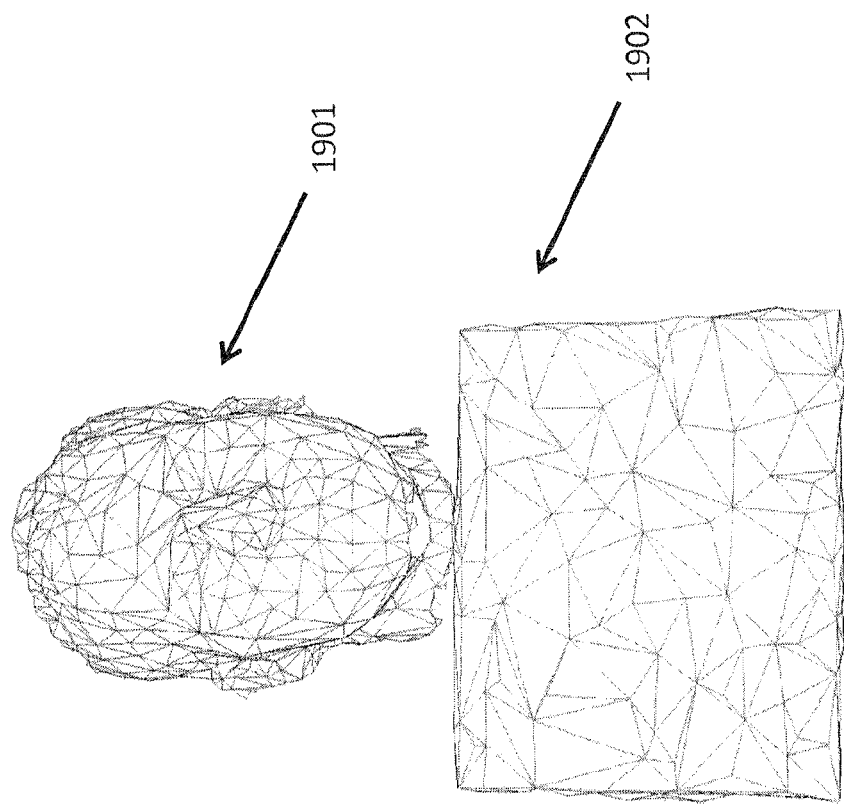
FIG. 19 is a diagrammatic illustration of the use of the computer system to reconstruct a model of a user's face and a model of a reference target based on image data.

Referring to FIG. 19, in this embodiment a) A computer system configured with a camera or imaging device is used to acquire image data of a user; b) A reference target of known dimensions (eg coin, credit card, phone, tablet, screen, paper, ruler, etc,) is positioned such that it is visible in at least some images of the user; c) The reference target has at least one predetermined dimension (eg, diameter of a coin); d) As shown in FIG. 19, the computer system reconstructs a model (or models) of the user's face 1901 and the reference target 1902 based on the image data where the face and target may or may not be in contact with each other, so there are two models positioned in space relative to one another; e) The computer system detects the reference target in the model, including detection of at least one predetermined dimension; f) The computer system uses the ratio of the detected dimension of the reference target in the model and the predetermined size of the target to set a scaling factor to overall model; and g) Optionally, the computer system removes the reference target from the model after scaling, leaving only the final scaled face model.

Embodiment to Scale an Anatomic Model of a User's Face with Pupillary Distance (Pd) Input by a User In this embodiment, users commonly have Pd measured by their optometrist, which provides a reference dimension to scale the head with. How this is done is as follows: a) A computer system configured with a camera or imaging device is used to acquire image data of a user; b) The computer system reconstructs an anatomic model of the user's face based on the image data; c) The computer system detects eye features of the user (pupils, irises, etc) in the face model and measure the distance between the eye features; d) Before, after, or during the image acquisition and reconstruction process, the user provides their Pd measurement; and, e) The computer system uses the users Pd measurement to set a scaling factor to the dimensions of the model, adjusting the size of the model such that the measured eye distance in the model matches the user's actual Pd.

Embodiment to Scale an Anatomic Model of a User's Face with Dimensions Detected and Measured in Image(s) and then Applied to Scale a Model of the User's Face In this embodiment, a) A computer system configured with a camera or imaging device is used to acquire image data of a user; b) A reference target of known dimensions (eg coin, credit card, phone, tablet, screen, paper, ruler, etc,) is positioned such that it is visible in at least some images of the user; c) The reference target is determined to have at least one predetermined dimension (eg, diameter of a coin); d) The computer system detects the reference target in at least one image, including detection of the at least one predetermined dimension; e) The computer system detects facial features (pupils, irises, eye corners, mouth corners, nose, etc) in at least one image and measure the un-scaled distance between them; f) The computer system reconstructs an anatomic model of the user's face based on the image data; g) The computer system uses the ratio of the detected dimension of the reference target in the images and the predetermined size of the target to set a scaling factor to the detected facial features (Pd, distance between eye corners, width of mouth, etc); h) The computer system detects the facial features in the face model, measures the distance between them, and uses the scaled facial feature measurement to scale the face model; and, i) Optionally, the computer system detects the facial feature directly in a face model registered to the image data without first detecting the facial features in the image data.

Embodiment to Scale an Anatomic Model of a User's Face by Determining Depth with a Reference Target Present In this embodiment, a) A computer system configured with a camera or imaging device is used to acquire image data of a user; b) A reference target of known dimensions (eg coin, credit card, phone, tablet, screen, paper, ruler, etc,) is positioned such that it is visible in at least some images of the user; c) The reference target has at least one predetermined dimension (eg, diameter of a coin); d) The computer system detects the reference target in at least some images, including detection of the at least one predetermined dimension; e) as shown in FIG. 17 the computer system 1701 uses the detected dimensions 1705, the known size of the reference target 1704, and intrinsic camera parameters to determine the distance 1706 from the camera to the target; f) The computer system reconstructs a model of the user's face based on the images; g) The computer system uses the distance to the reference target and user's face and intrinsic camera parameters to determine the scale of the user's face model; and, h) Optionally, the computer system averages the measured dimension of the reference target from multiple frames to reduce error from any single image measurement prior to scaling the face model.

Embodiment to Scale an Anatomic Model of a User's Face Using a Computer System with Depth Detected in Images In this embodiment a) A computer system configured with a camera or imaging device with depth sensing capability is used to acquire image data of a user; b) The user positions the computer system to obtain images of themselves, while the computer system also measures distance from the computer to the user (rangefinder, autofocus distance, depth sensor, etc); c) The computer system uses the distance measured from the computer to the user and the intrinsic camera parameters to determine the scale of the images; and, d) The computer system reconstructs a model of the user's face based on the image data; with the model being inherently scaled based on the dimensions in the images.

Embodiment to Scale an Anatomic Model of a User's Face Using a Computer System with Depth Detected at Each Pixel In this embodiment a) A computer system configured with a camera or imaging device with depth sensing capability is used to acquire image data of a user; b) The user positions the computer system to obtain images of themselves, while the computer system also measuring distance from the computer to each pixel in the image data; c) The computer system uses the distance measured from the computer to the user at each pixel and uses the camera intrinsic parameters to scale each pixel of the image data; and, d) The computer system reconstructs a model of the user's face based on the image data, applying the scale of each pixel to the model, such that the model is scaled when completed.

Embodiment to Scale an Anatomic Model of a User's Face Using a Computer System with Depth Detected Only at Close Distances In this embodiment a) A computer system configured with a camera or imaging device with depth sensing capability is used to acquire image data of a user; b) A computer system configured with a camera with depth sensing capability is used to acquire close-up image data of a user, for example, including at least the user's eyes or other facial features in the image data; c) During acquisition of the close-up image, the user positions the computer system to obtain an image of at least some facial features, while the computer system also measures distance from the computer to the user; d) The computer system detects facial features (iris, pupil, etc) in the close-up image and measure the distance between the features; e) The computer system uses the distance measured from the computer to the user and intrinsic camera properties to determine the scale of pixels in the image data; f) The computer system determines reference distances between facial features based on the image scale and measured distance between features; g) The computer system reconstructs a model of the user's face based on the image data of the whole face of the user; and, h) The computer system detects facial features in the face model, measures the distance between them, and uses the reference feature measurement to scale the face model.

Embodiment to Scale an Anatomic Model of a User's Face Using a Computer System and a Double Mirror Reflection Referring to FIG. 20, in this embodiment a) A computer system 2001 configured with an imaging device 2003 and a display 2008 on the same side as the imaging device is used to acquire image data of a user 2004; b) The user 2004 acquires images in front of a mirror 2007 with the display 2008 and imaging device 2003 facing the mirror 2007 so they simultaneously acquire image data of the user and the device displaying previews of the image data which is also captured by the imaging device through mirror reflection; c) The computer system detects at least one dimension of the computer system in the image (size of screen, size of feature on computer, reference image on computer, etc); d) The computer system determines the known reference size of the detected dimension by providing its make/model, screen dimensions, size of reference image, etc.; e) The computer system detects at least one dimension (distance between eye features, size of head, model dimensions, etc) in each of the simultaneous sets of image data of the user (the user and the user on the display of the device); f) The computer system 2001 uses the reference dimension of the computer system and the intrinsic camera properties to determine the distance 2009 between the device and the mirror; g) The computer system uses the distance between the device and the mirror, the detected user dimension on the display of the device, the detected user dimension in the mirror, and the properties of the imaging device to set a scaling factor of the detected user dimensions; h) The computer system reconstructs a model of the user's face based on the image data; i) The computer system detects the user dimension(s) on the reconstructed model and scales the model based on the scaling factor; and j) Optionally, the user may place or hold a reference object against the mirror to determine the distance from the computer system to the mirror.

Embodiment to Scale an Anatomic Model of a User's Face Using Front and Rear Cameras of a Computing Device Referring again to FIG. 20 in this embodiment a) A computer system 2001 configured with a imaging devices on the front 2002 and back 2003 of the computer system a is used to acquire image data of a user; b) The user 2004 acquires image data in front of a mirror 2007 so they simultaneously acquire image data of the user with one camera (direction 2005) and an image of the reflection of the user with the opposite camera (direction 2006); c) The computer system detects at least one dimension of the computer system in the image data (size of screen, size of feature on computer, reference image on computer, etc); d) The computer system determines the known reference size of the detected dimension by providing its make/model, screen dimensions, size of reference image, etc; e) The computer system reconstructs an anatomic model of the user's face based on the image data with the computer system optionally using the pair of image data together as stereo data to enhance 3D reconstruction; f) The computer system registers the anatomic model on both sets of image data; g) The computer system uses the reference dimension, the registered anatomic models, and camera instrinsic parameters to determine the scaling factor of the model; and, h) Optionally, the user places or holds a reference object against the mirror to determine the distance from the computer system to the mirror.

Embodiment to Scale an Anatomic Model of a User's Face Using a Computer System and a Mirror In this embodiment a) A computer system configured with a camera or imaging device is used to acquire image data of a user positioned in front of a mirror with the camera positioned near their face; b) A reference target of known dimensions (eg coin, credit card, phone, tablet, screen, paper, ruler, etc,) is positioned such that it is on the surface of the mirror and visible in at least some images of the user; c) The reference target has at least one predetermined dimension (eg, diameter of a coin); d) The computer system detects the reference target in at least one image, including detection of the at least one predetermined dimension; e) The computer system reconstructs an anatomic model of the user's face based on the image data; f) The computer system uses the camera instrinsic parameters, the detected reference dimension, and the known dimensions of the reference object to determine the distance from the camera to the mirror. Since the mirror is the midpoint between the user and the reflection of the user seen by the camera, the distance from the camera to the user is 2× the distance from the camera to the mirror; g) The computer system uses the distance from the camera to the \user and the camera intrinsic parameters to set the scale of the image data; and. h) The computer system reconstructs an anatomic model of the user's face based on the image data.

Figure 21:
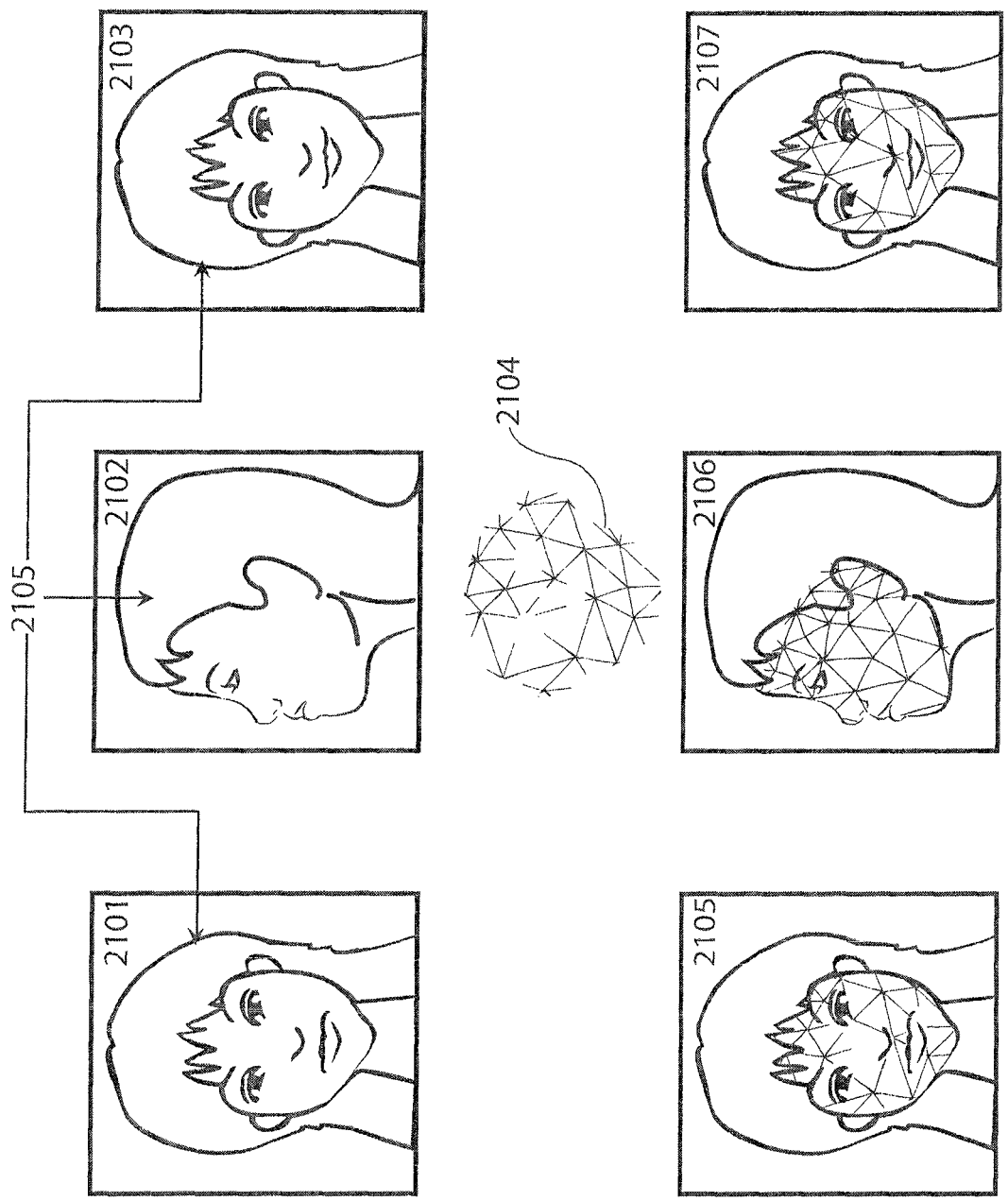
FIG. 21 is a diagrammatic illustration of the building and scaling of an anatomic model of the user's face from a collection of previously acquired images and fitting a 3-D face model across feature sets and camera positions.

Embodiment to Build and Scale an Anatomic Model of a User's Face with a Collection of Previously Acquired Images This embodiment has the advantage of using a collection of previously acquired images that the user may have at their disposal (eg collection of existing photos, photo gallery, social network or online image gallery photos, etc). Referring to FIG. 21, in this embodiment, a) A computer system receives a collection of images (e.g. 2101, 2102, 2103) of a user 2105, b) The images may be previously tagged with facial recognition data to determine which face in each photo is the user. c) If the images were not previously tagged, then the computer system performs facial recognition, prompting the user to confirm which face is theirs in at least one image or using the highest frequency of detected faces to determine the user from other people in photos, d) The computer system detects facial features (eg various points of the eyes, nose, mouth, ears, chin, etc) in each image of the user and fits a face model 2104 to the image data, e) Optionally, the computer system determines expression in each image (e.g. 2101 vs 2103) and adjusts the face model to a neutral expression, f) The computer system determines the pose of the user's face in each image, g) The computer system reconstructs a single model 2104 of the user's face by fitting a face model across the collection of feature sets and camera positions (2105, 2106, 2107) of the user. The face model is scaled by one of these methods: h) The computer system requests additional data from the user based on previously described methods: Pd input, an image with the reference target, etc. i) The computer system detects known objects in the images to determine a reference size (eg recognize a sheet of paper, a logo, a phone, etc). j) The computer system requests additional image data taken of the user with a reference object, using any other method described herein. k) The face model is inherently scaled due to the shape model containing dimensions that relate shape and size.

Embodiment to Scale a User's Face Using Existing Eyewear that they Already Possess Many people shopping for eyewear already own eyewear, and whether the eyewear fits well or not, it is used to help scale the dimensions of the user's face. Alternative, the manufacturer could send a sample pair of eyewear to be used for this process.

Figure 22:
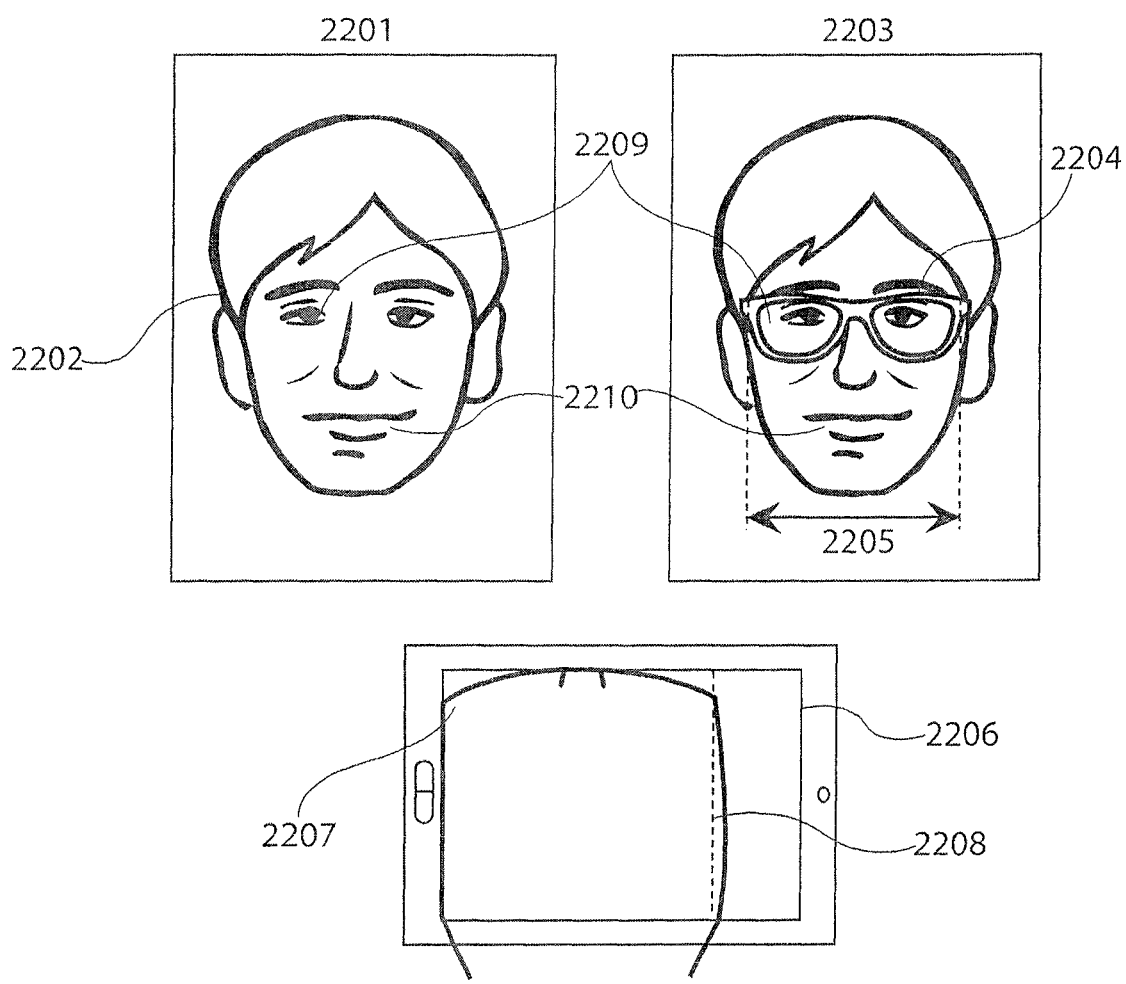
FIG. 22 is a diagrammatic illustration of the scaling of a user's face using existing eyewear already possessed by the user.

Referring to FIG. 22, in this embodiment, a) A computer system configured with a camera or imaging device is used to acquire image data 2201 of a user 2202, b) A computer system is used to acquire separate image data 2203 of a user wearing eyewear 2204 they possess, c) The computer system requests that the user provide reference dimensional information about the eyewear, such as the width 2205 or length of the frame, the size of the lenses, etc (e.g. a photo of the eyewear next to a reference target used to scale the eyewear, a measurement of the eyewear 2207 by aligning it with a reference 2208 on the computer system display 2206 that is set to 1:1 scale as explained in later embodiments, an entry of a measurement, model name of the eyewear, a ruler or interactive ruler displayed on the screen that the user can utilize to measure their eyewear, etc), d) The computer system reconstructs a model of the user's face based on the image data, e) The computer system detects the eyewear dimensions in the image data (eg overall width or height of frame, width of lens, etc), f) The computer system associates features or a model of the user's face between the image data with and without eyewear (e.g. eye 2209 and mouth corner 2210), g) The computer system determines a scaling factor for the face model based on the detected and reference eyewear dimensions and the features associated between the image data with and without eyewear, and h) The computer system co-registers the face model with the original user images such that the model coordinates and camera position align the face model with the pose, position, and scale of the images of the user's face.

Embodiment to Scale a User's Face Using Sonar

For any embodiment that requires calculating a distance from the computer system to the user or computer system to a mirror, a sonar method is used.

The following embodiment describes using sound to determine distance. a) A computer system configured with a camera or imaging device is used to acquire image data of a user, b) A computer system further configured with a microphone and speaker is used to emit a sound (e.g. series of frequencies, repeated sounds, etc) and record the same sound with a microphone, c) The sound is emitted from a on-the-device-speaker, a headphone on the user or held a distance, or other device, d) A computer system calculates the distance between itself and an object, such as the distance from the computer system to a mirror or distance from a headphone in the user's ear and the computer system, by analyzing the time elapsed from the sound being emitted by the computer system to being detected by the computer system's microphone, e) The computer system may use use multiple sounds, filtering, or other analysis to reduce noise, reflections, artifacts, and to optimize the accuracy of the distance detection, and f) The computer system uses the distance as described in other embodiments for scaling image data or an anatomic model of the user.

Embodiment to Determine Pd from Face Model that is Already Reconstructed and Scaled In this embodiment, a) A computer system obtains a scaled face model of a user from image data (using any method previously described), b) The computer system detects features of the eyes from the face model (irises, pupils, etc), and c) The computer system measures the distance between the eye features on the face model to calculate Pd Embodiment to Provide Users a Means to Measure the Size of a Reference Object of their Choice For any embodiment requiring a reference object of a known dimension, there are situations where the user needs to use an object that they or the computer system do not know the dimension of, ie a business card, a pencil, eyewear they possess, etc.

Figure 23:
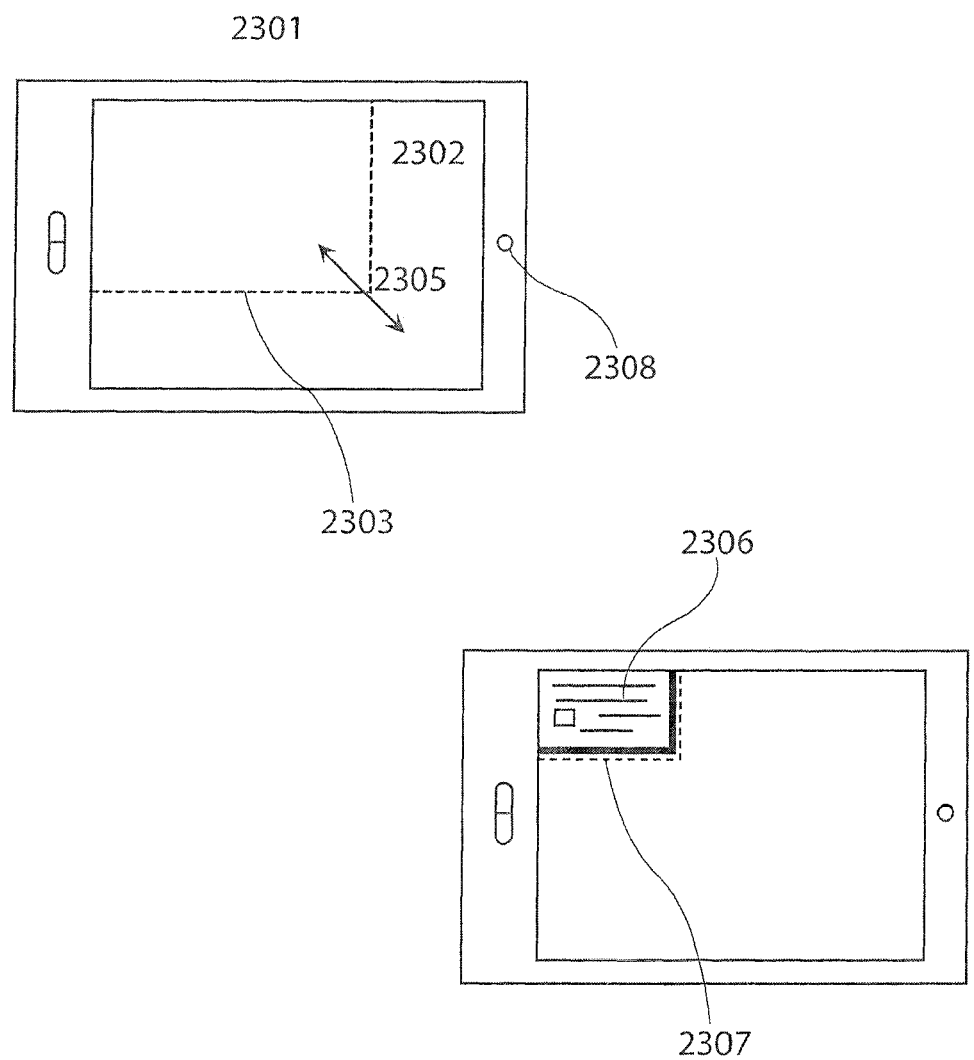
FIG. 23 is a diagrammatic illustration of a system for measuring dimensions of a reference object by displaying a reference box and calculating pixel size and the true size of the reference box.

This particular embodiment describes a system to measure rectangular objects (or objects that can fit within a rectangle) of unknown dimensions, but the method could be extended to any shape. Referring to FIG. 23: a) A computer system 2301 configured with a display 2302 and input device is used to display a reference box 2303 on the display, b) A computer system obtains information about the display of the computer system, such as resolution, pixel size, overall display dimensions. The computer system obtains this information from itself, software on the computer system, from a web browser, from the user providing information about the display or computer system model, c) A computer system calculates the pixel size of the display (for example, by dividing the length and width of the screen by the number of pixels). d) The computer system then calculates the true size of the reference box 2303 on the display, e) The computer system instructs the user to place their reference object 2306 against the screen and adjust as illustrated at 2305 the reference box 2303 using an input device (touchscreen, mouse, touchpad, gesture, etc) to match the size 2307 of the object, f) The computer obtains the size of the reference object by calculating the size of the adjusted reference box, and g) Optionally, the computer system is configured with an imaging device 2308 to take image data of the reference object such that it obtains information about the appearance of the object for recognition in future images. If the computer system is configured with a depth image device, it uses depth and scale information to enhance the measurement of the reference object.

For any embodiments that involve using a reference object, the object does not need to be perpendicular to the imaging device to obtain proper dimensions. With prior knowledge of the reference object, the angle of the object relative to the camera is determined. The angle and the measured distance on the image plane is used to determine to the true reference dimension of the object.

Optional User Preferences and Information

FIGS. 1A and 1B at step 104 describe capturing the user's prescription data and other information to inform the analysis. This step may be performed at a later time, although there is an advantage to capturing the data while the computer system analyzes the image data if it is computationally time-consuming. The computer system requests this information through a form that the user enters information into by means of an input device connected to the computer system. The computer system may also receive the information by obtaining image data of a physical set of information, such a photo of a prescription. The computer system may use optical character recognition to decode the image and extract the user's prescription data. The computer system may receive the user information though voice recognition, electronically transferred data or other means. The use of the information entered by the user will be described later in a description of modeling lenses and creating custom eyewear models.

Configurable Product Model

In FIGS. 1A and 1B steps 106 and 107 describe a configurable product or configurable eyewear model. In an exemplary embodiment, the configurable model is three-dimensional, configured with parametric features and dimensions, and represented as a 3D surface mesh. A 3D model of eyewear is created from a variety of methods such as 3D capture via scanning or photogrammetry, or through 3D computer aided drafting (CAD) or 3D modeling. It should be noted that a variety of other methods or representations of a configurable model could be used, such as 2D models, shape models, feature-based models, etc.

In an exemplary embodiment, a 3D parametric model is created by the eyewear manufacturer, including the frames and or frames and lenses. The 3D parametric model is created as a surface mesh or a solid model made of elements or features, including but not limited to polygons, curvilinear elements, etc. The parametric model enables altering one or more dimensions of the eyewear, which would update appropriate model and mesh elements, while maintaining consistent relationships between other features.

Figure 9:
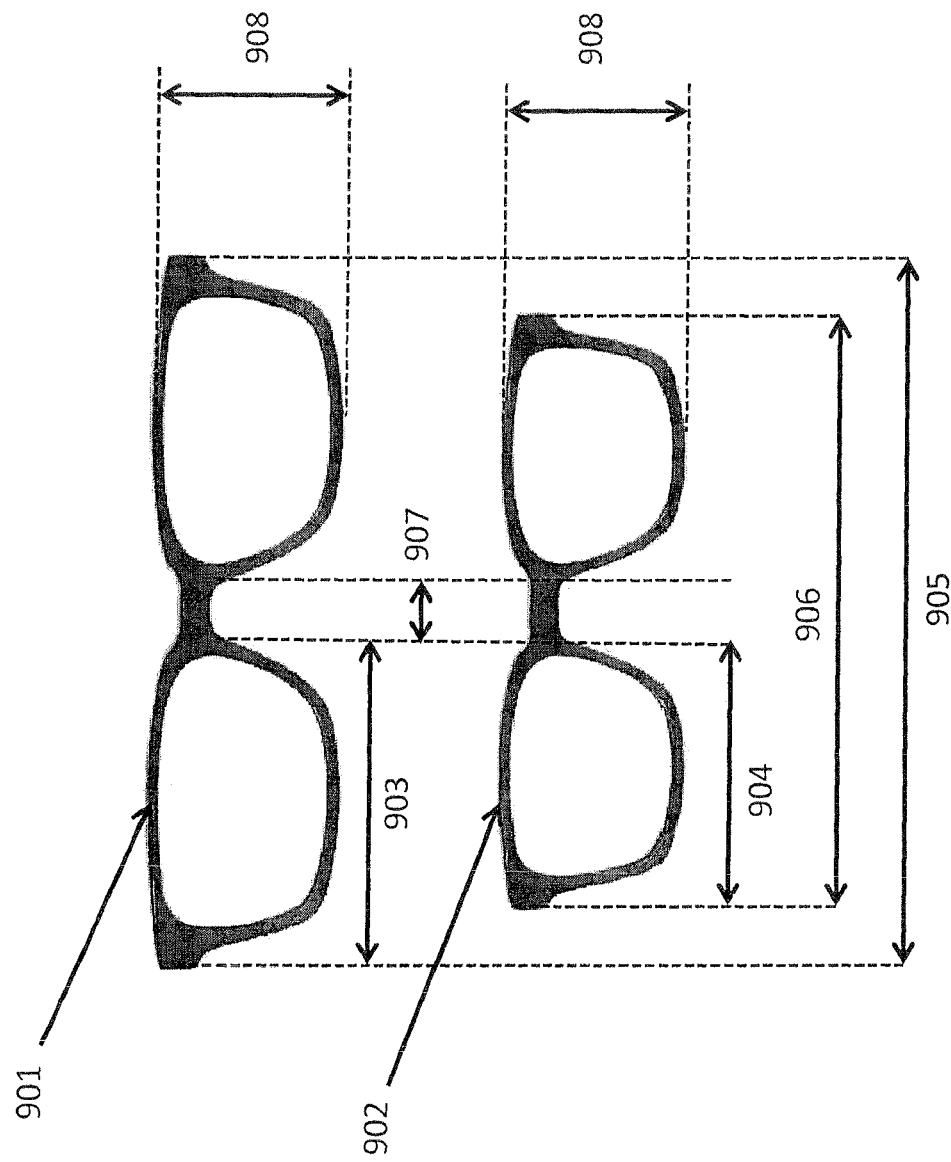
FIG. 9 is a diagrammatic illustration of an example of a parameterized eyewear model before and after adjustment to custom fit width without affecting other key dimensions.

FIG. 9 shows an example of an eyewear model 901 that was adjusted to eyewear model 902 by altering a parameter for the width 903 of the eyewear around the lens. The advantage of the parameterized eyewear model is that the width 907 of the bridge and nose pads is retained, the height 908 is retained, and the overall aesthetic appearance between eyewear models 901 and 902 is consistent. The parameterization enables a substantial change to just one aspect of the frame 901 without affecting other important elements of the design. The parameterized eyewear model has an advantage in propagating changes from a feature to the rest of the model while constraining all other features. These changes are represented as simple numeric values, which allows for very efficient data transfer and storage. These parameters could have up to infinite variability of the size and form of the product, allowing ultimate precision, if needed, in fitting a custom model to a user's anatomy and preferences. The ability to have high or infinitely variability of the form of the glasses in this example demonstrates a fundamental principle of one-up, from-scratch custom products. By changing and customizing the underlying form of a major component, in this case the front frame, in a highly unique manner that could never be done with pre-manufactured or stock components, the design is inherently one-up and custom-made for the individual user.

Figure 13:
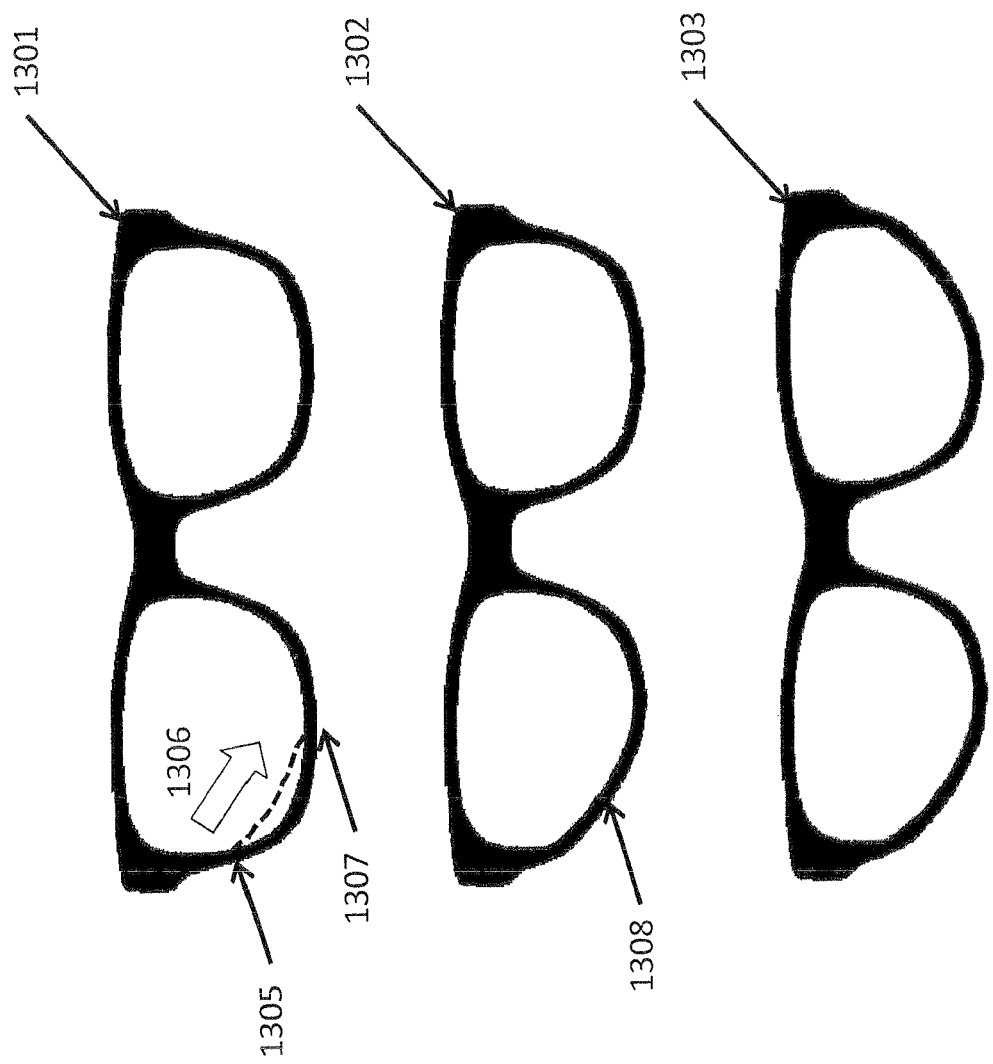
FIG. 13 is a diagrammatic illustration of an example illustration showing an eyewear design being edited.

FIG. 13 illustrates an example base eyewear design 1301, which demonstrates further shape customization. A base design is a fundamental style or shape that the eyewear model has, which may be modified through configuration and parameters. A computer system adjusts the curvature between points 1305 and 1307. Or a user directing a computer system input device selects a point on the eyewear at 1305 and move along the dotted line in the direction of the arrow 1306 to point 1307. The eyewear 1302 would then be modified in the region 1308 that was edited. To retain symmetry while simultaneously reducing the number of steps necessary to customize eyewear, a change on one side of the eyewear is equally applied to the other side of the eyewear, as shown in updated eyewear 1303. This symmetry effect is one example of a constraint that may be introduced as a feature of a configurable model.

The configurable eyewear model has constraints that prevent certain key parts/regions from being altered into a design that is no longer optimal to manufacture. For example, the minimum thickness of parts is limited to ensure structural strength, the minimum thickness around the lenses is limited to ensure the lenses can be assembled into the eyewear without the eyewear breaking, and the possible hinge locations is limited to ensure they could fit and sit at a proper angle. If a particular stock component hinge must be used, then the connection point of the hinge must be consistent regardless of how the underlying form and shape of the custom eyewear changes. Additionally, certain features are related due to symmetry or cascading effects; for example, if the computer or user adjusted the width or thickness of one part of the rim, the entire rim on both sides would adjust to ensure a symmetric and attractive appearance. The overall location of features remain constrained, such as the hinge and nose pad locations, etc. All these constraints and relationships would be pre-programmed by the eyewear designer and would be incorporated in the configurable model.

Figure 29:
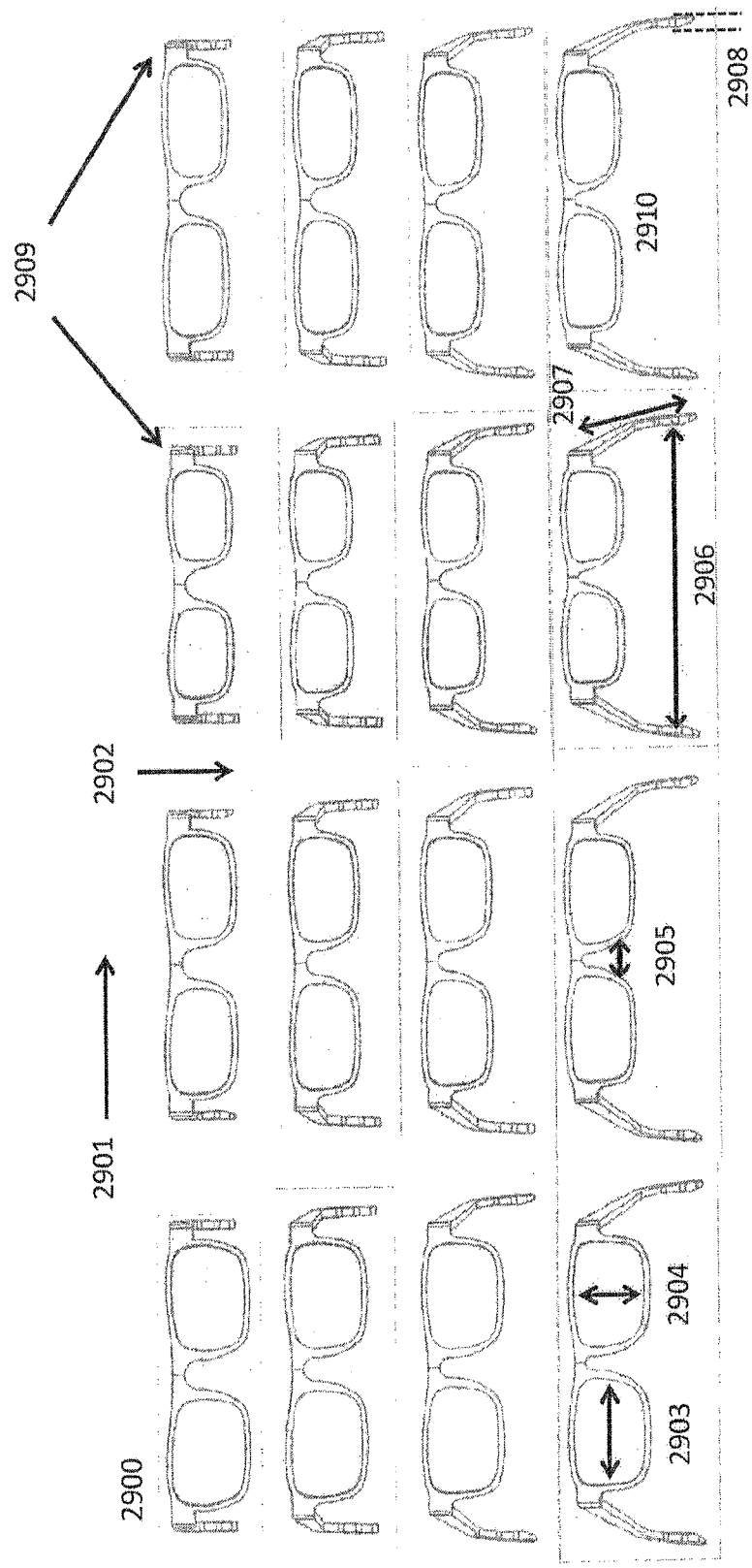
FIG. 29 is a diagrammatic illustration of configuring a custom product model, demonstrating a small portion of the degree of shape and size customization.

FIG. 29 illustrates an example of customization achieved with configurable product model; in particular, the ability to combine various parameters to refine and customize a product model. An eyewear model 2900 is configured to the 16 variations in the illustration. The 4 columns 2902 illustrate example configurations of the eyewear lens width 2903 and height 2904. The 4 rows 2901 illustrate the combinations of varying parameters for nose bridge width 2905, the distance 2906 between the temples where they contact the ears, the height 2907 from the front frame to the ears, and other subtle changes. Key features such as the material thickness 2908 and the hinge size and location 2909 remain unchanged. The parametric configuration enables the eyewear design to be highly configurable while remaining manufacturable. A manufacturer may use 1 hinge and 1 material thickness for all these designs and more, yet still allow massive customization of the underlying shape and size. Models 2900 and 2910 are quite distinct and they would traditional require different mass produced products. It would be completely impractical to offer this level of variation to customers with traditional mass-produced products, requiring thousands, millions, or more components to be designs and stocked. A configurable model with the rest of the method and system described herein allows one base model to be configured in all the configurations illustrated in FIG. 29, so one product can be custom tailored to an individual customer and then produced. It should be noted that these 16 variations represent an extremely small subset of the total potential variation of the design; there are thousands, millions, or infinite variation possible by interpolating between the examples shown, extrapolating beyond, and configuring other parameters not shown in the illustration. For example, if a configurable model has 10 parameters that can be altered; each parameter has 20 increments (which could also be infinite) such as distances of 2 mm, 4 mm, 6 mm, and so on; and the model is available in 20 colors and 3 finishes; then the total combinations of configurations for that one model would be $6\times10^{21}$, or six sextillion, which is 6000 multiplied by 1 billion multiplied by 1 billion. It should also be noted that these types of configurations are not limited to the type that consist of replacing and combining off-the-shelf parts. The fundamental shape and size of the components are entirely different for each parameter that is changed, requiring a model that is configurable and that the parts are made from scratch. This degree of customization can only be achieved with one-up, from-scratch custom methods described herein.

In addition to geometry, the eyewear model may have parameters for the surface finish, color, texture, and other cosmetic properties. The 3D eyewear model may be texture mapped with an image to represent the surface or rendered with texture, lighting, and surface properties such as reflectance, transmission, sub-surface scattering, surface or roughness to represent photo-realistic appearance of eyewear. The configurable nature of the model would allow a multitude of materials, paints, colors, and surface finishes to be represented. Various rendering techniques known to those skilled in the art, such as ray tracing, are used to render the eyewear and lenses in the most photorealistic manner possible, with the intension to accurately represent and reproduce on the display the frame and lenses exactly as how they would appear when manufactured. Other optical interaction effects, such as shadows and reflections, can be displayed on the eyewear and on the 3D model of the user's face. The 3D eyewear model has hinge points at the temples to allow the temples to flex with respect to the frame front and fit to the user's face model. In another embodiment, the 3D eyewear model also allows for a suitable amount of elastic modulus (stretch) in the bulk material property of the frame, and this elastic property can be dependent on the frame material selected.

Product Customization

Once an anatomic model is constructed, it is used to inform the placement and customization of a configurable product model. In an exemplary embodiment, the computer system automatically adjusts and the eyewear to the user's face based on at least one of: the quantitative anatomic model, the user's preference inputs, and the user's image data. The dimensions of the quantitative anatomic model and configurable eyewear model are both known to the computer system, various size adjustments are made automatically to ensure the best fit or arrive to a solution that is very close to the best fit. Three different approaches are described: a method to customize the configurable eyewear model prior to alignment/placement with respect to the anatomic model and rendering previews for the user, after alignment/placement with respect to the anatomic model but before rendering previews for the user, and after alignment/placement and rendering previews for the user, such that the user can provide additional input after seeing the base pre-configured eyewear model on their face.

Customization Prior to Placement on Anatomic Model

Figure 30:
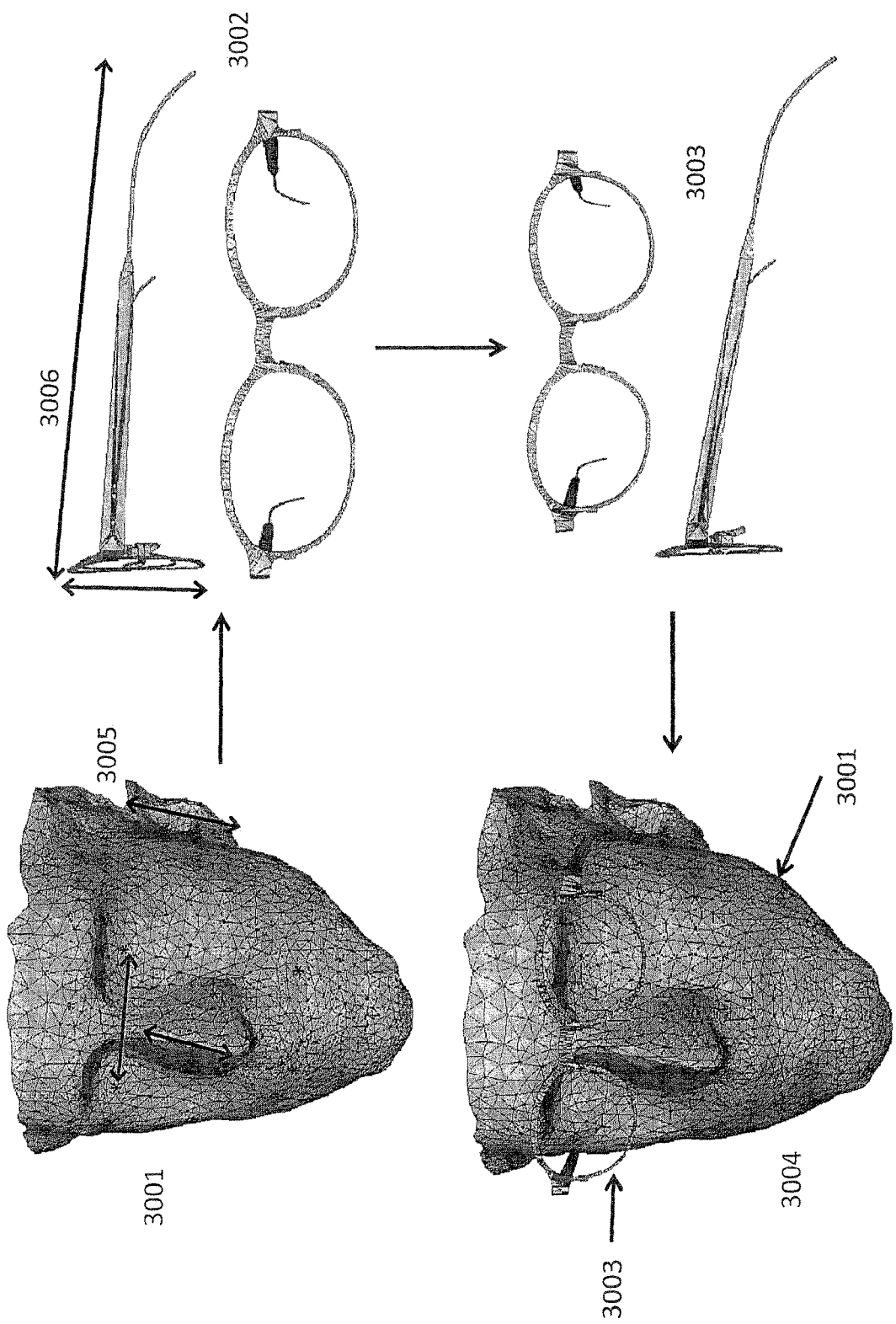
FIG. 30 is a diagrammatic illustration of customizing an eyewear model prior to aligning it to an anatomic model.

In one embodiment, the eyewear model is automatically customized prior to being positioned on the anatomic model; therefore creating an entirely new and custom design before ever fitting or rendering it directly to the user's images:

Refer to FIG. 30. In this embodiment, a) A computer system obtains a scaled face model 3001 (using any previously described method) that has key facial features 3005 identified, including but not limited to dimensions, points, lines, and surfaces of the eyes, nose, ears, brow, etc., b) The computer system obtains a configurable 3D product model 3002 that has key features 3006 identified, including but not limited to dimensions, points, lines, and surfaces of the temples, nose pads, lenses, bridge, etc. c) The computer system performs an optimization of the configuration product model parameters to reduce the error between various features of the face and model based on predefined fit metrics, such as the optimal ratio of eyewear width to face width, the optimal centering of eyes within lenses, etc. For example, adjust the length of the temples until the error between the temples and top of the ear are minimized. Or the computer system optimizes the fit and style based on other techniques, such as machine learning or analytic equations. d) The computer system updates the configurable product model 3003 with new parameters. e) The computer system performs an optimization to obtain a rigid transformation, as illustrated at 3004, to align the product model 3003 to the face 3001. The error between key features of the product and face is minimized, and some features are weighted more than others. f) The computer system transforms the coordinates of the product model to align it with the anatomic model, thereby placing a new eyewear design aligned with the user's anatomy.

Customization after Placement on Anatomic Model

Figure 31:
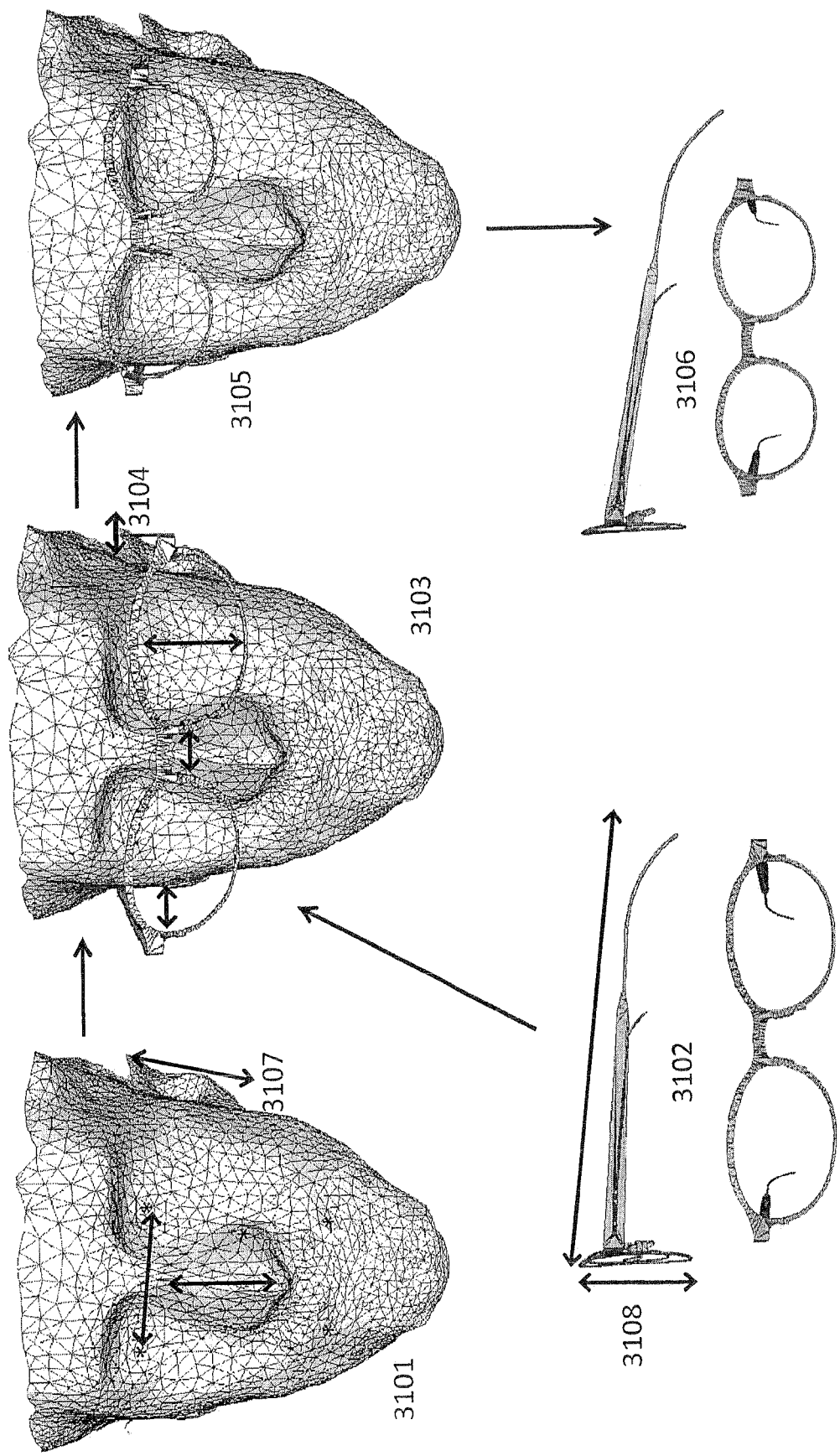
FIG. 31 is diagrammatic illustration of customizing an eyewear model after aligning it to an anatomic model.

In another embodiment, the base eyewear is positioned relative to the anatomic model and then automatic adjustments are completed as follows, creating an entirely new custom product prior to rendering for the user's preview. Refer to FIG. 31 a) A computer system obtains a scaled face model 3101 (using any previously described method) that has key facial features 3107 identified, including but not limited to dimensions, points, lines, and surfaces of the eyes, nose, ears, brow, etc. b) The computer system obtains a configurable product model 3102 that has key features 3108 identified, including but not limited to dimensions, points, lines, and surfaces of the temples, nose pads, lenses, bridge, etc., c) The computer system performs an optimization to obtain a rigid transformation to align the product model to the face, as illustrated at 3103. The error between key features of the product and face is minimized, and some features are weighted more than others. d) The computer system transforms the coordinates of the product model to align it with the anatomic model. As illustrated at 3104, the computer system analyzes, the interactions and dimensions and errors between the product model and anatomic model. In the example illustration, the eyewear model at 3103 is too large for the user's face, sits too low due to the nose size, and is too wide for the face shape. e) The computer system then automatically adapts the product model as illustrated in 3105 to further minimize errors between the facial features and product features based on predefined fit metrics, such as the optimal ratio of eyewear width to face width, the optimal centering of eyes within lenses, etc. The resulting custom model 3106 is better designed for the user.

Custom Fitting

The computer analyzes a set of measurements between the quantitative anatomic model and eyewear model. The set of measurements include but is not limited to: Width of eyewear relative to width of face; Distance between nose pads relative to width of nose; Angle, shape, or size of nose pads relative to angle, shape or size of nose; Length of temples relative to ear position; Height of eyewear relative to height of face; Height of each ear with respect to the eyes or other reference points; Distance between lens centers and eye centers; Vertex distance from inside lens surface to pupil; Outward angle of temples relative to frame; of lenses relative to the plane created by the front of the face; Eyewear wrap angle vs corresponding wrap curvature of the face.

The computer system uses these measurements to optimize a configurable eyewear model to the user's face. The automatic adjustment is informed by default metrics, such as optimal values for a ratio of eyewear-to-face width. Ideally each metric is a dimensionless ratio that scales properly across all user faces. However, some measurements, such as vertex distance may be specified dimensions. Ranges of optimal values may be used as well. Each metric is optimized individually, or they are optimized together if there is an interaction effect, such as the interaction effect between eyewear frame width and temple angle. For example, FIG. 14 shows a user quantitative anatomic model 1401 and configurable eyewear model 1402 in view 1411 before automatic optimization. A set of metrics is the ratio of width of eyewear 1403 to width of face 1404, angle of temples 1407, and length of the entire temples 1406 relative to the distance to the top of the ear 1405. As only one example, the optimal values for these metrics are 0.95, 87 degrees, and 1, for which the pre-optimized eyewear model 1402 does not satisfy. The computer system would seek to minimize the error between all three metrics and the optimal values. An optimization method such as least-squares, steepest descent, or others known to those familiar with the art is used to obtain a new set of eyewear parameters that best fit the users face. After the parameters are updated, the automatically adjusted 3D eyewear model as shown in 1412 is displayed, enabling a better first-visualization or approximation of all the eyewear models, as the width 1408, temple length 1409 and temple angle 1410 are better suited for the user. Automatically sizing the eyewear to a best-fit or close to best-fit size for the user enables a better shopping experience due to the reduced time and steps the user must take to arrive at the final eyewear design. The user may also be delightfully surprised seeing themselves in a pleasing eyewear design they had not preconceived or in styles they did not previously know would suite them. The concept of making every design and style fit well is a great first step to ensuring a good shopping experience.

Figure 28:
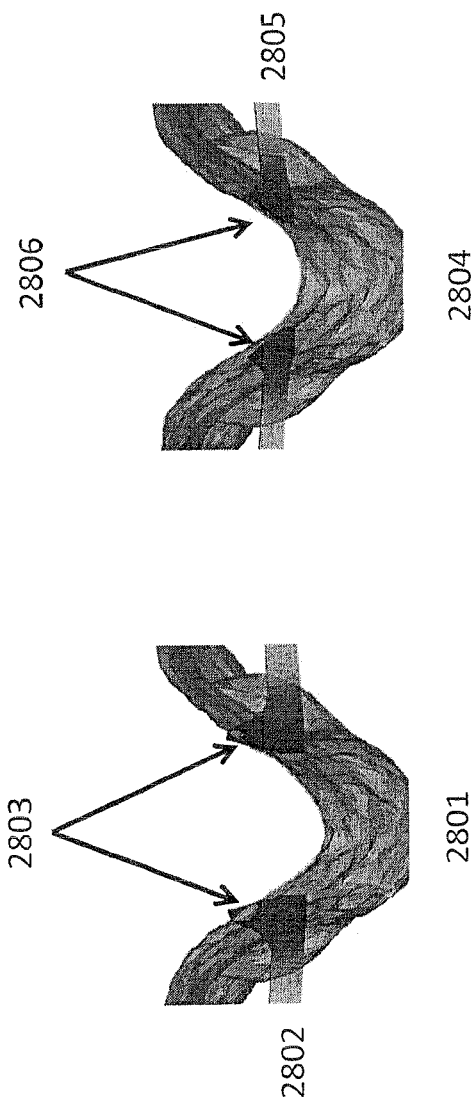
FIG. 28 is a diagrammatic illustration of a system for customizing eyewear nosepads to fit different users' anatomies.

By way of another examples, FIG. 28 illustrates a cross section of a nose 2801 and eyewear model 2802 prior to customization. The nose pads 2803 do not match the contour of the nose and intersect with the surface of the nose. The same nose 2804 is illustrated with eyewear model 2805, which was custom configured for the user. The nose pads 2806 now match the contour and angle of the nose and sit nicely on the surface. This is an example of the exceptional power of full customization, as the prior state-of-the-art does not enable full customization of nose pad contours to precisely match and fit a user's nose.

In some cases, when the eyewear model is highly configurable or the optimal values are well within the solution space of the parameterized design, no optimization is needed and a direct solution of the exactly specified metrics can be obtained. For example, if the temple length needs to be 103.4 mm and the front width of the glasses needs to be 142.1 mm, then the model could be adjusted to exactly these values.

Optimal values may vary based other factors entered by the user or determined from the image data, such as gender, age, face shape, eyewear style, purpose of eyewear, or what is currently fashionable. For example, females may prefer on average slightly smaller eyewear relative to their face size than males. Users choosing eyewear for recreational use may prefer increased frame wrap and a tighter temple fit to reduce wind in their eyes, widen their field of corrected vision, and/or provide more impact or sun protection. Users choosing plastic eyewear may prefer larger eyewear than users choosing metal eyewear. These user-defined preferences may be used to alter the optimal parameters during the customization process.

Customization and Aesthetic Prediction

In an exemplary embodiment, the custom fit and style is recommended by the computer system based on the user's image data and potentially additional information they provide. In addition to custom fit for a base design selected by the user, the computer system may also suggest eyewear styles, creating custom products specific for the user. Information about the user obtained from his imaging data and anatomic model that is used to provide custom suggestions includes but is not limited to:

Overall face size, such as area of the front of the face or volume of the head from the model; Face width; Face height; Ear positions (each ear may have different heights); Inter-pupillary distance; Size of eyes, such as area or length or height; Spacing between eyes; Asymmetries of the nose, eyes or mouth; Color of eyes; Color of hair; Amount and shape of hair; Color of skin; Ethnicity; Age; Location or local style trends; Gender; Assessment of cheekbone shape and location; Angle of forehead; Angle of cheeks; Circles under eyes; Eyebrow size and shape; Shape of face (e.g. round, square, oval, etc); Vertical position of eyes relative to center of face; Hair style (e.g. up, down, long, balding, straight, curvy); facial hair; Intensity or softness of features.

A portion of, all, or additional features are defined from the image data. Some features are directly measureable on the quantitative anatomic model. For example, the curvature of the nose and the positions of the ears are directly measureable from the anatomic model. In an exemplary embodiment, machine-learning algorithms are used to classify features. A training database of image data from a plurality of faces is collected and all features recorded. The computer system performs a plurality of analyses on each image, such as intensity maps, gradient filters, Haar filters, hessians, Sobel filters, Hough transforms, segmentation, and canny filters in order to measure or detect a plurality of features such as mouth angles, face edges, nose sizes, wrinkles, etc. For example, to estimate a wrinkle feature to aid with estimating age, the computer system analyzes the portion of the image segmented by the anatomic model. Within the bounds of the model, a Sobel filter is applied to detect edges and the intensity of edges. The face region is subdivided into a plurality of regions where the Sobel filter is applied, and the quantity and intensity of edges is quantified within each region. The sum of all regions for the face provides a feature to detect wrinkles. A person without wrinkles, who will only have edge features at key facial features such as eyes and mouth, will have a comparatively lower score than people with wrinkles, who will have more edge features due to their wrinkles. A machine learning method is used to classify the features in the training set, including but not limited to support vector machine, boosting, bagging, random forests, etc. The computer system then uses the machine learning classifier to relate image data to the desired features.

Other aesthetic characteristics may be quantified as well. Detecting skin features or hair features using previously mentioned techniques allows for those regions of the image data to be isolated. Image analysis of color would then allow a characterization of skin tone and hair color to be established. Clustering is a method that would enable categories of skin tones or hair colors to be established, grouping similar colors from the image together. Alternatively, machine learning methods could be used on the color space of the image data to train a classifier for determining aesthetic characteristics.

In an exemplary embodiment, the user is asked to provide some information as well to enhance or supplement data that is analyzed from his image data. Users provide information including but not limited to: Age; Gender; Location; Occupation; Style preferences such as 'trendy' or 'traditional'; the type of outfits they would like to wear glasses with (formal, casual, etc); Color preferences; Their favorite clothing; Preferential rating of different eyewear styles or shapes; and Words that describe themselves or their tastes.

Each feature may also carry a corresponding weight that signifies to the algorithm the importance of said feature. Alternatively, a user may link a social network website, personal profile, advertising database information about the user, or other such source of personal information to the computer system. This enables the computer system to import a variety of information about the user beyond what is practical to ask them, such as lists of their favorite music, celebrities, places they have visited, restaurants they like, or a language analysis of words and descriptors they use publicly. For example, if a user's posts on a blog or social website are analyzed, it may become apparent that 'red' is a color they mention far more frequently than other colors or that they wear dark formal clothing most frequently in their images, which could be used to inform the computer system about the user's color or style preference.

In an exemplary embodiment, the computer system would have a training database of preferences associated with the various features. These preferences include but are not limited to: Eyewear style, Eyewear material, Eyewear shape, Eyewear color, Eyewear finish, Eyewear size including local size adjustments, including overall size and custom local adjustments such as width, thickness, etc., Eyewear position on face, and Lens size.

The preferences are determined by actual users, designers, test users, or through other means. The preferences are set as a single favorite, plurality of favorites, range of favorites, ranked favorites, or scored favorites. Additionally, a user may have unfavorable preferences, or features that do not appeal to them. For example, a user may equally favor round and oval frame shapes, but dislike rectangle frame shapes. The preferences are set automatically based on the user's use of the computer system. In an exemplary embodiment, the user shops for eyewear and when he takes certain actions, such as rating the eyewear, adding the eyewear to their shopping cart, changing the eyewear, or answering questions about eyewear during their shopping process, the computer system records and associates his actions with preferences. For example, if a user repeatedly tries on, likes, and alters eyewear to have blue colors, then the color blue would be associated as a preference for that user.

In another embodiment, these preferences may be established with expert designers or test users. The designers or test users would progress through a specific set of questions or activities that require them to rank or rate various eyewear designs and features. They may also be asked to modify or customize eyewear to their preference. Based on the detailed testing of these users, a database of their preferences could be established.

The database then consists of a relationship between a plurality of variables: user's image data, quantitative anatomic models, and provided personal information; the analyzed data about users and their image data; and the preferences they have set. The computer system applies machine learning or predictive analysis to build a prediction of the response (preferences) based on the inputs from a new user: his new image data and anatomic model, personal information, and shopping behavior on the computer system. This approach enables an advantage of providing a highly customized and convenient eyewear shopping experience. For example, a user's image data analysis and a few basic answers to questions provides the following detailed profile of that user: a woman in mid-30s, dark medium-length hair, a square face, very small nose, slightly blue eyes, medium skin color, trendy fashion taste, white-collar profession, prefers bold fashion, wears glasses daily, and lives in an urban area. Each of these features may be associated with various eyewear preferences, and the combined information when classified by the machine learning method is able to recommend a set of eyewear that truly matches the user's preferences, even if she has not stated or does not know a priori her eyewear design preferences. When coupled with the methods to automatically size the eyewear, in the eyewear shopping implementation described herein, the user starts her shopping experience with a highly personalized experience, and arrives at a more ideal custom eyewear faster and easier than she would have through other existing shopping implementations.

Figure 24:
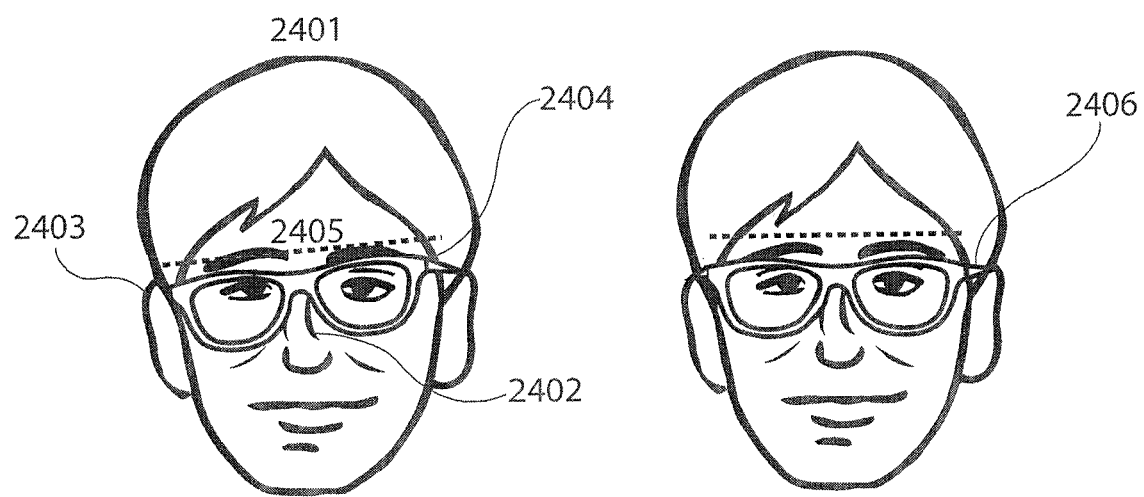
FIG. 24 is a diagrammatic illustration of a system for customizing eyewear design optimized to fit asymmetric facial features.

In another embodiment, the product model is customized for asymmetries. For example, FIG. 24 shows a user 2401 with common issues of a crooked nose 2402 and one ear lower than the other at 2403. These anatomic asymmetries of the face are present in many people and affect the way eyewear fits or looks on their face, often requiring manual correction by optometrists, which may or may not fix the problem. On user 2401, the eyewear 2404 sits at an angle 2405 and is shifted to the side due to asymmetrical facial features. In any previous embodiments for customization, the product model could be adapted differently for the left and right side of the face. This could be achieved through having different measurements, points, surfaces, or other geometries to optimize for the left and ride size of the product. The resulting eyewear may have different dimensions for the features on the left and right side, for example the temples are different lengths or the nose pad is shifted to one side. An additional constraint is added to the optimization to achieve a horizontal and well-aligned placement of the eyewear, irrespective of the user's asymmetrical features. After asymmetrical customization, user 2401 has eyewear 2406 that sits level and centered on the face.

It is desirable to design custom eyewear accounting for the user's face in various expressions. For example, the structure of cheeks change when a person smiles or brow shape change when a person frowns, which could cause interference with the eyewear design, resulting in eyewear moving or being uncomfortable during normal use. The following embodiment describes a method to customize an eyewear design that is optimized to fit across various expressions:

In this embodiment, a) A computer system configured with an imaging device acquires image data and construct a model of the user's face at a neutral expression (using any methods previously described), b) A computer system acquires additional image data or the user with at least one additional expression and constructs at least one additional face model (or obtain parameters necessary to adjust a single model to various expressions), and c) The computer system performs placement, design optimization, user adjustment, and preview with one additional constraint from previously described methods: The eyewear design, placement, and preview is performed across a plurality of face models representing the user at multiple expressions. The optimal design that satisfied the constraints of all the face models or all the expressions is produced, resulting in custom eyewear that is best fit to the user across their range of facial expressions and movements.

Customization and Optics

As previously described in FIG. 1B, step 104, the computer system prompts the user to enter his optical lens prescription information, which would be required to order prescription eyewear. The prescription info is also used to render lenses at the size, shape, and thickness that the user would receive in order to provide a more complete and realistic preview of the entire eyewear. Since different prescriptions require different optics (thinner or thicker lenses, more or less curvature), the user's specific prescription influences the visual appearance of their final product. If the user enters no data, an estimate of an average prescription lens or a plano lens (no optical correction) is used for rendering, which will at least provide a view of a lens in the eyewear frame. Alternatively, the user is asked general questions about their vision, such as near or far sighted, astigmatism, vision rating, type of lenses they prefer, etc. These generic questions could be used by the computer system to associate with the most likely lens size and thickness for the user. The custom lens rendering is viewed by the user to judge whether a certain frame style and size is acceptable given the strength of his prescription, and/or whether the lens index he has selected is appropriate. For example, after seeing a prescription of −9.0 rendered with standard lenses that have a standard index of 1.49 (resulting lenses would be thick), the user may prefer a different custom eyewear design that hides the thick lens edges or a higher index of 1.67 or 1.71 to reduce the lens thickness. The computer system also automatically suggests a lens index based on the frame design and prescription to provide the best visual and aesthetic appearance. For example, a user with a very strong prescription may prefer a plastic frame due to the capability of its thicker rim to better aesthetically mask a thick lens edge, and the computer system could make that suggestion.

In an exemplary embodiment, the user may select lens styles, including but not limited to lens tint (clear, various shades of sunglasses, photochromatic lenses with estimates of tint indoors and outdoors, polarized lenses, etc), prescription style (piano, single-vision, digitally compensated, bifocal, progressive, etc), lens material index (1.5, 1.67, etc), lens coating(s), lens edge lenticularization (thinning of the lens edges), or brand. Any changes that are visible are realistically rendered on the 3D eyewear model, including any distortion or optical effects that result from a particular lens type and prescription that an observer may see when viewing the user wearing the eyewear.

In an exemplary embodiment, more advanced measurements are derived from the quantitative anatomic model and eyewear model to enable digitally-compensated (i.e. freeform), progressive, or other advanced optical lens designs. In order to manufacture a digitally-compensated and/or progressive lens, a variety of measurements are ideally required, including but not limited to pupillary distance, vertex distance, pantoscopic tilt, frame wrap, and lens height relative to pupils. Traditionally, eye care professionals (opticians, optometrist, etc) take these measurements in-person utilizing specialized equipment or cameras. These measurements, even when done professionally are often difficult to estimate, such as measuring the distance from the surface of the eye to the back to the lens. Measurements using anatomic and eyewear models on a computer system are much easier and more precise since there are not physical barriers or limitations to taking a measurement. The user may have great advantage by obtaining the measurements automatically as they select their eyewear on the computer system, which eliminates the cost and time resulting from a visit to an eye care professional.

In another embodiment, the product model is configured to optimize the optical parameters used to make lenses. In addition to using the details and dimensions from the anatomic model to inform the lens design, the eyewear frame can be optimized to enhance the optical design. For example, standard vertex distance (distance from eye to inner surface of lens) is around 12-14 mm. With normal glasses, this can vary greatly, but configurable frames could be adjusted to achieve the optimal measurement. Other parameters include but are not limited to: frame wrap, eye placement relative to the center of the lens, pantoscopic tilt, etc. In this embodiment, a) A computer system obtains a scaled face model (using any previously described method) that has key facial features identified, including but not limited to points, lines, and surfaces of the eyes, nose, ears, brow, etc., b) The computer system obtains a configurable 3D product model that has key features identified, including but not limited to points, lines, and surfaces of the temples, nose pads, lenses, bridge, etc, c) The computer system analyzes dimensions of interest, including but not limited to vertex distance, pantoscopic tilt, Pd, and frame wrap, d) The computer system optimizes the product model parameters, which changes the shape of the eyewear and how it rests on the user's face, until the dimensions are within their desired range (e.g. vertex distance 12-14 mm), e) The computer system updates the configurable product model with new parameters, f) The computer system performs an optimization to obtain a rigid transformation to align the product model to the face. The error between key features of the product and face is minimized, and some features is weighted more than others, and g) The computer system transforms the coordinates of the product model to align it with the anatomic model.

As described above, FIG. 7 illustrates some of the various measurements needed. Pupillary distance (Pd) is measured as binocular 703a or monocular 703b measurements. Monocular measurements are often preferred to enable the best implementation of a user's prescription eyewear, but they are harder to measure accurately and generally require physical in-person measurement using specific equipment. Most Pd measurements performed on a single 2D frontal image of a user rely on a binocular measurement because it is easy for a system to detect the location of the eyes, while it is more difficult to accurately detect the exact center of the nose due to lighting constraints, the possibility the user is not facing the camera precisely, etc. However, the monocular Pd is better obtained by using the eye and nose features of the user's quantitative anatomic model. In this case, the additional information provided by the quantitative anatomic model allows the automatic determination of the center of the nose even if the individual 2D images used to construct the quantitative anatomic model were alone not sufficient to perform said measurement (for example, in no 2D image was the user perfectly facing the camera). If a straight-line distance were measured between the centers of the eyes, then the monocular Pd for each eye would be defined as the distance from the eye center to the center of the bridge of the nose. The vertex distance 709 is often hard to measure accurately in-person by a trained eyecare professional, but a quantitative anatomic model again provides an advantage. The vertex distance is the distance from the center of the eye to the inner surface of the lens. An eye care professional has difficulty measuring this parameter, on account of the difficulty of getting in-between the user's frame worn on his face and his eye. In-person, the measurement needs to be repeated for every eyewear design the user tries, which is quite inconvenient and time consuming. Thus the measurement is often estimated. However, this challenging dimension is calculated with great precision by a variety of methods applied to the quantitative anatomic model of a user wearing the eyewear, such as tracing a ray from the center of the eye's surface on the to the inner surface of the lens on the eyewear model. The perpendicularity of the ray relative to the plane of the face is ensured by using a variety of features in the model to construct a plane on the front of the face or by using the plane of lens. The pantoscopic tilt 710 is the vertical angle of the lens from perfectly vertical. Again, this dimension is measured using the quantitative anatomic model coupled with the eyewear model. A plane is defined through the lens and for the vertical position of the user's face. The angle between the planes about a horizontal axis is used to calculate the pantoscopic tilt. Frame wrap 704 is the horizontal angle of the lens positioned in the frame with respect to the user's face, and it is calculated with a similar method to the pantoscopic tilt by using the angle about a vertical axis. The fitting height 713 is calculated in a similar manner to the vertex distance. Once the computer system calculates lens position directly centered over the pupil (lens' optical center), a dimension which is needed to calculate vertex distance, the vertical distance to the bottom of the inside surface of the lens hole in the frame is calculated to determine the fitting height. All of these measurements have the advantage of being performed with a 3D lens positioned and previewed by the user relative to a quantitative anatomic model of the user.

In an exemplary embodiment, once the computer system has all the information necessary to manufacture a user's lens (all frame dimensions, pupillary distance, additional face measurements if the lens is digitally-compensated, prescription information, lens material index, and choice of lens lenticularization), the system can also realistically render the user's lens in the selected eyewear and positioned on the user's image data. Algorithms for reconstructing a 3D version of a lens given the above information are well established and are necessary in order to digitally surface and edge modern lenses. In an embodiment, the computer system uses sophisticated rendering techniques, such as rastering or ray tracing, to not only display the lens as a 3D object, but also render how light would be bent as it passes through the lens. Using said rendering techniques, the system can render a lens in a frame positioned on the user's face in order to allow the user to see exactly how they would appear as viewed by a third party. When the eyewear with lenses is placed on the user's face, an accurate distorted view of the face viewed through the lens can be shown. Moreover, the actual performance of an anti-reflective coating is represented to the user, as well as the appearance of lens distortion due to the inclusion of lens features such as no-line progressive, bi-focal (dedicated magnification zones), etc. With an accurate rendering in hand, a user is better able to make an informed decision as to the type of frame and lens selected, with the tradeoffs of various choices made clearer. When a user shops for a lens in a retail environment, he is pressured to increase the lens index material with the promise of a 20% reduction in lens thickness. But he has imperfect information; he is often not told how thick his lens will actually be in the frame he has selected, he often cannot often visualize what a 20% reduction means in actual reduction of mm, and he often cannot make such a comparison in the abstract without seeing the aesthetics of the lens in person. This imperfect information often results in the user paying for an upgrade that he would not have done had he been better informed: a 20% reduction may seem like a lot but in actuality may only be a reduction of 0.7 mm and may not provide enough utility given the price. In this embodiment, not only can the user be presented with a photorealistic rendering of the lens selected, but also all manner of lens configurations inside various frame configurations is presented and the user can make a more informed decision. Moreover, the lens ultimately manufactured will look exactly like the rendering, so there are no surprises.

In another embodiment, any lens configuration is displayed in a cross-section view such that the thickness of the lens in any location can be visualized and compared against other lens configurations (widths, index material, digitally compensated, etc)

Customization to Pre-Existing Eyewear

In another embodiment, the user captures image data of himself already wearing physical eyewear in his possession. The image data is captured by the computer system or the user provides the image data to the computer system. The computer system analyzes the image data using methods similar to those previously described, but with additional image processing to detect and determine the shape, color, and position of the eyewear. The computer system then adjusts configurable eyewear models to match the eyewear the user is wearing, similar to how the quantitative anatomic model is adapted to the user's face. Shape models or other algorithms may be used to adapt and fit eyewear model to the image data or features detected in the image data. This enables the user to duplicate, or duplicate and modify, eyewear they already possess. For example, a user may own a pair of eyewear they like with the exception of the frame color and width of the nose pads. The user may use the system to create a model of their eyewear, and adjust the frame color and nose pad width using the methods and systems previously described. The user may also use this system to indicate where on his nose he prefers to wear existing eyewear (for aesthetic, utilitarian, or comfort reasons). The system will then place all new eyewear designs in this location on the user's nose. In another embodiment, the user uploads any photo of any person wearing eyewear, and the computer system may detect and analyze the shape and color of the eyewear, then update a new 3D eyewear model for the user that best matches the eyewear photo. For example, the user may have seen a photo of a friend or celebrity wearing a certain style of eyewear, and they may upload a photo to obtain a similar design, which may then be further customized to their taste and anatomy.

In another embodiment, the eyewear designer or manufacturer provides a sample eyewear frame that the user may wear during part of the image data acquisition process. Similar to the method described previously, the computer system detects and analyzes the eyewear. In this embodiment, the advantage is that the eyewear model is a known size and shape to the designer. It's presence on the user's face in the image data provides both a reference scale for the data, since the size of the detected eyewear is known, and it provides a very strong detection feature to enable more robust anatomic model reconstruction. By tracking the known object in every frame and knowing it has consistent relationships to other features of the user's face, the computer system will have more robust detection of the user's features. Additionally, the user would be able to physically touch and observe the quality and craftsmanship of a sample eyewear frame.

Alignment

Referring to FIG. 1B at 108, the eyewear model is aligned with the anatomic model. In an exemplary embodiment, the configurable eyewear model and quantitative anatomic model are aligned based on an optimization of reference geometry. The alignment may occur prior to customization to inform the customization process with information about the geometric interaction between the user's anatomy and eyewear model or after customization and prior to rendering to ensure the eyewear model is appropriately placed on the user's face. Ideally, eyewear should rest with the nose pads tangent with and on the surface of nose, and temples on top of the ears and against the side of the head. The top of the eyewear should be a certain distance to the user's brow for a given design. The eyes should be as centered as possible in reference to the ideal eye location for a given design. Since there is no default placement and each person's face is different, an approach for custom eyewear must take into account the variable anatomy of each individual user.

Figure 10:
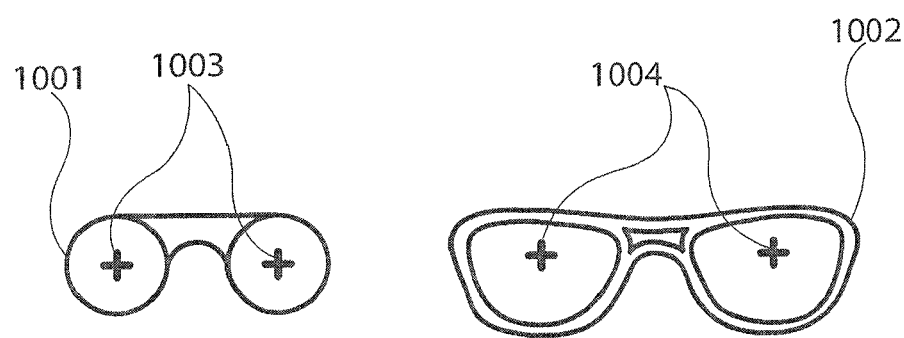
FIG. 10 is a diagrammatic illustration of two eyewear designs with optimal eye center locations.

FIG. 10 shows two example eyewear designs: small round frames 1001 and large aviator frames 1002. The optimal eye locations for design 1001 are shown as 1003, well centered within the eyewear's lens opening; the optimal locations for design 1002 are shown as 1004, off-center toward the top of the lens opening. The ideal initial placement of the eyewear would position the user's eyes as close as possible to (e.g. directly behind) these locations.

An optimization is obtained by minimizing the distance between the: center of the eyewear and centerline of the nose; the top of each modeled ear at the location of the intersection of the head and the bottoms of the temples (which sit on the top of the ears); nose pads on the eyewear and surface of the nose; center point of the eyes and the design's optimal eye location; pre-determined offset distance between the brow and/or check bones and the specific eyewear front-frame. Alternative combinations of locations and measurements could also be used to optimize placement.

In an exemplary embodiment, the temples of the eyewear flex at the hinges to ensure a fit with the user's face by remaining in contact with the sides of their face at the location above the ear where they make contact. For example, if the width of the user's head at the ears were narrower than the width of the eyewear, then the temples would bend inward to remain in contact with the side of this face so that the fit looks realistic and the user can visualize if the eyewear is acceptable to him. The computer system represents the eyewear as a multi-part dynamic assembly or a flexible assembly that can allow for angular rotation of the temples defined by the hinges. In another embodiment, the temples themselves allow for elastic deformation, bending inward or outward to ensure the temples are flush against the side of the head at the tops of the ears. In this embodiment, the computer system may represent the eyewear temples as a deformable unit that can safely elastically flex a pre-determined amount.

In another embodiment, the relationship between quantitative anatomic model features and the eyewear model is set by machine learning techniques and/or algorithms established from a database of training models, where the positions between the anatomic model and eyewear models have been set to optimal conditions. Based on new anatomic parameters and eyewear geometry, the system could assign an orientation and registration between the quantitative anatomic model and eyewear model using the classifier trained on the training data. This method could enable refinement of subtle user preferences for the placement of eyewear.

Custom Product Previews

Once a quantitative anatomic model is established, scaled, and registered to the image data and/or anatomic model, a representation of eyewear is fit to the user's face. Referring back to FIG. 1A, 15 and FIG. 1B, 109, describe rendering the eyewear model on the user's image data to create a custom preview. In an exemplary embodiment, the user is presented with his image data, with custom eyewear positioned correctly and superimposed on his face. In an exemplary embodiment, the quantitative anatomic model is not displayed to the user, but is used for alignment and measurement data. The data is displayed as interactive images that the user can adjust, rotate, and zoom by interacting with the computer system, including systems such as touch-screens, computer peripherals like mice, gesture interactions, or any other human computer interface technology. This would enable the user to see custom eyewear on their face at various orientations.

In another embodiment, at least one still image is shown, such as a front and side view, or multiple views at set degrees around a vertical axis centered on the users face. In yet another embodiment, an augmented reality approach is used. A live video feed of the user's face is shown using a computer system configured with a video camera. The quantitative anatomic model tracks with the user's face in real time, allowing the 3D eyewear model to be displayed and superimposed on the user's face in real time as the user moves his face in front of the computer system. This would create the illusion of looking in a mirror while trying on the glasses, as one would in a retail store. In yet another embodiment, the user's image data may not be shown, and instead they are presented with a model of their face and head along with the 3D eyewear model superimposed and correctly positioned on their face. Alternatively, the eyewear is represented as a series of pre-rendered images from various angles rather than an actual 3D model. This method could enable easy implementation of the display of high-quality pre-rendered images over network systems.

In another embodiment, the analysis of image data is performed remotely on another computer system such as a server(s) or cloud-computer(s) to take advantage of faster or more specialized or sophisticated computing capabilities than the user's computer system may possess. Remote servers possess thousands of networked CPU and GPU cores, with larger and faster data storage devices, yielding a system that is far more computationally powerful and/or efficient than the local computer system in possession of the user. The user's computer system transfer image data to the remote computer system, and after the image data is analyzed, the solution or additional data such as rendered images is transmitted back to the user's computer system through a network or other data transmission method. In another embodiment, the user's computer system perform initial computations prior to sending data to a remote system or final calculations after receiving data back from the remote system, with the advantage that said initial or final computations reduce the quantity of data to transmit to or from the remote system, or reduce the computational burden on the remote system.

The computer system analyzes the user's image data for lighting intensity, quality, source, and temperature. Once a quantitative anatomic model is constructed and registered to the image data, the computer system analyzes each individual image for at least one of the following:

Color temperature within the bounds of the anatomic model with reference to normal white balance.

Location of light and dark areas that correspond to highlights and shadows, which can inform an analysis of lighting source. By iteratively adjusting or directly computing a light source on the anatomic model and minimizing the error between computed and measured highlights and shadows, a lighting source or multiple lighting sources is detected.

The overall brightness and contrast within the bounds of the anatomic model informs the intensity and quality of the light source.

The information on lighting is used to apply light sources to the rendering of the 3D eyewear models to best match the image data, providing a near seamless integration of the eyewear model and user's image data.

To achieve a realistic and flattering preview for users, there is an advantage to setting a good white balance to the user image data such that the user appears to be in natural lighting with natural skin tones. Automatic white balance, as implemented in many image devices or image post-processing software, is used. Additionally, the detected face area is used to localize white balance information. There is further advantage to having specific objects in the image to use for accurate white balance. Color tints of yellow, green, or blue are common from different lighting sources, and the adjustment should remove them. In this embodiment a) A computer system configured with a camera or imaging device is used to acquire image data of a user, b) A white balance target of known dimensions is positioned such that it is visible in at least some images of the user, c) The computer system instruct the user to use a white or grey white balance target, such as paper, newspaper, a phone, phone case, electronic device. Or the white balance target is an object with a known color, such as paper money, an electronic device, or a logo, d) The computer system detects the white balance target in at least one image of the user, e) The computer system adjusts the white balance of the image data (e.g. rgb or color temperature and tint) until the target is neutral white or gray. And f) The computer system applies the white balance settings to all image data of the user.

The following embodiments describe systems and methods for creating previews of custom eyewear on the user's image or anatomic data. The quantitative anatomic model of the user's face is established, scaled, and registered to the image data such that the model coordinates and camera position align the face model with the pose, position, and zoom level of the images of the user's face. The configurable 3D eyewear model is aligned with the quantitative anatomic model. Images are rendered of the configurable eyewear on the image data or models of the users. The eyewear is rendered with a variety of techniques familiar to those skilled in the art, including but not limited to raster, scan line, and ray trace rendering.

Embodiment to Render Image of Eyewear on User Image Data

In this embodiment, a) A computer system sets a camera position such that the anatomic and configurable 3D eyewear models are aligned with the pose and position of user's image data, b) The computer system shows (or maintains) all surfaces of the configurable 3D eyewear model that are positioned between the camera and the anatomic model, c) The computer system hides (or deletes) all surfaces of the configurable 3D eyewear model that are positioned behind the anatomic model (eg, the anatomic model is between the camera and configurable 3D eyewear model), d) The computer system renders only the shown (or maintained) surfaces of the configurable 3D eyewear model, not rendering the hidden (or removed) eyewear surfaces or the anatomic model, and e) The computer system merges the rendered eyewear image onto the image of the user.

Embodiment to Render Image of Eyewear on User Image Data Using a Depth Calculation In this embodiment a) A computer system sets a camera position such that the anatomic and configurable 3D eyewear model are aligned with the pose and position of user's image data, b) The computer system calculates the depth (or distance) from the camera to all surfaces or vertices of the eyewear model and anatomic model at any given point in the image. The computer system may store the depth values, c) The computer system renders only the closest surfaces at any given point or pixel on the image, d) The computer system applies transparency to the anatomic model, such that it is not visibly rendered but is used in depth calculations, and e) The computer system renders the eyewear on a background consisting of the original image of the user.

Embodiment to Render Image of Eyewear on User Image Data with Ray Tracing

In this embodiment a) A computer system sets a camera position such that the anatomic and configurable 3D eyewear model are aligned with the pose and position of user's image data, b) The computer system sets the surface of the anatomic model as invisible in the final rendering, but opaque and non-reflective to rays, c) The computer system traces rays between the camera and the scene, d) The computer system renders only the configurable 3D eyewear model, since the anatomic model is invisible, e) The configurable 3D eyewear model is displayed with some parts hidden behind the opaque, but invisible, anatomic model, and f) The computer system merges the rendered image on the image of the user. The anatomic model may also be used as a surface that rays may cast shadows onto.

Embodiment to Render Image of Eyewear on User Image Data with a Mask

In this embodiment a) A computer system sets a camera position such that the anatomic and configurable 3D eyewear model are aligned with the pose and position of user's image data, b) The computer system renders the configurable 3D eyewear model and anatomic model as a binary mask image (eg 1 for pixels where the configurable 3D eyewear model is positioned in front of the anatomic model and 0 for pixels where the anatomic model is positioned in front of the configurable 3D eyewear model), c) The computer system renders the configurable 3D eyewear model, d) The binary mask is applied to the rendered image, hiding the anatomic model and any portion of the configurable 3D eyewear model that is behind the anatomic model, and e) The computer system merges the rendered eyewear image with mask applied onto the image of the user.

Embodiment to Render Image of Eyewear on User Image Data with a Mask During Render In this embodiment a) A computer system sets a camera position such that the anatomic and configurable 3D eyewear model are aligned with the pose and position of user's image data, b) The computer system renders the configurable 3D eyewear model and anatomic model as a binary mask image (eg 1 for pixels where the configurable 3D eyewear model is positioned in front of the anatomic model and 0 for pixels where the anatomic model is positioned in front of the configurable 3D eyewear model), c) The computer system renders the configurable 3D eyewear model with the mask preventing rendering in the black regions (the anatomic model and anything it is positioned in front of will not be visible or generated during rendering), and d) The computer system merges the rendered eyewear image with mask applied onto the image of the user

Embodiment to Render Eyewear with a Texture-Mapped Face Model

In this embodiment a) A computer system obtains a scaled face model of a user from image data (using any method previously described), b) The computer system uses the images acquired to construct the face model to create a texture-mapped image of the user and apply the texture-mapped image to the face model, c) The computer system positions a configurable 3D eyewear model to be aligned with the face model of the user (using any method previously described), d) The computer system renders the texture-mapped face model and configurable eyewear model together to create preview image data for the user, e) Optionally, the texture-mapped face model and eyewear model rendering is superimposed on the original images of the user or f) Optionally, the computer system allows the user to provide input to control or adjust the pose and position of the face and eyewear model, rendering the image data after each adjustment by the user.

Previews Using User Photos

It is desirable for a user to see previews of custom eyewear on any photo they choose. The image could be a favorite photo, professional photo, or other image that is different from the images used to build the anatomic model. This embodiment describes a method to align the anatomic model with a new image and then render the eyewear on the new image. In this embodiment a) A computer system obtains a new image of a user (not necessarily used to obtain anatomic data). The image is uploaded, linked to the computer over a network connection, sent via email, sins, or other communication systems, etc, b) A computer system obtains a scaled face model of a user from image data (using any method previously described), c) The computer system detects the face, estimate pose, and detect facial features in the new image, d) The computer system performs a rigid transformation of the face model and camera to align the face model features with the new image detected facial features, e) The computer system positions a configurable 3D eyewear model to be aligned with the face model of the user (using any method previously described), and f) The computer system renders the eyewear on the new image of the user (using any method previously described)

Simulated Camera Perspective

It is also desirable to simulate camera or vision properties (focal length, distortion, field of view, distance from subject) that are different than the camera used to acquire the image data. The user may want to simulate the perspective of human eyes or of a more flattering camera lens. When compared to human eyes or cameras at further distances, computer camera wide angle lenses that take photos at short distances often accentuate and enlarge objects closer to the lens (nose or glasses) and reduce the appearance of objects further from the lens (ears and side of head).

Figure 25:
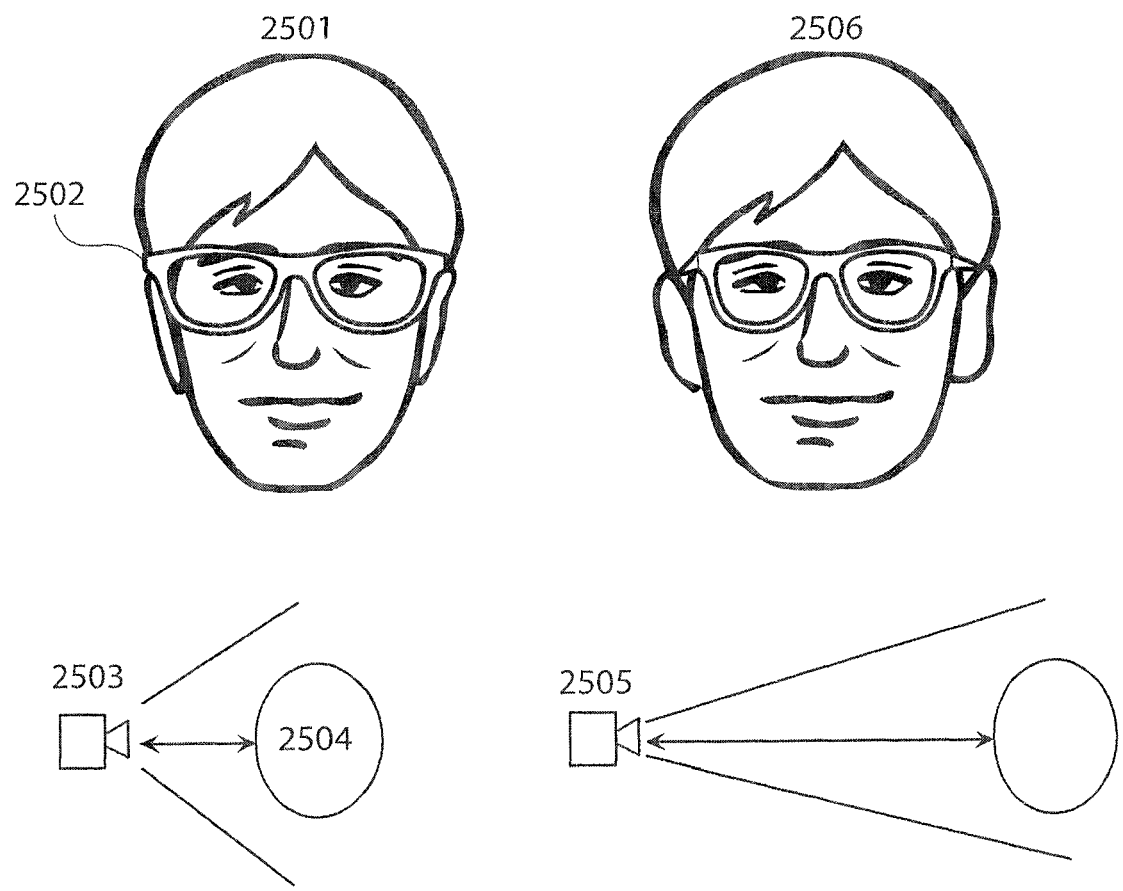
FIG. 25 is a diagrammatic illustration of a system to achieve a simulated camera perspective.

Referring to FIG. 25: a) A computer system obtains a scaled face model of a user 2501 from image data (using any method previously described), b) A computer system positions a configurable 3D eyewear model 2502 to be aligned with the face model of the user (using any method previously described) c) A computer system sets a camera position 2503 such that the anatomic and configurable 3D eyewear models 2504 are aligned with the pose and position of user's image data, d) A computer system alters the intrinsic camera parameters and distance 2505 from the model to simulate different perspectives and camera properties, while still maintaining the same placement of eyewear aligned with the user's image data 2506, e) The computer system renders the eyewear on the image of the user (using any method previously described), and f) Optionally, the computer system uses the anatomic information as seen from the original and simulated camera properties and position to deform and distort the original user images. The distortion could allow the underlying image data to better represent a different camera perspective.

Embodiments for Physical Previews

It is advantageous to have a physical preview of a custom product instead of a digital preview. The following embodiments describe two methods to provide a user with a physical preview of their eyewear:

In this embodiment a) A computer system obtains a scaled face model of a user from image data (using any method previously described), b) A computer system customizes a configurable 3D eyewear model to fit the face model of a user (using any method previously described), and c) A computer system converts the 3D eyewear model into a digital file for rapid manufacturing. Techniques include but are not limited to:
  i. directly 3D printing the eyewear model with plastic, paper, or metal. The model is converted to a hollow body to save cost and weight.
  ii. converting the 3D model into a flat pattern and cutting a flat sheet (paper, cardboard, plastic, metal, etc) with a CNC laser, waterjet, vinyl cutter, mill, etc. Optionally, folding or bending the flat sheet.
  iii. Converting the 3D model into multiple pieces, such as frame front and temples, that are produced Using the methods previously mentioned. Assembling the pieces using fasteners, glue, or other methods.
  d) A computer system receives an input from the User, including but not limited to: name and address, optional payment information, other contact information, shipping preferences, and e) A computer system generates instructions to build, package, and ship a rapid prototype of the custom eyewear model to the user.

In this embodiment a) A computer system obtains a scaled face model of a User from image data (using any method previously described), b) A computer system customizes a configurable 3D eyewear model to fit the face model of a user (using any method previously described), c) A computer system converts the 3D eyewear model into a digital file for rapid manufacturing. Techniques include but are not limited to:
  i. directly 3D printing the eyewear model with plastic, paper, or metal. The model is converted to a hollow body to save cost and weight.
  ii. converting the 3D model into a flat pattern and cutting a flat sheet (paper, cardboard, plastic, metal, etc) with a CNC laser, waterjet, vinyl cutter, mill, etc. Optionally, folding or bending the flat sheet.
  iii. Converting the 3D model into multiple pieces, such as frame front and temples, that are produced Using the methods previously mentioned. Assembling the pieces using fasteners, glue, or other methods.
  d) The computer system generates files for the user and provide a means for the user to obtain the digital files, including but not limited to an email, link to download from a network server, attachment to a digital message, etc., and e) The computer system generates instructions for the user to build the rapid prototype with the files, such as instructions to use a printer or 3D printer, instructions for assembly, instructions for sending the file to a service to be printed or build, etc.

Embodiment to Render a Life Size 1:1 Image of the Eyewear

The user may want to understand the true size of their eyewear in addition to a preview rendering of the eyewear on their images or model. For example, the user could compare the size to existing eyewear they own.

In this embodiment a) A computer system obtains a scaled face model of a User from image data (using any method previously described), b) A computer system customizes a configurable 3D eyewear model to fit the face model of a user (using any method previously described), c) A computer system obtains information about the display of the computer system, such as resolution, pixel size, overall display dimensions. The computer system obtains this information from itself, from a web browser, from the user providing information about the display or computer system model, d) A computer system calculates the pixel size of the display (for example, by dividing the length and width of the screen by the number of pixels), e) A computer system renders the eyewear model in various orientations, such as front view, side view, top view with a real-life scale of 1:1 by using the pixel size and dimensions of the eyewear model, f) A computer system displays the 1:1 images to the user, and g) Optionally, the computer system renders a real-time interactive graphic of the eyewear model that the User can control through an input device to rotate and pan in real-life 1:1 size.

Physics Based Preview

A common problem with eyewear fit is the nose and temple sizes being incorrect, resulting in eyewear that slips down the nose of the user. A physics-based preview method can simulate if eyewear will stay on the nose. The following is an embodiment for physics-based adjustment:

In this embodiment a) A computer system displays a preview of a custom eyewear model on a user's image data and face model (using any method previously described), b) A computer system accepts user input (touch screen, slider bar, mouse control, gesture, etc) to move the front frame of an eyewear model vertically up or down with respect to the user's face and/or move the front frame closer or further from the user's face, c) A computer system enforces constraints to ensure the eyewear does not interfere with the model, such as the nose pads intersecting the surface of the face model or the temples intersecting the top of the ears of the face model, d) A computer system applies the following physical properties to the eyewear model and face model
  i. Mass of eyewear model, which is estimated from its volume and material properties
  ii. Coefficient of friction of eyewear material
  iii. Coefficient of friction of skin, which is estimated as a general property for human skin
e) A computer system solves a system of mechanics equations representing the balance of forces between gravity acting on the mass of eyewear and the opposing frictional force of the eyewear nose pads contacting the face model nose surface and the eyewear temples contacting the face model ears, and f) The mechanics equations are iteratively solved until a steady state is reached where the eyewear is positioned with balanced forces supporting it.

Lens View Rendering

In another embodiment, the computer system simulates the vision of the user when wearing progressive eyewear. The user is presented with a view such that he can look through his configured lens and see the world as he would see it through the lens. This technique is best applied to the custom configuration of no-line digitally-compensated (freeform) progressive lenses. A photo can be displayed on the screen (pre-selected or user-uploaded or a live image stream from the computer system imaging device) with the lens positioned in front of the image. Information is superimposed over the lens identifying the various corrected regions of the lens to the user (areas with distortion, corridor, areas of maximum magnification, transition areas, etc). The system can display how far away it has virtually positioned the photo behind the lens, and using ray tracing rendering techniques known to those in the art, the photo can be distorted as the light passes from the photo through the lens and to the viewer. Changes to the lens design or shape/size of the eyewear can update in real-time in this preview. A user would be able to better understand the areas of the lens that would be distorted (peripheral areas in a progressive lens), and the amount of distortion given various digital lens designs. In another embodiment, the computer system uses its imaging sensor to provide a live preview of what it sees through the system display, and the computer system may distort this view in real-time given the lens design selected. This live-preview augmented-reality view would allow the User to experience life as seen through the lens they have customized given lens parameters and custom frame parameters.

User Interaction and Control

Referring to FIG. 1A at 16 and FIG. 1B at 110, 113, 114, the computer system provide a means for the user to interact with the computer system for shopping, selecting, editing, modifying, previewing, controlling the preview, visualizing, purchasing, and performing other activities related to customizing a product.

Figure 11:
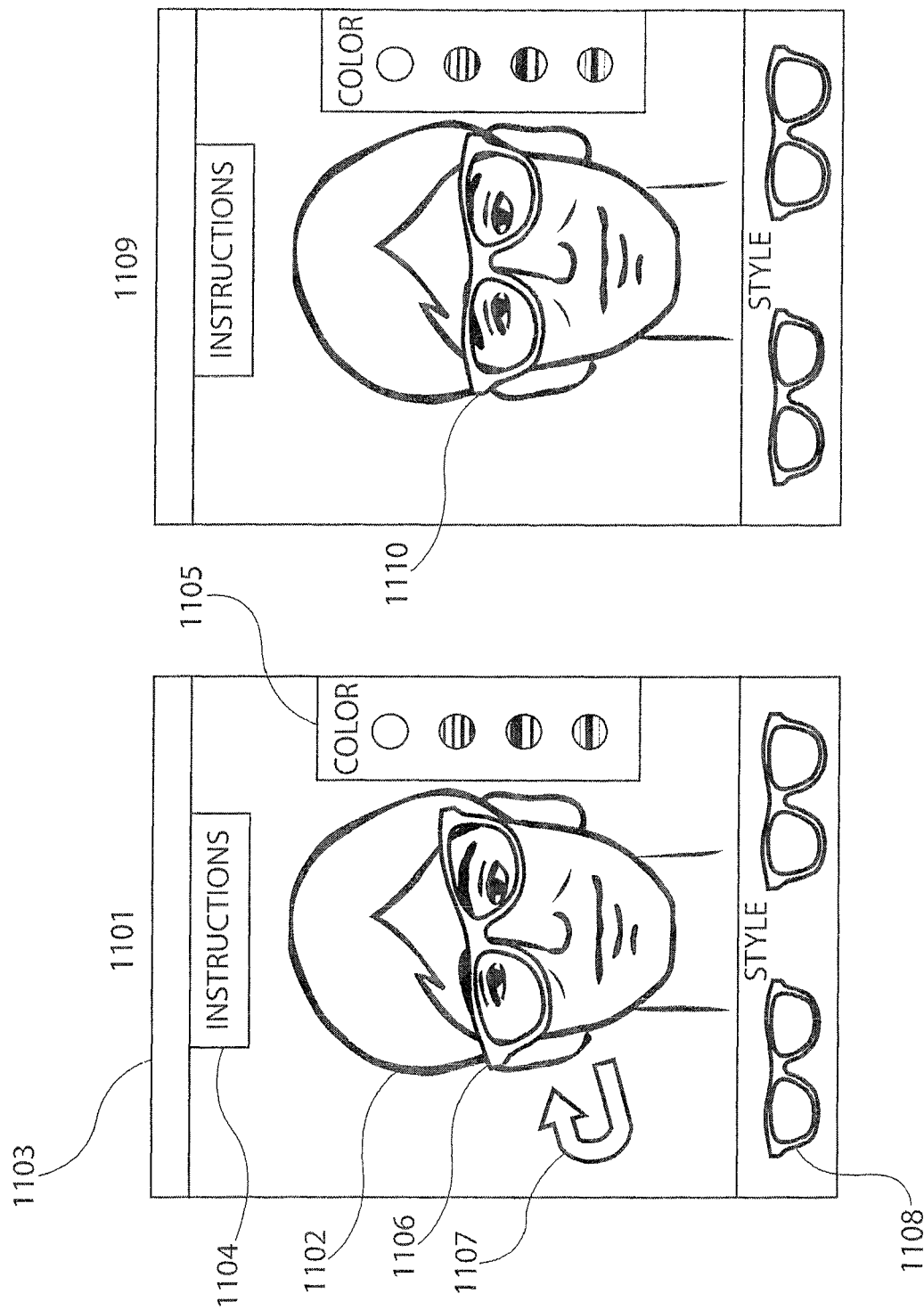
FIG. 11 is a diagrammatic illustration of an example computer system interface for previewing, correcting, and customizing eyewear.

FIG. 11 shows an example computer system interface 1101, which would be shown on the display of the computer system, with a preview of eyewear 1106 on user 1102. The computer system interface contains controls 1103 for ordering, viewing, configuring, sending previews, sharing, obtaining help, or other functions. The eyewear style or base design is selectable with controls 1108 and colors/finishes with controls 1105. Instructions are provided to the user through the display of 1104. It should be recognized by those skilled in the art that a variety of other designs could suite the same needs described for viewing, customizing, and ordering eyewear. For example, multiple views of the eyewear may be used, such as 2, 4, or 9 windows displayed with different styles at the same time or different view perspectives of the user. In one embodiment, the computer system displays multiple instances of the user, with each instance wearing a different configuration of custom eyewear. Each eyewear shown may have one or a plurality of options changed. For example, the display shows nine instances of the user's face, with each instance showing the user wearing the same custom eyewear design but each design is displayed with a different color, style, or lens material. In another example, multiple instances of the user is displayed, with each wearing the same style and color of eyewear but automatically sized to the face slightly differently, such as slightly larger or smaller variations or altering the eyewear placement slightly higher or lower on the face (using the same sizing algorithm or a plurality of competing algorithms). In another example, the display shows multiple instances of the user wearing the same or different custom eyewear as viewed from a different angle (front, isometric, side, top). As one instance of the user is manipulated, all instances update simultaneously. For example, as the user changes the view of one instance, the same change of view is applied to all instances.

In an exemplary embodiment, the computer system allows the user to adjust the position of the eyewear model on his face. The user selects the eyewear with their input device and adjust it at certain locations by moving, dragging, or making other controlling actions with the input device. For example, the user grabs the eyewear at the temples and slide them up or down to fit better onto the ears, or he grabs it at the nose bridge to place or adjust how and where it sits on his nose. Additionally, the user is able to correct any errors in the automated placement of the eyewear.

In another embodiment, the eyewear model is adapted and configured in real-time or near real-time as the user makes adjustments to the position. For example, typically one would simply moving the eyewear to a new position for previewing, which may result in the eyewear no longer fitting while in that position because the nose may be too narrow or temples too long or some part may not fit based on the new position. With configurable eyewear, the model is adapted as the user moves it, such that the eyewear changes shape to fit the user's face in the new position. If the user pulled the eyewear away from their face, the nose pads would slightly lengthen and the temples would slightly lengthen among other changes, as opposed to the nose pads being too short and temples too short, and the glasses falling off the user's face without adjustment.

For example, in FIG. 11, the eyewear 1106 on user 1102 previewed with interface 1101 is positioned at an incorrect angle. The user adjusts the positioning by selecting eyewear 1106 with an input device and moving it in the direction 1107 shown. As shown in view 1109, the preview then is updated to show eyewear 1110 properly positioned on the user's face per the user's specification. Alternatively, the user is able to manually identify specific points where the ears, eyes, nose, and other features are so the computer system can align eyewear more accurately. It is common that a person's left and right ear is at different heights, usually causing eyewear to sit crooked or angled. The ability adjust the angle and ensure that the custom eyewear design accounts for the differing heights of the left and right ears provides a great advantage to the user obtaining and proper and comfortable fit. With a configurable eyewear model, the proper fit can not only be displayed for preview, but actually configured and manufactured so the user gets a product that fits in real-life as well as it looks on preview, a distinct advantage over prior art.

Once an eyewear model is automatically placed on an anatomic model of a user, it is desirable to allow the user to adjust placement to their preference during preview. For example, the user may like to wear their glasses higher or lower with reference to their eyes or nose or further or closer to their face. These adjustments can help to inform a custom eyewear design that is fitted to position the eyewear to the user's preference. One of the great advantages of fully custom eyewear is that the underlying design can be adapted to fit a user's placement preference. Typically a user could preview or wear eyewear at different positions on their face (closer or further from the eyes or higher or lower on the nose), but if the eyewear is not the right size and shape, then it will be uncomfortable, not stay in position, or not be possible to wear at the desired position. The following embodiments describe systems and methods to enable custom placement of custom eyewear:

Embodiment to Adjust the Vertical Position of an Eyewear Model on a User's Face by Setting Vertical Position and Adapting Eyewear Model Placement In this embodiment, a) A computer system displays a preview of a custom eyewear model on a user's image data, b) A computer system accepts user input (touch screen, slider bar, mouse control, gesture, etc) to move the front frame of an eyewear model vertically up or down with respect to the user's face, c) The computer system solves a system of constraints to properly adjust the eyewear model on the user's face.
  i. The front frame vertical height must be in the vertical position specified by the user
  ii. The temples of the eyewear must contact the top point where each of the user's ear and head intersect of the face model. The temples is adjusted to different heights depending on symmetry or asymmetry of the user's face
  iii. The nose pad regions of the eyewear must contact but not intersect the user's nose of the face model
  iv. Optionally, the system of constraints could be other points, lines, surfaces, or features as previously described.
d) If the constraints can be satisfied by adjusting the eyewear position to achieve the user-specified vertical position of the eyewear model, then the system will display an updated preview with the new eyewear model position, and e) Optionally, if the constraints cannot be satisfied, the system informs the user that the position is not possible or that they eyewear may not fit properly (e.g. slip down nose). Alternatively, if the calculation is done in real-time, the user will only be able to adjust the eyewear within a set range of vertical distances.

Embodiment to Adjust the Position of an Eyewear Model on a User's Face by Setting Position and Adapting Eyewear Model to Achieve the Desired Position In this embodiment a) A computer system displays a preview of a custom eyewear model on a user's image data, b) A computer system accepts user input (touch screen, slider bar, mouse control, gesture, etc) to move the front frame of an eyewear model vertically up or down with respect to the user's face and/or move the front frame closer or further from the user's face, c) The computer system solves a system of constraints to properly adjust the eyewear model on the user's face,
  i. The front frame vertical height and closeness to the face must be in the position specified by the user
  ii. The temples of the eyewear must contact the top point where each of the user's ear and head intersect of the face model. The temples is adjusted to different heights depending on symmetry or asymmetry of the user's face iii. The nose pad regions of the eyewear must contact but not intersect the user's nose of the face model
iv. Optionally, the system of constraints could be other points, lines, surfaces, or features as previously described.
d) If the adjustment creates a gap or interference between the eyewear model and user's nose in the face model, then the nosepiece of the eyewear model is adapted by the computer system (adjust thickness, position of pads, width, etc) to create a contact with the user's nose. e) If the adjustment creates a gap or interference between the temples and the user's ears of face, then the temples is adapted by the computer system (adjust length, angle, etc), f) If the adjustment creates a gap or interference that is outside the solvable domain of the custom eyewear model constraints or if large portions of the eyewear cause interference (eg entire frame moves into the face), the computer system does not allow adjustment to the unacceptable position, and g) The system displays an updated preview with the new eyewear model position Embodiment to Adjust the Position of an Eyewear Model on a User's Face by Pre-Computing a Series of Options In this embodiment a) A computer system calculates the optimal fit of an eyewear model on a user's image data, b) A computer system creates a plurality of adjustments to the vertical position of the eyewear, moving it up and down the nose or further/closer to the face in set increments from the optimal position (ie, +4 mm, +2 mm, −2 mm, −4 mm), c) A computer system pre-renders images of the user with the eyewear model in all the adjusted configurations, d) A computer system displays a preview of a custom eyewear model on a user's image data, e) A computer system accepts user input (touch screen, slider bar, mouse control, gesture, etc) to move the front frame of an eyewear model vertically up or down with respect to the user's face in the increments that were used to pre-compute the adjusted configurations, and f) The computer system displays the adjusted configuration rendering that matches the users selection Embodiment to Adjust the Vertical Position of an Eyewear Model on a User's Face with Surface Constraints In this embodiment a) A computer system calculates the optimal fit of an eyewear model on a user's image data, b) A computer system sets constraints that limit the potential movement between the eyewear and face models,
  i. The eyewear model only moves in certain directions (e.g. further/closer to the face or vertically up and down)
  ii. The eyewear model only rotates along an axis formed by a line through the contact point between each ears and temples
  iii. The eyewear model must maintain contact between the temples and the top point where each user's ear and head intersect on the face model
  iv. Both eyewear model nose pads must be in contact or within a tolerance of the nose surface on the face model
  v. Optionally, the system of constraints could be other points, lines, surfaces, or features as previously described.
c) A computer system displays a preview of a custom eyewear model on a user's image data, d) A computer system accepts user input (touch screen, slider bar, mouse control, gesture, etc) to move the eyewear model. The computer system calculates the system of constraints with each user input, e) The eyewear model only moves within the predefined constraints, and f) The computer system displays the eyewear model position adjustment as it is moved by the user.

Embodiment to Adjust the Vertical Position of an Eyewear Model on a User's Face with an Image of their Current Eyewear A user may already possess eyewear that sits on their face in a position they prefer. This embodiment describes how a new custom eyewear is designed such that the same positioning is obtained, even if the eyewear style, shape, and design are different:

In this embodiment, a) A computer system configured with an imaging device acquires image data and construct a model of the user's face (using any methods previously described), b) The user uses the computer system to acquired image data of the user wearing a eyewear positioned to their preference, c) The computer system extracts anatomic locations of where the eyewear contacts the user's face (eg where the nose pads rest relative to the user's nose) and/or reference positions of where the eyewear is located with respect to facial features (eg the top of the eyewear is positioned a certain distance above the eyes or the distance down the length of the nose where the eyewear bridge is positioned), d) The computer system uses the anatomic locations and/or reference positions to optimize the fit and design of new custom eyewear, e) The computer system solves a system of constraints to properly adjust the eyewear model on the user's face.
  i. The front frame vertical height, angle, and closeness to the face must be in the position closest to the extracted data
  ii. The temples of the eyewear must contact the top point where each of the User's ear and head intersect of the face model. The temples is adjusted to different heights depending on symmetry or asymmetry of the user's face
  iii. The nose pad regions of the eyewear must contact but not intersect the User's nose of the face model
  iv. Optionally, the system of constraints could be other points, lines, surfaces, or features as previously described.
  f) A computer system displays a preview of a custom eyewear model on a user's image data User Interaction and Control of Configurable Model A great advantage of a custom eyewear system is the ability for a user to directly modify and update the product to their preference. In an exemplary embodiment, the computer system provides the user with control to edit or adjust the eyewear shape from the base design, which serves as a template for modification. The base design may have already been automatically customized for the user by the computer system or it may be the original base design prior to any customization.

Figure 12:
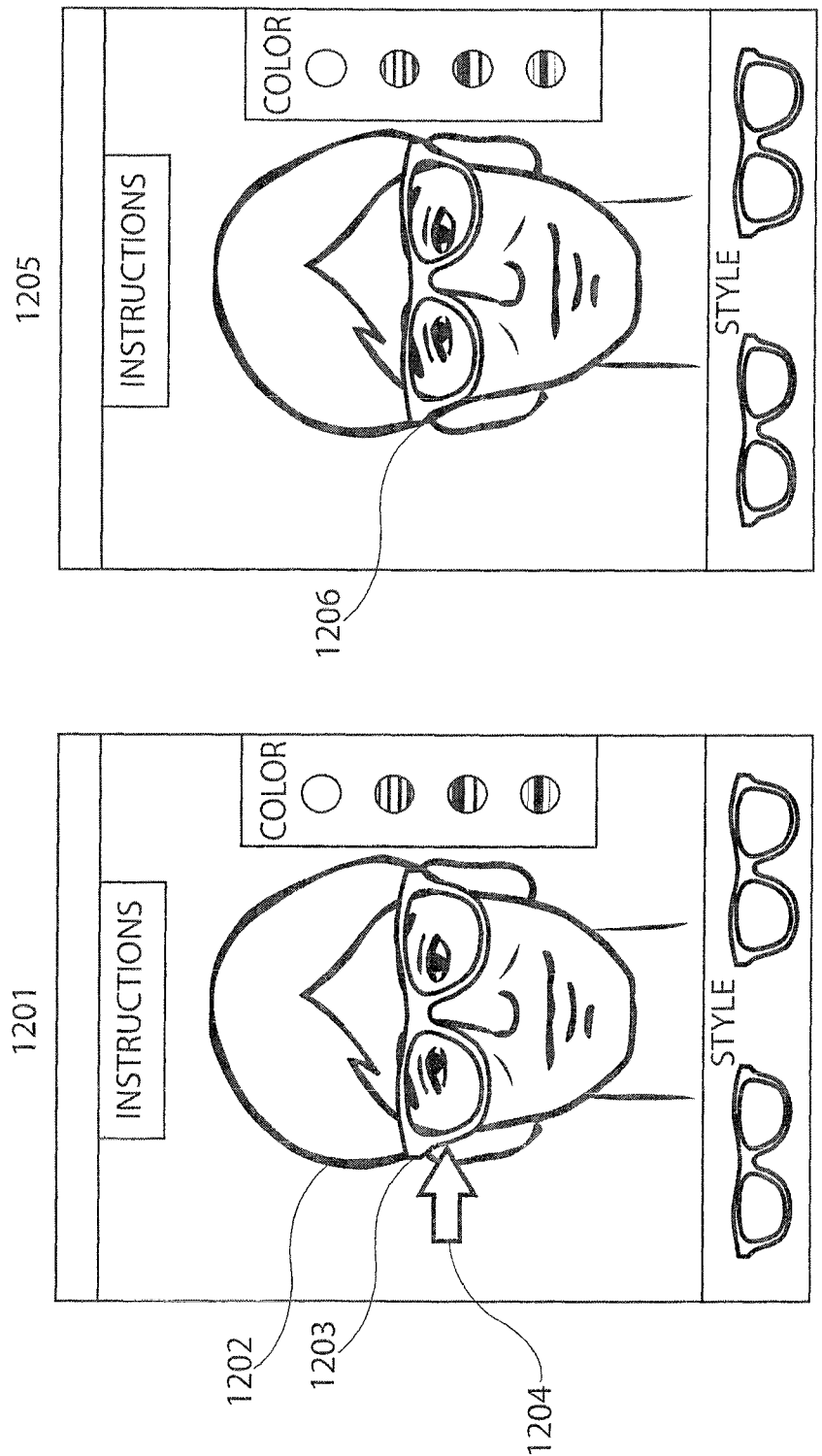
FIG. 12 is a diagrammatic illustration of an example illustration showing the custom adjustment of the width of eyewear with a computer system an interface to be able to ascertain the product placement on the face of the individual as well as improvements that can be made at the time that improve representations of the individual.

FIG. 12 shows an example computer interface 1201 for adjusting eyewear 1203 previewed on user 1202. The base designs consist of a variety of styles or materials, including but not limited to fully-rimmed, semi-rimmed, rimless, plastic, or metal. The controls include but are not limited to:

control points on the eyewear that can be dragged or adjusted, sliders that are linked to certain features, directly drawing on the frame, and touch, gesture, mouse, or other interaction to stretch or push/pull features of the frame. In one embodiment, the controls allow the user to change certain limited features, including but not limited to the nose pad width, the temple length and height, and the width and height of the front of the eyewear. For example, if user 1202 in FIG. 12 has a narrow face, he adjusts the eyewear 1203 to make the overall size of the eyewear narrower. The user selects the eyewear 1203 with the computer system input device, and moves the edge of the eyewear inward toward his face as indicated by the arrow in FIG. 12. The resulting modified eyewear 1206 is shown in the updated preview 1205. The ability for the user to make such easy and custom adjustments to eyewear before purchasing represents a major change in the way the eyewear products are purchased from the current state of the art. The feedback may be nearly instantaneous, with the user seeing the rendered preview updated on the computer system display.

In one embodiment, constraints are used to limit the customization within bounds that are predefined with the configurable model. The parametric design and constraints of the model may be used to limit feature adjustment to preserve each eyewear's base design while making the process simple for the user to achieve custom fitting and sizing. While some use cases may have advantage of giving the user 100% control over the design, there is a distinct advantage to limiting the adjustment so the user can easily obtain an aesthetically pleasing and manufacturable product. For example, without any constraints, the user may accidentally make a self-intersecting or highly asymmetrical or jagged, unappealing design that would neither fit nor look good. In addition to built-in constraints, controls such as control point, arrows, etc) may be highlighted only on the areas that are adjustable, or they highlight as the user moves their input device over the areas, or there are instructions explaining what portion(s) of the eyewear they can alter.

In another embodiment, the user has fewer limits in what he can adjust while still preserving the overall eyewear design. For example, the computer system enables the user to grab and adjust any part of the eyewear, giving controls to adjust length, height, width, and thickness of any portion of the eyewear, as well as the curvature of various members such as the rims and temples. FIG. 13 illustrates an example base eyewear design 1301. A user directing a computer system input device selects a point on the eyewear at 1305 and move along the dotted line in the direction of the arrow 1306 to point 1307. The eyewear 1302 would then be modified in the region 1308 that was edited. To retain symmetry while simultaneously reducing the number of steps necessary to customize eyewear, a change on one side of the eyewear is equally applied to the other side of the eyewear, as shown in updated eyewear 1303.

User Adjustments without Direct Editing

In another embodiment, the computer system may ask the user questions to help guide him to or through adjustments. For example, the computer system may ask, "Is the eyewear currently too wide or narrow on your face?" or "Is the eyewear currently too thick or thin?" or "Do you prefer larger or smaller styles?" The user would be able to select an option or answer the prompts through the interface and then subsequently observe an adjustment to the eyewear in response. When coupled with machine learning techniques described herein, this could represent a powerful means to provide a personalized and custom recommendation, while allowing slight adaptation based on live feedback from the user.

In another embodiment, the computer system alerts the user to certain key areas to adjust, including but not limited to the nose pads and temples. The nose and top of both ears are the three key contact points that must fit well, and each ear may be at a different height. The computer system may ask the user to inspect these particular areas and adjust as needed. For example, the user may adjust the length of the temples until they fit well over the ears, or adjust the temple angles independently to correspond to his differing ear heights such that the front frame of the eyewear sits ideally and aesthetically level on his nose.

In another embodiment, the user may adjust, modify, reposition, or select new eyewear designs in real-time on a preview of their image data. As previously described, a real-time preview is provided, and the user is given control over modifying the eyewear design in real-time.

Improper Fit

Referring back to FIG. 1B, step 111, describes the computer system detecting when a potentially improper or uncomfortable fit exists or if a design has been created that is not possible to order. These undesirable configurations may result from the user's interaction and customization of their model, and they may not be aware of how their changes affect the model. For example, if the temples are required to flex too far to accommodate the user's face, they are uncomfortable due to the pressure applied to the sides of the user's head. The pressure on the user's head is calculated based on the hinge design properties, the degree of hinge and/or temple deformation, and the distance from the hinge to where the temples contact the user's head. In another example, the nose pads are too tight on the nose or too lose and the eyewear may slip. There may be an absolute interference than can be detected by the computer system. An analysis of the anatomic model and configurable eyewear model can detect surfaces that interfere. The pressure on the nose pads is calculated based on the face and eyewear geometry and the material properties of the eyewear. A warning or automatic adjustment to the design is provided if the pressure is determined to be too high. Additionally, the lenses may be positioned at a non-optimal angle such that the user would have a poor visual experience or sub-optimal visual acuity. The computer system analyzes the following criteria, among others, between the 3D eyewear model and the quantitative anatomic model to ensure a proper fit on the user: Interference or gap between the nose pads and nose, Interference or gap between the top of the ears and temples, Angle of temples (inward or outward) needed to fit to the ears, Angle of lenses, and Position of eyewear on nose and position of eyes relative to lenses (e.g. are the eyes well centered within the lenses?)

The computer system couples the dimensional information with material properties, force and deformation calculations, and computational simulation of stress/strain. Specifications may exist for each metric analyzed and if a criterion is not met, the user is alerted. Alternatively, the computer system automatically suggests an alternative or set of alternatives.

Custom Finishes

In an exemplary embodiment, the computer system provides the user with controls to change the color, finish, texture, or material of the eyewear. The user's control of these options may occur without automated recommendations from the computer system or they user may be given control after the computer system makes an initial custom design. The computer system displays a plurality of colors that is previewed on or applied to the eyewear. The user selects different colors for various portions of the eyewear. The color selection may be limited to a set of colors/finishes established by the manufacturer or there is a plurality of hundreds, thousands, or more colors/finishes. The user also selects options for material finish to preview. Examples of finishes that is selected and rendered include polished, brushed, satin, clear coat, gloss, matte, embossed, hammered, grained, etc. User changes and editing of the eyewear may happen in an editing interface with updates applied to the preview view, or said changes and edits are applied and previewed in real-time.

In another embodiment, the user take a photo of an object such as clothing, nail polish, pictures, etc. The user provides the photo as a digital image or uses the computer system to take the photo. The user selects a point or region of the photo for the computer system to match the color or pattern. The photo is analyzed by the computer system and a custom color or pattern is specified from that image. The computer system may require a calibration standard to be employed to obtain high accuracy in color matching and reproduction. The calibration standard is a printed card with a variety of calibrated colors and shades on it that the user must include in the image. The manufacturer may supply this card to the user, or the user prints it. The computer display may also be presented next to the object with a color that is desired. The display may have a color calibration pattern displayed on it, which could be captured along with the object in a mirror or using a second image-capture device. Alternatively, the user is prompted to include a known object in the photo. The known object would be an item that was calibrated and stored in the computer system. Examples may include ubiquitous logos that are known to be professionally-printed with a high-degree of color accuracy and consistency, such as a logo on a food box or magazine, soda cans, currency, or credit cards. Alternatively, the computer system may have a database of known colors from other manufactures, such as makeup, paint samples, automobiles, or fabrics—a user is able to select the color of her favorite shirt, car, or nail polish color from said database and the manufacturer would then have the color information necessary to accurately reproduce and match the intended color.

In another embodiment, the eyewear is customized with a pattern, image, or text from the user. The pattern, image, or text will herein be referred to as pattern. The pattern is printed, engraved, etched, painted, or otherwise applied to any surface of the eyewear. The pattern is generated from a library of available options on the computer system, provided by the user from her image similar to the previous description of custom colors, or entered by the user. For example, the user may want to print his name inside the temples. Or he may desire to etch a design of lines on the side of the temples or print a textured pattern of leaves on the eyewear. The pattern is rendered and previewed to the user on the 3D eyewear model, and subsequently accurately reproduced on the manufactured eyewear.

In another embodiment, the eyewear is customized with accessories, including but not limited to logos, charms, jewels, etc. For example, a base design may have an option to place an accessory on each temple near the hinge. There is a default accessory, and the user may elect to change, reposition, or remove it. The user may select from a plurality of options including a variety of shapes, colors, materials, etc. The accessories are rendered by the computer system to display on the 3D eyewear model for the user to preview.

Preference Records

In an exemplary embodiment, once the user has selected eyewear and adjusted its size, color, and other features, these preferences are recorded and stored to a non-transitory computer readable media. The user's models, image data, and other information are also stored by the computer system. When the user selects alternate eyewear designs, such as a different material or different style, the eyewear is adjusted to their preferences based on their past interactions and preferences, therefore making the experience of browsing through eyewear more customized while also reducing repetitive tasks. For example, one the desired fit preferences are established, any design or style can be updated to fit the user according to their preference. If they like eyewear that is slightly smaller than the width of their face and they like to wear it further from their eyes, then all the styles could be adjusted to that preference. In another embodiment, the preferences for a specific user are refined as he uses the computer system. As previously described in the method to build the training database of preferences, the computer system records and track a user's preferences as he shops and previews eyewear. This information is used to refine his preferences and add to the information he entered or was previously analyzed from his supplied image data. The user's stored preferences may also be used to build a larger database for future prediction and customization of new users, as mentioned previously.

As the user and/or computer system adjusts the eyewear, the magnitude and direction, when relevant, of the change is recorded by the computer system. The configurable eyewear model is updated by adjusting the appropriate model parameter by an amount to match the change requested by the user. Any constraints programmed into the model are checked and if a limit is exceeded, then the computer system provides a warning to the user. Alternatively, the change is applied up to the limit and any excess change beyond the limit is ignored or disallowed (with or without warning the user of the limit exceeded). For example, if the user changes the width of the eyewear from 140 mm to 190 mm, but the maximum design width is limited to 170 mm, then the eyewear would adjust only to the maximum 170 mm, and the user is notified of reaching this limit. An updated model is rendered and displayed by the computer system as previously described such that the user can preview the new 3D eyewear model on his image data. In another embodiment, the changed area of the eyewear is highlighted or identified to the user for a period of time or until he accept the change. The user is provided with a provision to undo (or redo) any changes he requested.

Efficiency of Configuration

As users or the computer system request changes to the configurable model to fit different users, it may desirable to have a plurality of custom designs that are preconfigured for efficiency. For example, hundreds, thousands, or millions of configurations of a design could be pre-configured and stored on a computer system or network-accessible computer system. If these pre-staged configurations span the most commonly accessed design configurations, then they can be quickly accessed and displayed to the user. Alternatively, a shape matching algorithm, look-up table, or other techniques are used to find the model that is closest to the user's preferences. Subsequent minor adjustments are then made from the pre-staged configuration to fine tune the configurable model to the exact user preferences.

Preparation for Manufacturing

As illustrated in FIGS. 1A at 17 and 1B at 115 and 116, the computer system stores data to represent the user's preferences and designs, and subsequently calculates a price and shipping estimate. After a user determines the final custom eyewear he wants to order, the computer system may generate a final representation that is more photo-realistically rendered and of higher quality and resolution if the original preview images were made to a lower quality for efficiency. The computer system provides to the user a price, expected shipping date, and other information prior to the completion of the order for his custom eyewear. The representation may consist of the various parameters and settings selected by the user or a final 3D model of the eyewear. The computer system transfers the eyewear representation and preferences, dimensions, configuration data and other information via a network connection or other means of information transfer to another computer system accessible by the manufacturer. In addition to the eyewear representation, the computer system may also receive the user's personal information, payment details, shipping address, image data, and any other information needed to complete the order.

In order to provide an estimated shipped date and price, the computer system actively tracks a number of parameters, including but not limited to: an inventory of all raw materials needed, current production capacity, work in progress, future schedules, orders scheduled, and lead times on materials or production capacity, etc. The computer system performs scheduling and shipping estimates to provide the user with an expected delivery date or provides the manufacturer with actions needed to achieve a guaranteed delivery date for the user.

Manufacturing Custom Products

FIG. 1B at 114 illustrates the user's decision to purchase eyewear. FIG. 1A at 18 and FIG. 1B at 116 and 117 describe analyzing and preparing information and files for eyewear and lens manufacturing. The final eyewear representation, preferences, dimensions, configuration data, once in the manufacturer's computer system, are analyzed to create both a manufacturing work order and set of manufacturing CAD, CAM, CNC, or other manufacturing and modeling files automatically. A serialized identifier linked to the user's order is created to track the eyewear as it moves through the production process. The computer system associates the serial number with raw materials, specifications, or quality checklists. The computer system also prepares manufacturing files depending on the method of manufacture needed for the particular eyewear model, including but not limited to: model files for rapid prototyping or additive manufacturing methods; model files converted into tool-path CNC code for machining (e.g. g-code), routing, milling, or other subtractive manufacturing methods; model files converted into flat patterns for photo-etching; model files converted into flat patterns with tool-path or robotic control code for laser-cutting; laser-marking/etching, water jet cutting, stamping (and stamp tool production), punching (and punch tool production), or other 2-D cutting methods; model files converted into rapid prototyping or additive manufacturing methods of an inverse geometry to create a mold for injection molding, casting, or other tool production, and model files converted into robotic control instructions for part handling, polishing, assembly, drilling, cutting, etc.

The computer system also prepares manufacturing files depending on prescription information, lens material, and user information converted into lens surfacing, lens laser-marking, and lens edge machining instructions for lens manufacturing; Parameters entered by the user for updating existing manufacturing files for any of the above-mentioned methods; Colors and patterns to be painted, anodized, deposited, plated, stamped, printed, etched, embossed, or otherwise used to change the visual appearance of the eyewear; and in general, quantitative information specified from the user's order automatically converted into files or instructions for manufacturing equipment.

Figure 15:
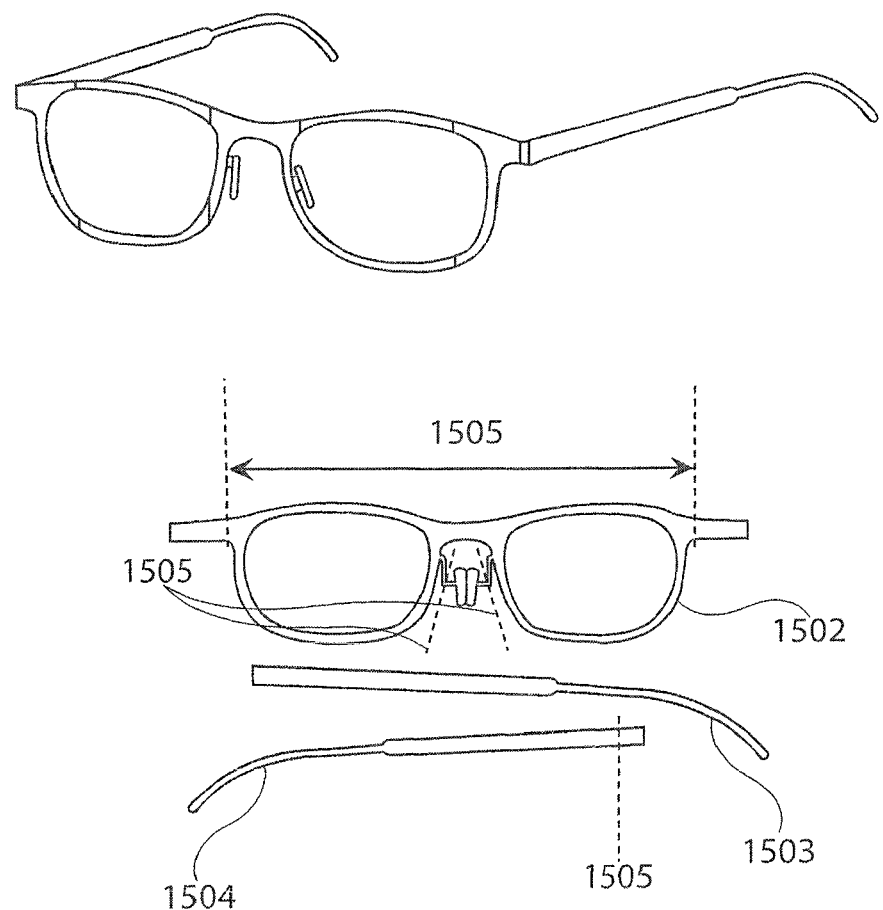
FIG. 15 is a diagrammatic illustration of an example of a custom 3D eyewear model converted to flat patterns for manufacturing.

FIG. 15 shows an example of a 3D eyewear design 1501 that is automatically converted into flat patterns of the front 1502, left temple 1503, and right temple 1504 to prepare for laser cutting or machining out of sheet metal or plastic. These parts, along with other parts from other orders, are automatically arranged to optimize manufacturing metrics such as the minimizing of material usage or process time. The flat patterns also contain geometric information regarding bend locations 1505 to be used by manufacturing equipment to bend or form the pre-cut parts. The pattern is stored as a digital file or other media needed to provide the manufacturing equipment with dimensions and instructions. Subsequent operations may include bending, folding, or other forming operations performed on automated equipment. The manufacturing system may use the serialized identifier to determine what operation to perform on the part or to obtain the specifications for the part at each step. Bend patterns or other computer-readable instructions are provided to the equipment.

Figure 16:
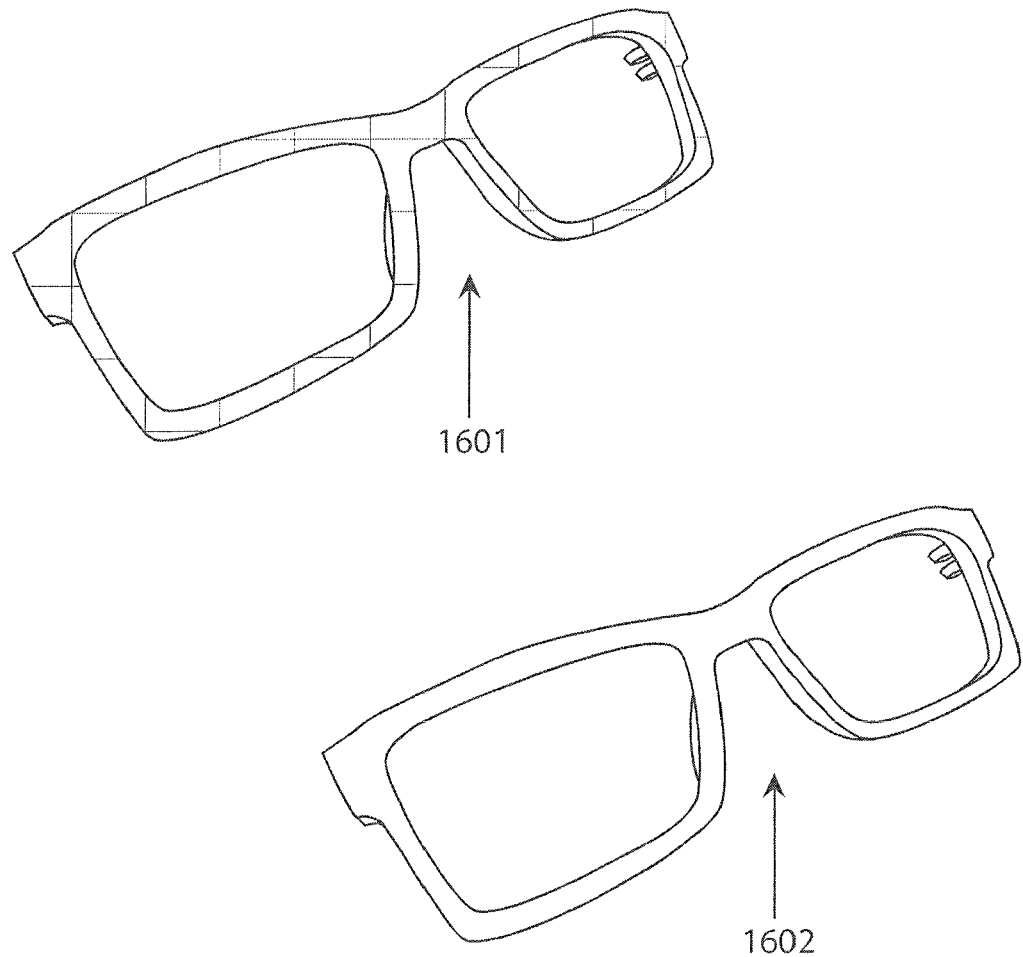
FIG. 16 is a diagrammatic illustration of an example of a custom 3D eyewear model and manufactured part.

FIG. 16 shows an example of a 3D parametric eyewear model 1601 that was customized for a user and the resulting manufactured part 1602 that was produced. Parts such as these are created using any of the previously mentioned manufacturing technologies or other methods known to those familiar in the art.

As to manufacturing, FIG. 1B, step 117, describes the computer system controlling manufacturing equipment and personnel. The computer system may sequence a plurality of manufacturing equipment, aided or unaided by humans. As an illustrative example, the computer system may provide a set of instructions to perform the following sequence to make a metal eyewear frame:

Instructions for robot to pull required material and supply it to a laser-cutting machine or a CNC machine. In parallel, instructions sent to lens manufacturing equipment to surface, polish, mark, coat, and edge lenses. Instructions and tool path for laser cutting machine to cut shape of eyewear and mark with logo or other decorative marking. Instructions for robot to transfer lasercut part to bending and stamping machine. Instructions for bending and stamping machine to shape eyewear to desired final shape. Instructions for robot to transfer part to polishing machine. Instructions for polishing machine to finish part. Instructions for painting, coating, anodizing, printing, or coloring the eyewear. Instructions for robot to sort finished parts and associate eyewear and lenses. Instructions for human operator to assemble eyewear and lenses, nose and ear pads, and perform final inspection. Instructions for robot to package and label finished product for shipping.

Figure 32:
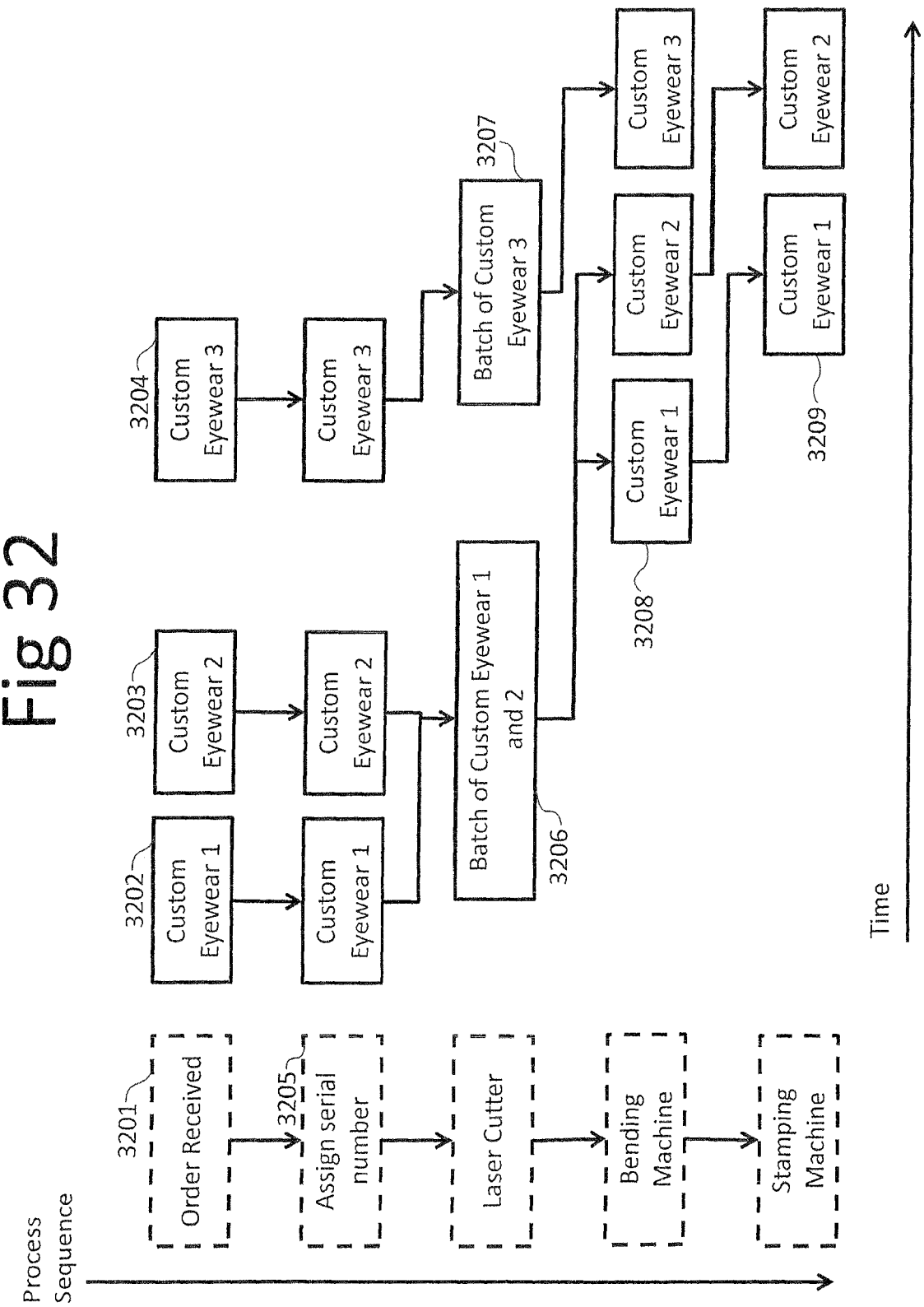
FIG. 32 is a block diagram of a manufacturing sequence for custom one-up products.

The previously mentioned instructions are one sequence for one custom product. To enable successful manufacturing of multiple custom products, the computer system controlling the manufacturing process creates a sequence of commands for each stage of the process for each custom part being produced. FIG. 32 illustrates a block diagram showing a process flow for custom one-up products. Starting at 3201, orders are received over time for custom eyewear 1 at 3202, custom eyewear 2 and 3203, and custom eyewear 3 at 3204. After the orders are received, each eyewear receives a serial number at 3205. The computer system groups the parts into batches 3206 and 3207 for laser cutting based on machine availability, open orders, shifts, and other data. The computer system provides instructions to the laser cutter for each batch to cut the parts. So while a custom product moves from the laser cutter to the next step, the laser cutter receives instructions for the next batch of custom products. After laser cutting, the computer system provides a sequence of instructions for each part, one after the other, to a bending machine 3208. As each part finishes on the bending machine, the computer system provides instructions to a stamping machine 3209.

In one embodiment, the computer system generates instructions for quality control or inspection. The computer system creates templates for human inspectors to use, dimensions or pass/fail criteria for inspections. Since each part is unique and one-up, creating unique inspection criteria is important. The computer system may also provide instructions to automated inspection consisting of the dimensions, properties, or criteria for each individual product. Additionally, the computer system may provide data or a model of the user's anatomy to manufacturing equipment to produce an inspection or assembly fixture. For example, a 3D printed model of the user's ears and nose may be generated to ensure the final product model fits appropriately with the user.

Subcontractors or multiple manufacturing sites may be used in any of the preceding steps, and the computer system in one embodiment automatically handles the preparation of order information and/or manufacturing instructions/schematics. Finally, in step 118 of FIG. 1, the custom eyewear is shipped to the user.

Alternate Shopping Systems

The following embodiments describe alternate or additional systems and methods to supplement or enhance the previous description.

In-Store System

Figure 26:
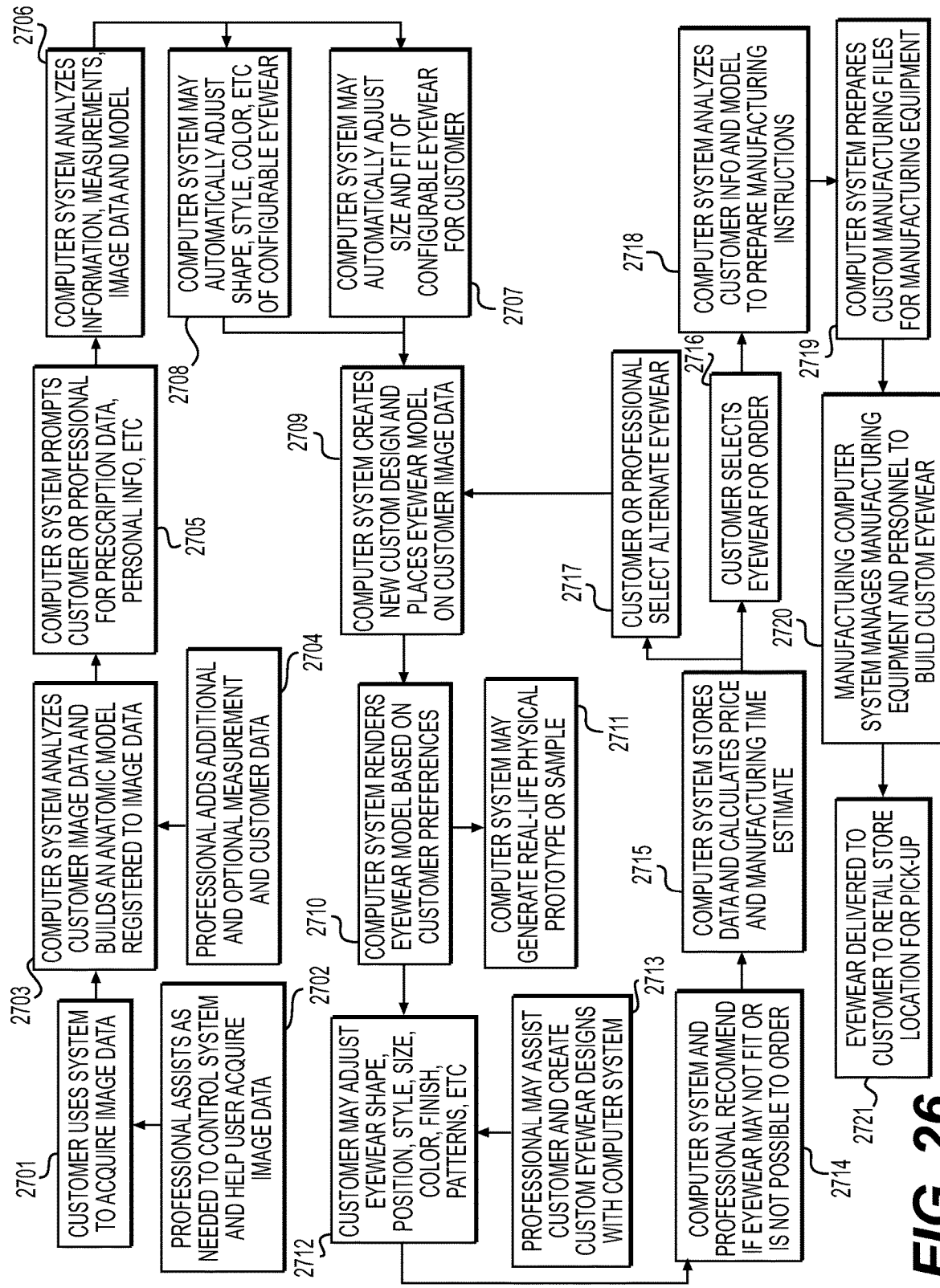
FIG. 26 is a block diagram of an in-store custom eyewear shopping method.
Figure 27:
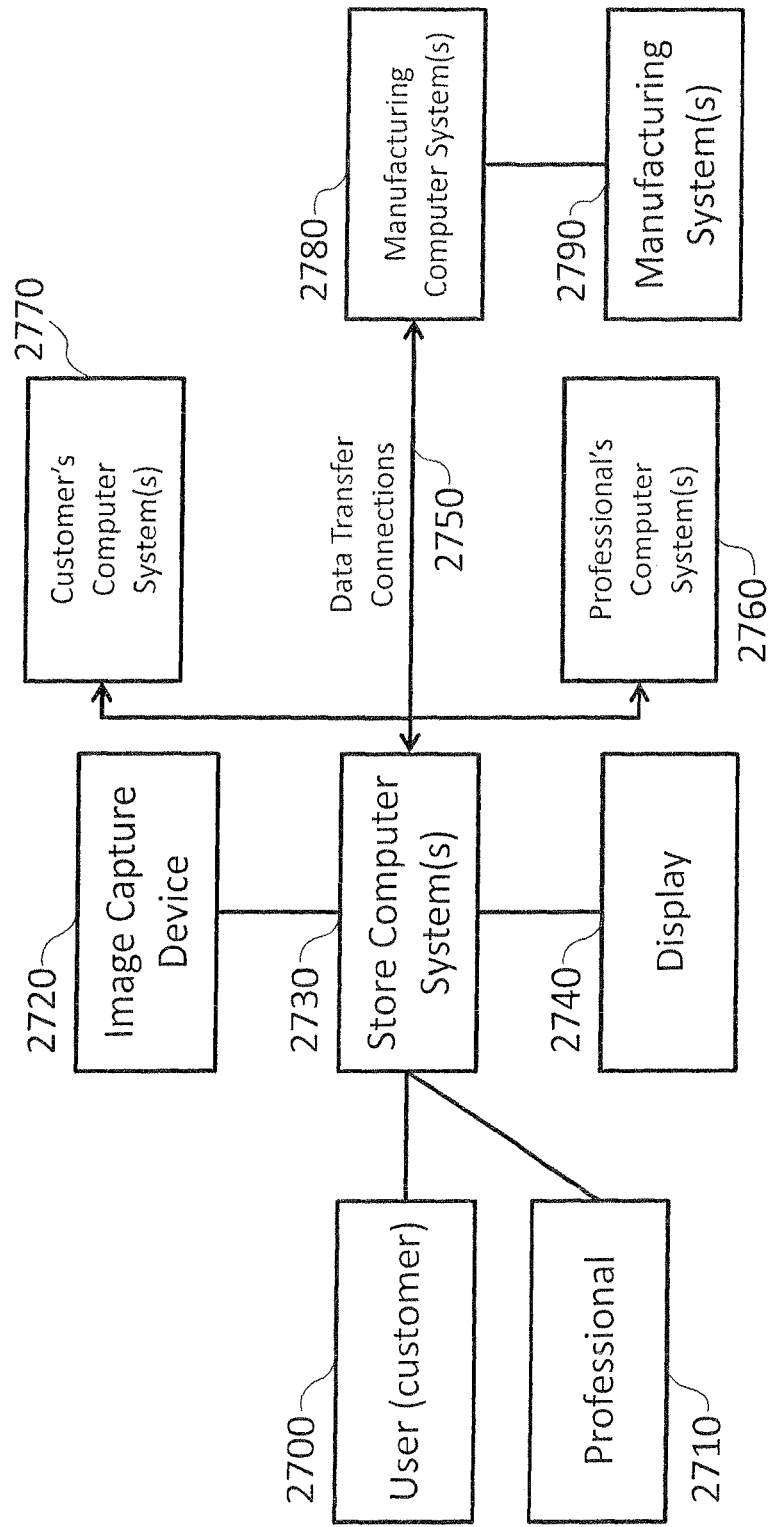
FIG. 27 is a block diagram of an in-store custom eyewear shopping system.

The method and system described to create custom products and eyewear is useful to have within a retail store, optometrist office, or other physical location. The system and method in part or in whole is controlled by an a customer, optician, optometrist, sales-person, or other professional assisting a user with the selection and purchase of the best frame and lenses in an office or retail location or through remote assistance through a computer network. FIG. 26 illustrates an exemplary method of shopping for custom eyewear with a system in a store. FIG. 27 illustrates an exemplary computer system. The in-store computer system 2730 is used by customer 2700 with optional assistance by an in-store or remote professional 2710. The computer system 2730 is configured with an image capture device 2720 and display 2740. The computer system optionally has calibrated imaging devices to measure color for custom color matching an object of the user's for the custom eyewear material. The in-store computer system is configured with a data transfer connection 2750 to the manufacturer's system 2780 and 2790 and optionally to the computer's computer system 2770 and the professional's store computer system 2760, which may contain the user's information, info, prescription, etc.

If the process was started at the professional's store or office, the user's personal computer system has access to the user's image data and eyewear inventory after a session with a professional, so the user could access this information at a later time. For example, they could continue shopping at home after getting the initial model and customization setup completed at the store. The computer system may also be configured to work with optometry devices to measure prescription information and automatically incorporate the measurements into the computer system such that no manual entering of prescription data is needed. A further advantage of an in-store system is the ability to create a more controlled and higher-quality image capture and display system. With a kiosk or computer system designed specifically for the purpose of capturing image data and displaying custom previews, more advanced for specialized hardware components could be used, such as multi-camera systems or depth sensing cameras with calibration.

FIG. 27 illustrates an exemplary method. In this embodiment at 2701, a computer system configured with a camera or imaging device is used to acquire image data of a user. The computer system may optionally be further configured with reference targets, multiple or calibrated imaging devices, depth devices, wearable reference targets such as eyewear, or calibrated distances and positioning devices to ensure the scale of the user is measureable by the computer system. At 2702, the store or office professional may assist the customer with using the computer system and acquiring image data. At 2703, the computer system reconstructs an anatomic model of the user's face based on the image data. At 2704 and 2705, the computer system optionally has an input device that enables a store professional, doctor, or other person to input additional anatomic data, such as physical measurements, prescription information, etc. The computer system computer system automatically configures or adjusts custom eyewear models the user for size and fit 2707 and style 2708. At 2709, the computer system creates custom products and co-registers the anatomic model with the original user images such that the model coordinates and camera position align the face model with the pose, position, and scale of the images of the user's face. At 2710, the computer system aligns an eyewear model with the user model and images and render a preview of eyewear models on the images of the user. At 2711, the computer system optionally has or connects to a rapid prototyping system (3D printer, CNC cutter, etc) to create a physical prototype or preview for the user. At 2712 and 2713, the computer system has input devices that enable the user or store professional to adjust, update, or configure the custom eyewear models. the computer system has an input device to enable a user or store professional to select and try various eyewear models. At 2714, the computer system, and optionally the professional, may recommend if the eyewear is not well suited to the customer. At 2715, the computer system calculates data about price and manufacturing time. At 2717, the user or store professional to select and try various eyewear models. At 2716, the customer may select to order the custom eyewear. At 2718, the computer system transfers the final eyewear model and user information to a manufacturer's computer system via a network connection or other form of electronic communication such that the manufacturer can produce the custom eyewear. At 2719 and 2720, the manufacturer's computer system and manufacturing system pre-process the eyewear model and information and produce custom eyewear. At 2721, the custom eyewear is completed and shipped to the customer or is ready at the store location for pick-up.

Sharing Data and Design Access

In another embodiment, the user provides access to his image data and anatomic model to another party, such as a friend, family member, eye care professional, or fashion consultant. The user enables the computer system to transfer their image data, and optionally other information such as preferences, eyewear models, and settings over a network or data transfer technology to another computer system. This transfer is done with a hyperlink, authenticated login, or other mechanisms that are sent directly to another person through one of a variety of communication forms, such as email, digital messages, social networking, cloud storage, etc. The other party then adjusts, customizes, and previews eyewear on the original user's face model or image data. The other party then saves favorites and eyewear designs and then sends back images, designs, views, customizations, suggestions, notifications, etc to the original user. The original user then uses his computer system to preview the eyewear designed and fitted for him by the other party. This embodiment has a huge advantage of allowing the user to crowdsource the design of their eyewear to other people, potentially magnifying the diversity and quality of the designs they receive for previewing. In this case, they have both the power of computer-driven algorithms and human-driven design.

In an exemplary embodiment, the user sends a plurality of image data or interactive models of himself with previews of eyewear. The image data or models is sent from the user's computer system to another computer system via a computer network of other information transmission system through one of a variety of communication forms, such as email, digital messages, social networking, cloud storage, etc. The computer system then allows an authorized person or people to provide responses, ratings, messages, and other forms of feedback to the original user.

In another embodiment, the system is used by eyewear designers or fashion brands to create their own lines of eyewear. A large start-up cost exists for building a new line of eyewear since parts must be ordered in bulk from traditional manufacturing methods, high-fidelity prototypes are expensive, and many combinations of styles, sizes, and colors must be ordered and held in inventory before any sales are made. The system described herein could be used by a designer to create a set of designs with varying colors, shapes, sizes, and other features. A database full of user image data, anatomic models, and preferences provides an extraordinary means to test and preview eyewear across a large sample of people. Samples of the designs may be provided and as users view and want to order the designs, an on-demand manufacturing and delivery method could be used so the designer or fashion brand would never need to carry inventory.

In another embodiment, the system may be used without the image analysis portion if an eyecare professional takes physical measurements and uses the computer system and to enter anatomic data about the user into a system that generates custom designs with configurable eyewear models. The professional or user may then provide preferences and refinements and have the eyewear manufactured as previously described.

Additional Products

In another embodiment, all the methods and techniques described herein are applied to the customization, rendering, display, and manufacture of custom eyewear cases. A user could select from a plurality of materials, colors, designs, shapes, and features and see an accurate rendering of the case on his display. Moreover, the case can automatically be sized to fit the custom eyewear designed such that there is not an excess of free space within the case that would allow the eyewear to bounce around—the case can be automatically designed to custom fit the eyewear such that it minimizes the size of the case and increases the case's ability to protect the eyewear in transport. The case color, style, and materials, and method of manufacture can also be matched to those used to make the custom eyewear. Custom text, such as the name of the user, is engraved or marked on or in the case. The same eyewear manufacturing techniques described herein can also be used to manufacture the custom cases.

Figure 33:
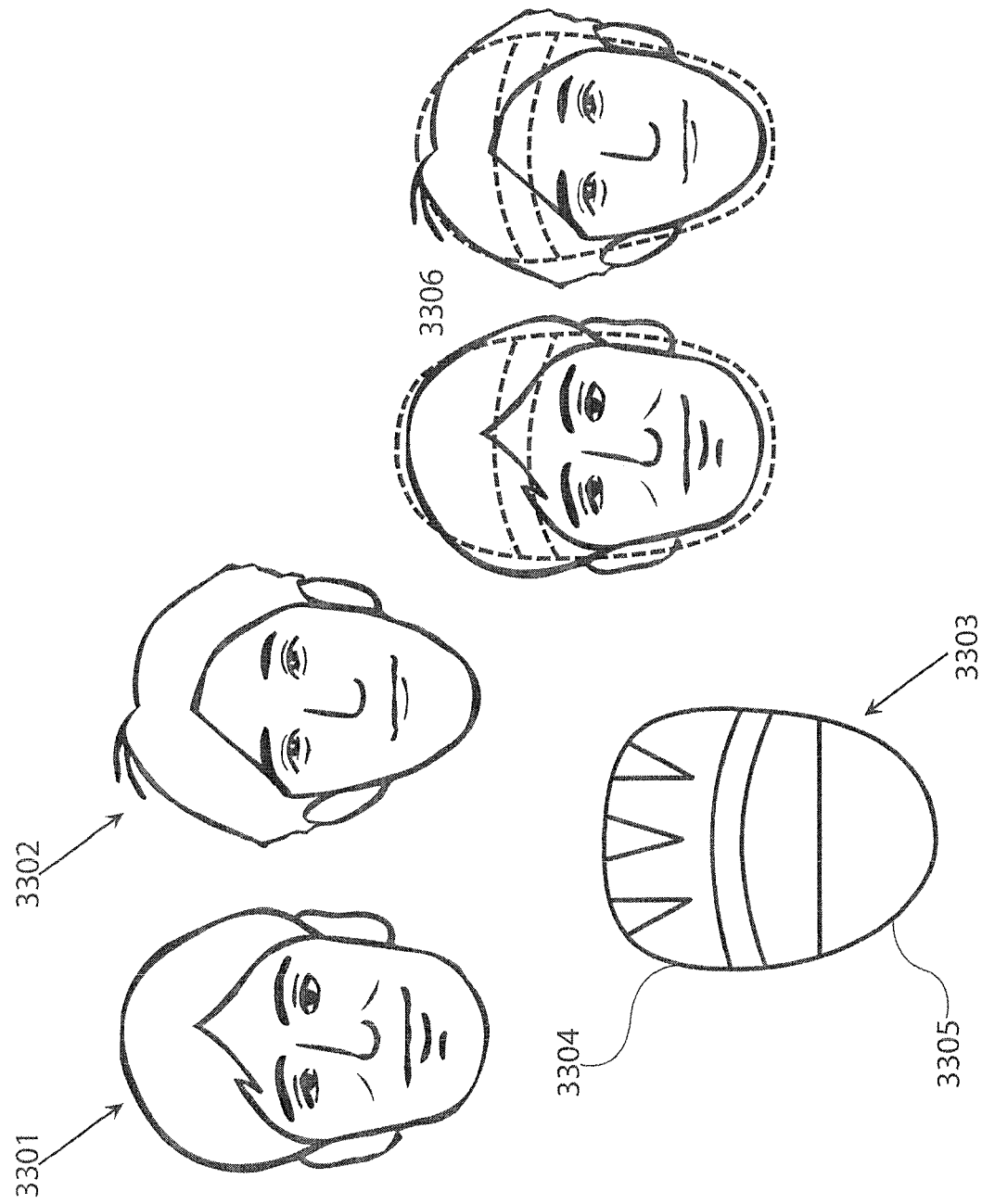
FIG. 33 is a diagrammatic illustration of creation of a custom helmet.

Those skilled in the art will recognize that the systems and methods described herein may also be used in the customization, rendering, display, and manufacture of other custom products. Since the technology described applies to the use of custom image data, anatomic models, and product models that are built for customization, a multitude of other products is designed in a similar way, for example: Custom Jewelry (e.g. bracelets, necklaces, earrings, rings, nose-rings, nose studs, tongue rings/studs, etc), Custom Watches (watch faces, bands, etc), Custom Cufflinks, Custom Bow Ties and Regular Ties, Custom Tie Clips, Custom Hats, Custom Bras, Inserts (pads), and other undergarments, Custom Swimsuits, Custom Clothing (jackets, pants, shirts, dresses, etc), Custom Baby Bottle Tips and Pacifiers (based on scan and reproduction of mother's anatomy), Custom Prosthetics, Custom Helmets (motorcycle, bicycle, ski, snowboard, racing, F1, etc), Custom Earplugs (active or passive hearing protection), Custom Audio Earphone (Headphone) Tips (over-the-ear and in-ear), Custom Bluetooth Headsets Tips (over-the-ear or in-ear), Custom Safety Goggles or Masks, and Custom Head-Mounted Displays As an example embodiment of another product, the following system and method describe a custom helmet product. Refer to FIG. 33.

In accordance with an embodiment, methods are disclosed for creating custom helmets. One method includes acquiring, using at least one computer system, image data of a user (two users with different head shapes are shown at 3301 and 3302); determining, using at least one computer system, anatomic details and/or dimensions of the user; configuring (eg, custom shape, size, dimensions, colors, finish, etc), using at least one computer system and anatomic data of the user, a new custom helmet model for the user (a configurable helmet model 3303 is shown with protective element 3304 and strap 3305); applying, using at least one computer system, a configurable helmet model to the image data or anatomic model of the user; previewing, using at least one computer system, images of the user with the configurable helmet model (custom helmet models 3306 are shown on the users, adapted to their unique head shapes); optionally adjusting and updating the preview, using at least one computer system and/or user input, the configurable helmet model properties (eg, custom shape, size, dimensions, colors, finish, etc); preparing, using at least a computer system that executes instructions for manufacturing the custom helmet based on the previewed model; and manufacturing, using at least one computer system and manufacturing system, the new custom helmet.

In accordance with an embodiment, systems are disclosed for creating a custom helmet. One system includes an image acquisition device configured to obtain image data of a user;

an input device configured to receive instructions from a user; a display configured to display image data to a user; a manufacturing system configured to produce a custom helmet; a digital storage device to store instructions for creating and previewing custom helmet; a processor configured to execute the instructions to perform the method including: acquiring, using at least one computer system, image data of a user; determining, using at least one computer system, anatomic details and/or dimensions of the user; configuring (eg, custom shape, size, dimensions, colors, finish, etc), using at least one computer system and anatomic data of the user, a new helmet model for the user; applying, using at least one computer system, a configurable helmet model to the image data or anatomic model of the user; previewing, using at least one computer system, images of the user with the configurable helmet model; optionally adjusting and updating the preview, using at least one computer system and/or user input, the configurable helmet model properties (eg, custom shape, size, dimensions, colors, finish, etc); preparing, using at least computer system, instructions for manufacturing the custom helmet based on the previewed model; and manufacturing, using at least one computer system and manufacturing system, the new custom helmet.

What is claimed is:

1. A computer-implemented method for configuring a parametric model of an eyewear product, the method comprising:
capturing image data and/or measurement data of at least a portion of a user's anatomy;
generating an anatomic model of the at least the portion of the user's anatomy and the parametric model of the eyewear product based on the captured image data and/or measurement data;
determining, using the anatomic model, an interpupillary distance, a vertex distance, a pantoscopic tilt, a frame wrap, or a combination thereof based on the user's anatomy to automatically update one or more geometric parameters of the parametric model;
determining prescription information, wherein an estimated average of prescription lens is calculated upon determining an absence of the prescription information; and
generating a presentation of: (i) the updated parametric model with instructions for manufacturing a physical embodiment of the eyewear product according to the updated parametric model and (ii) lenses of the updated parametric model at a particular size, shape, and thickness based on the estimated average of the prescription lens.

2. The computer-implemented method of claim 1, further comprising:
receiving one or more inputs from the user to adjust at least one configurable portion of the updated parametric model; and
modifying the at least one configurable portion of the updated parametric model based on the one or more inputs, wherein the instructions for manufacturing the physical embodiment of the eyewear product is further based on the modified configurable portion of the updated parametric model.

3. The computer-implemented method of claim 2, further comprising:
automatically modifying a frame portion of the parametric model in response to a modification to lens portion of the parametric model; or automatically modifying the lens portion of the parametric model in response to a modification to the frame portion of the parametric model.

4. The computer-implemented method of claim 1, further comprising:
optimizing one or more parameters of the parametric model based on pre-defined fit metrics, wherein the pre-defined fit metrics include an optimal ratio of eyewear product's width to a width of a user's face, an optimal centering of eyes within lenses of the parametric model, or a combination thereof.

5. The computer-implemented method of claim 1, wherein determining the prescription information further comprising:
receiving, via a user interface, the prescription information pertaining to the eyewear product associated with the user; and
rendering the lenses of the updated parametric model at the particular size, shape, and thickness based on the prescription information.

6. The computer-implemented method of claim 1, further comprising:
configuring the anatomic model to adjust to a plurality of facial expressions of the user based the image data, wherein the image data includes the plurality of facial expressions of the user; and
determining placement, design optimization, and adjustment of the parametric model that fit across the plurality of facial expressions based on the configured anatomic model.

7. The computer-implemented method of claim 1, wherein the interpupillary distance includes a binocular interpupillary distance that indicate distance between pupils, a monocular interpupillary distance that indicate distance between a center of a user's nose and at least one pupil, or a combination thereof.

8. The computer-implemented method of claim 1, wherein the vertex distance indicates a distance from a center of a user's eyes to inner surface of one or more lens of the eyewear product.

9. The computer-implemented method of claim 1, wherein the pantoscopic tilt indicates an angle for one or more lens of the eyewear product with respect to a user's face.

10. The computer-implemented method of claim 1, wherein the frame wrap indicates a curvature of a frame of the eyewear product around a user's face.

11. The computer-implemented method of claim 1, wherein the instructions for manufacturing is based on a manufacturing metric associated with manufacturing the physical embodiment the eyewear product, and wherein the manufacturing metrics includes production capacity, inventory of raw materials, lead times on the raw materials, schedules, product specifications, or quality checks.

12. A system for configuring a parametric model of an eyewear product, the system comprising:
a data storage device storing instructions for creating a customized eyewear; and
a processor configured to execute the instructions to perform a method comprising:
capturing image data and/or measurement data of at least a portion of a user's anatomy;
generating an anatomic model of the at least the portion of the user's anatomy and the parametric model of the eyewear product based on the captured image data and/or measurement data;

determining, using the anatomic model, an interpupillary distance, a vertex distance, a pantoscopic tilt, a frame wrap, or a combination thereof based on the user's anatomy to automatically update one or more geometric parameters of the parametric model;

determining prescription information, wherein an estimated average of prescription lens is calculated upon determining an absence of the prescription information; and generating a presentation of: (i) the updated parametric model with instructions for manufacturing a physical embodiment of the eyewear product according to the updated parametric model and (ii) lenses of the updated parametric model at a particular size, shape, and thickness based on the estimated average of the prescription lens.

13. The system of claim 12, wherein the processor is further configured for:

receiving one or more inputs from the user to adjust at least one configurable portion of the updated parametric model; and modifying the at least one configurable portion of the updated parametric model based on the one or more inputs, wherein the instructions for manufacturing the physical embodiment of the eyewear product is further based on the modified configurable portion of the updated parametric model.

14. The system of claim 13, wherein the processor is further configured for:

automatically modifying a frame portion of the parametric model in response to a modification to lens portion of the parametric model; or automatically modifying the lens portion of the parametric model in response to a modification to the frame portion of the parametric model.

15. The system of claim 12, wherein the processor is further configured for:

optimizing one or more parameters of the parametric model based on pre-defined fit metrics, wherein the pre-defined fit metrics include an optimal ratio of eyewear product's width to a width of a user's face, an optimal centering of eyes within lenses of the parametric model, or a combination thereof.

16. The system of claim 12, wherein the processor is further configured for determining the prescription information by:

receiving, via a user interface, the prescription information pertaining to the eyewear product associated with the user; and rendering the lenses of the updated parametric model at the particular size, shape, and thickness based on the prescription information.

17. A non-transitory computer readable medium for use on a computer system containing computer-executable programming instructions for configuring a parametric model of an eyewear product, method comprising:

capturing image data and/or measurement data of of at least a portion of a user's anatomy;

generating an anatomic model of the of at least a portion of the user's anatomy and the parametric model of the eyewear product based on the captured image data and/or measurement data;

determining, using the anatomic model, an interpupillary distance, a vertex distance, a pantoscopic tilt, a frame wrap, or a combination thereof based on the user's anatomy to automatically update one or more geometric parameters of the parametric model;

determining prescription information, wherein an estimated average of prescription lens is calculated upon determining an absence of the prescription information; and generating a presentation of: (i) the updated parametric model with instructions for manufacturing a physical embodiment of the eyewear product according to the updated parametric model and (ii) lenses of the updated parametric model at a particular size, shape, and thickness based on the estimated average of the prescription lens.

18. The non-transitory computer readable of claim 17, further comprising:

receiving one or more inputs from the user to adjust at least one configurable portion of the updated parametric model; and modifying the at least one configurable portion of the updated parametric model based on the one or more inputs, wherein the instructions for manufacturing the physical embodiment of the eyewear product is further based on the modified configurable portion of the updated parametric model.

* * * * *

UNITED STATES PATENT AND TRADEMARK OFFICE
CERTIFICATE OF CORRECTION

Page 1 of 1

PATENT NO. : 11,867,979 B2
APPLICATION NO. : 17/868007
DATED : January 9, 2024
INVENTOR(S) : Timothy A. Fonte and Eric J. Varady It is certified that error appears in the above-identified patent and that said Letters Patent is hereby corrected as shown below:

On the Title Page

(72) Inventors, Line 1, after "Timothy" delete "A" and insert --A.--

In the Claims

In Column 66, Line 52, Claim 11, after "embodiment" insert --of--

In Column 68, Line 11, Claim 17, after "data of" delete "of"

In Column 68, Line 13, Claim 17, after "of the" delete "of"

Signed and Sealed this
Twenty-seventh Day of February, 2024

Katherine Kelly Vidal
*Director of the United States Patent and Trademark Office*